US006511970B1

(12) United States Patent
Rodriguez

(10) Patent No.: US 6,511,970 B1
(45) Date of Patent: Jan. 28, 2003

(54) PREVENTION OF OVARIAN CANCER BY ADMINISTRATION OF PRODUCTS THAT INDUCE TRANSFORMING GROWTH FACTOR-BETA AND/OR APOPTOSIS IN THE OVARIAN EPITHELIUM

(75) Inventor: Gustavo C. Rodriguez, Durham, NC (US)

(73) Assignee: New Life Pharmaceuticals Inc., Chicago, IL (US)

( * ) Notice: Subject to any disclaimer, the term of this patent is extended or adjusted under 35 U.S.C. 154(b) by 0 days.

(21) Appl. No.: 09/672,735

(22) Filed: Sep. 28, 2000

Related U.S. Application Data

(63) Continuation-in-part of application No. 09/528,963, filed on Mar. 21, 2000, and a continuation-in-part of application No. 09/532,340, filed on Mar. 21, 2000, now abandoned, which is a continuation-in-part of application No. 09/464,899, filed on Dec. 16, 1999, now Pat. No. 6,310,054, which is a continuation of application No. 08/713,834, filed on Sep. 13, 1996, now Pat. No. 6,028,064, which is a continuation-in-part of application No. 09/118,143, filed on Jul. 16, 1998, now Pat. No. 6,319,911, which is a continuation-in-part of application No. 08/713,834, which is a continuation-in-part of application No. 09/479,021, filed on Jan. 7, 2000, now Pat. No. 6,444,658, which is a continuation of application No. 08/873,010, filed on Jun. 11, 1997, now Pat. No. 6,034,074, which is a continuation-in-part of application No. 08/713,834.

(51) Int. Cl.[7] .............................................. A61K 31/56
(52) U.S. Cl. ...................... 514/179; 514/170; 514/178; 514/181
(58) Field of Search ................................ 514/170, 179, 514/178, 181

(56) References Cited

U.S. PATENT DOCUMENTS

| | | | |
|---|---|---|---|
| 3,608,075 A | 9/1971 | Glen et al. ................... | 424/238 |
| 3,957,982 A | 5/1976 | Lachnit-Fixson et al. ... | 424/238 |
| 3,969,502 A | 7/1976 | Lachnit-Fixson ........... | 424/239 |
| 4,390,531 A | 6/1983 | Edgren ....................... | 424/239 |
| 4,530,839 A | 7/1985 | Pasquale ..................... | 514/171 |
| 4,544,554 A | 10/1985 | Pasquale ..................... | 514/170 |
| 4,594,340 A | 6/1986 | Partridge et al. ........... | 514/167 |
| 4,616,006 A | 10/1986 | Pasquale ..................... | 514/170 |
| 4,621,079 A | 11/1986 | Lachnit-Fixson et al. ... | 514/170 |
| 4,628,051 A | 12/1986 | Pasquale ..................... | 514/170 |
| 4,757,061 A | 7/1988 | Faustini et al. ............. | 514/177 |
| 4,760,053 A | 7/1988 | Labrie ......................... | 514/15 |
| 4,800,198 A | 1/1989 | DuLuca et al. ............. | 514/167 |
| 4,808,578 A | 2/1989 | Faustini et al. ............. | 514/177 |
| 4,808,616 A | 2/1989 | Buzzetti et al. ............. | 514/177 |
| 4,814,327 A | 3/1989 | Ottow et al. ................. | 514/179 |
| 4,817,819 A | 4/1989 | Kelly ........................... | 221/2 |
| 4,840,943 A | 6/1989 | Buzzetti et al. ............. | 514/177 |
| 4,870,069 A | 9/1989 | Ottow et al. ................. | 514/179 |
| 4,904,650 A | 2/1990 | Buzzetti et al. ............. | 514/177 |
| 4,921,843 A | 5/1990 | Pasquale ..................... | 514/170 |
| 4,931,283 A | 6/1990 | Tsuk ........................... | 424/449 |
| 4,933,184 A | 6/1990 | Tsuk ........................... | 424/449 |
| 4,954,790 A | 9/1990 | Barber ........................ | 332/164 |
| 4,962,098 A | 10/1990 | Boissonneault ............. | 514/170 |
| 5,006,518 A | 4/1991 | Moguilewsky ............... | 514/179 |
| 5,081,114 A | 1/1992 | Gourvest et al. ........... | 514/177 |
| 5,086,047 A | 2/1992 | Gourvest et al. ........... | 514/177 |
| 5,089,488 A | 2/1992 | Ottow et al. ................. | 514/179 |
| 5,108,995 A | 4/1992 | Casper ........................ | 514/170 |
| 5,190,935 A | 3/1993 | Binderup et al. ........... | 514/167 |
| 5,206,229 A | 4/1993 | Calverly et al. ............. | 514/167 |
| 5,210,081 A | 5/1993 | Reveendranath et al. ... | 514/179 |
| 5,227,375 A | 7/1993 | Labrie et al. ................ | 514/172 |
| 5,246,925 A | 9/1993 | DuLuca et al. ............. | 514/167 |
| 5,256,421 A | 10/1993 | Casper ........................ | 424/449 |
| 5,262,408 A | 11/1993 | Bergink ....................... | 514/182 |
| 5,278,155 A | 1/1994 | Ikekawa et al. ............. | 514/167 |
| 5,280,023 A | 1/1994 | Ehrlich et al. ............... | 514/177 |
| 5,288,717 A | 2/1994 | Raveendranath et al. ... | 514/179 |
| 5,314,694 A | 5/1994 | Gale et al. ................... | 424/448 |
| 5,362,720 A | 11/1994 | Labrie ......................... | 514/169 |
| 5,364,847 A | 11/1994 | Labrie et al. ................ | 514/182 |
| 5,373,004 A | 12/1994 | DeLuca et al. .............. | 514/167 |
| 5,374,629 A | 12/1994 | Calverley et al. ........... | 514/167 |
| 5,380,720 A | 1/1995 | DeLuca et al. .............. | 514/167 |
| 5,382,573 A * | 1/1995 | Casper ........................ | 514/170 |
| 5,387,582 A | 2/1995 | Hansen ....................... | 514/167 |
| 5,389,622 A | 2/1995 | Posner et al. ............... | 514/167 |
| 5,401,731 A | 3/1995 | Calverley et al. ........... | 514/167 |
| 5,411,949 A | 5/1995 | Neef et al. .................. | 514/167 |
| 5,418,228 A * | 5/1995 | Bennink ...................... | 514/182 |
| 5,422,119 A | 6/1995 | Casper ........................ | 424/449 |
| 5,428,029 A | 6/1995 | Doran et al. ................ | 514/167 |
| 5,434,146 A | 7/1995 | Labrie et al. ................ | 514/169 |

(List continued on next page.)

FOREIGN PATENT DOCUMENTS

| | | |
|---|---|---|
| EP | 0 253 607 B1 | 7/1987 |
| EP | 0 253 607 A1 | 7/1987 |
| EP | 0 628 312 A1 | 2/1994 |
| WO | WO 95/26730 | 10/1995 |
| WO | WO 98/10771 | 3/1998 |

OTHER PUBLICATIONS

Allgood, V.E., et al., "Analysis Of Chicken Progesterone Receptor Function And Phosphorylation using An Adenovirus–Mediated Procedure For High–Efficiency DNA Transfer," *Biochemistry*, 36(1):224–232 (1997).

Arends, M.J. et al., "Apoptosis: Mechanisms And Roles In Pathology," *Int. Rev. Exp. Pathol.*, 32:223–254 (1991).

(List continued on next page.)

*Primary Examiner*—James H. Reamer
(74) *Attorney, Agent, or Firm*—Raymond N. Nimrod

(57) ABSTRACT

The present invention relates to compositions and methods for preventing the development of epithelial ovarian cancer by administering compounds in an amount capable of increasing TGF-$\beta$ expression in the ovarian epithelium. HRT and OCP regimens comprising such compositions and methods are disclosed.

33 Claims, No Drawings

U.S. PATENT DOCUMENTS

| | | | |
|---|---|---|---|
| 5,446,035 A | 8/1995 | Neef et al. | 514/167 |
| 5,451,574 A | 9/1995 | Baggiolini et al. | 514/167 |
| 5,461,041 A | 10/1995 | Bergink et al. | 514/178 |
| 5,468,736 A | 11/1995 | Hodgen | 514/179 |
| 5,484,782 A | 1/1996 | DeLuca et al. | 514/167 |
| 5,486,511 A | 1/1996 | Weintraub et al. | 514/178 |
| 5,496,813 A | 3/1996 | Eugster et al. | 514/172 |
| 5,502,044 A | 3/1996 | Buzzetti et al. | 514/177 |
| 5,512,554 A | 4/1996 | Baggiolini et al. | 514/167 |
| 5,532,228 A | 7/1996 | Neef et al. | 514/167 |
| 5,536,713 A | 7/1996 | DuLuca et al. | 514/167 |
| 5,547,947 A | 8/1996 | Dore et al. | 514/167 |
| 5,552,394 A * | 9/1996 | Hodgen | 514/178 |
| 5,554,599 A | 9/1996 | GrueSorenen et al. | 514/167 |
| 5,595,970 A | 1/1997 | Garfield et al. | 514/12 |
| 5,620,705 A | 4/1997 | Dong et al. | 424/472 |
| 5,633,011 A | 5/1997 | Dong et al. | 424/451 |
| 5,741,786 A | 4/1998 | Hamersma et al. | 514/173 |
| 5,747,480 A * | 5/1998 | Gast | 514/179 |
| 5,770,227 A | 6/1998 | Dong et al. | 424/480 |
| 5,780,497 A | 7/1998 | Miller et al. | 414/414 |
| 5,783,208 A | 7/1998 | Yenkateshwaran et al. | 424/448 |
| 5,811,416 A | 9/1998 | Chwalisz et al. | 514/177 |
| 5,827,876 A | 10/1998 | Sabatucci | 514/448 |
| 5,842,476 A * | 12/1998 | Wright et al. | 128/898 |
| 5,855,906 A | 1/1999 | McClay | 424/433 |
| 5,858,405 A | 1/1999 | Gast | 424/464 |
| 5,876,746 A | 3/1999 | Jona et al. | 424/449 |
| 5,880,137 A | 3/1999 | Miller et al. | 514/323 |
| 5,888,543 A * | 3/1999 | Gast | 424/464 |
| 5,891,868 A | 4/1999 | Cummings et al. | 514/178 |
| 5,898,038 A | 4/1999 | Yallampalli et al. | 514/742 |
| 5,922,349 A | 7/1999 | Elliesen et al. | 424/449 |
| 5,922,542 A | 7/1999 | Ralston et al. | 435/6 |
| 5,948,775 A | 9/1999 | Koko et al. | 514/212 |
| 5,962,444 A | 10/1999 | Cook et al. | 514/177 |
| 5,972,377 A | 10/1999 | Jona et al. | 424/449 |
| 5,985,910 A | 11/1999 | Miller et al. | 514/415 |
| 5,994,337 A | 11/1999 | Washburn et al. | 514/182 |
| 5,998,137 A | 12/1999 | Grainter et al. | 435/6 |
| 6,001,846 A | 12/1999 | Edwards et al. | 514/285 |
| 6,015,805 A | 1/2000 | Cook et al. | 514/176 |
| 6,020,328 A | 2/2000 | Cook et al. | 514/176 |
| 6,028,064 A | 2/2000 | Rodriguez | 514/177 |
| 6,034,074 A | 3/2000 | Rodriguez et al. | 514/167 |
| 6,310,054 B1 | 10/2001 | Rodriguez | 514/179 |
| 6,319,911 B1 | 11/2001 | Rodriguez | 514/170 |

OTHER PUBLICATIONS

Arrick, B.A., et al., "Differential Regulation Of Three Transforming Growth Factor b Species In Human Breast Cancer Cell Lines By Estradiol," *Cancer Res., 50:*299–303 (1990).

Bai, W. et al., "Differential Phosphorylation Of Chicken Progesterone Receptor In Hormone–Dependent And Ligand–Independent Activation," J. Biol. Chem., 272(16):10457–10463 (1997).

Bates, R.C. et al. "Involvement of Integrins In Cell Survival," *Cancer Metastasis Rev, 14(3)*:191–203 (1995).

Berchuck, A. et al., "Regulation Of Growth Of Normal Ovarian Epithelial Cells And Ovarian Cancer Cell Lines By Transforming Growth, Factor–Beta," *Am. J. Obstet. Gynecol., 166:*676–84 (1992).

Berchuck, A., et al., "The Role Of Peptide Growth Factors In Epithelial Ovarian Cancer," *Obstet. Gynecol, 75:*255–62 (1990).

Brenner, R.M. et al., "Cyclic Changes In The Primate Oviduct And Endometrium. In: The Physiology Of Reproduction," Knobil, E. et al., (eds.), New York: Raven Press, pp. 541–569 (1994).

Bu, S.Z. et al., "Progesterone Induces Apoptosis An Up–Regulation of p53 Expression In Human Ovarian Carcinoma Cell Lines," *Cancer, 79:*1944–1950 (1997).

Bundesverband der Pharmazeutishen Industrie, "Rote liste 1995," Ecv. Editio Cantor, *Aulendorf* (DE), pp. 75023–75024 (1995).

Chan, L.N. et al., "N–(4–Hydroxyphenyl) Retinamide Prevents Development Of Tlymphomas In AKR/J Mice," *Anti-cancer Research,* 17:499–503 (1997).

Cohen, J.J., "Apoptosis," *Immun. Today, 14:*126–130 (1993).

Delia, D. et al., "N–(4–hydroxyphenyl) Retinamide Induces Apoptosis Of Malignant Hemopoietic Cell Lines Including Those Unresponsive To Retinoic Acid," *Cancer Res.* 53(24):6036–61 (1993).

Eguchi, Y. et al., "Isolation And Characterization Of The Chicken bcl–2 Gene: Expression In A Variety Of Tissues Including Lymphoid And Neuronal Organs In Adult And Embryo," *Nucleic Acids Research,* 20(16):4187–4192 (1992).

el–Bayoumy, K. et al., "Chemo Prevention Of Cancer By Organoselenium Compounds," *J. Cell. Biochem, Suppl., 22:*92–100 (1995).

Ellis, R. et al., "Mechanisms of Cell Death," *Ann. Rev. Cell. Bio., 17:*663–698 (1991).

Evans, D.L. et al., "Molecular Evolution And Secondary Structural Conservation In The B–Cell Lymphoma Leukemia 2 (bcl–2) family Of Proto–Oncogene Products," *J. Mol. Evol., 41(6)*:775–83 (1995).

Fredrickson, T.N. et al., "Ovarian Tumors Of The Hen," *Environ Health Perspect, 73:*35–44 (1987).

Gentry, L.E. et al., "Type I Transforming Growth Factor–Beta: Amplified Expression And Secretion Of Mature And Precursor Polypeptides In Chinese Hamster Ovary Cells," *Mol. Cell. Biol., 7:*3418–27 (1987).

Grimes et al., "Primary Prevention Of Gynecologic Cancers," *Am. J. Obstetrics And Gynecology, 172(1)*:227–235 (1995).

Havrilesky, L.J., et al., "Regulation Of Apoptosis In Normal And Malignant Ovarian Epithelial Cells by Transforming Growth Factor–Beta," *Cancer Research,* 55:944–948 (Feb. 15, 1995).

Hickey, M.J., et al., "Metabolic And Endocrinology Effects Of Steroidal Contraception Obstetrics," Ch. 24, J. Sciarra, Editor, 1996 revised edition, Lippincott, Philadelphia, pp. 1–14 (1996).

Hotckhiss, J. et al., "The Menstrual Cycle And Its Neuroendocrine Control," In: *The Physiology Of Reproduction,* Knobil, E. et al. (eds.), New York: Raven Press, Pp. 711–736 (19940).

Hurteau, J.A., et al., "Transforming Growth Factor–Beta Inhibits Proliferation Of Human Ovarian Cancer cells Obtained From Ascites," *Cancer 74:*93–99 (1994).

Johnson, A.J. et al., Expression of bcl–2 And nr–13 In Hen Ovarian Follicles During Development, *Biol. Repro.,* 57:1096–1103 (1997).

Kaiserman–Abramof, L et al., "Ultrastructural Epithelial Conation Of The Primate Endometrium (Rhesus Monkey)," *Am. J. Anat.,* pp. 13–30 (1989).

Lingeman, C.H., "Etiology Of Cancer Of The Human Ovary," A Review, *J. Natl. Cancer Inst*.m 53: 1603–1618 (1974).

Lotan, R., Retinoids In Cancer Chemo Prevention, [Review] *FASEB J.,* 10(9): 1031–1039, (1996).

Lumbiganon, P., "Depot–Medroxyprogesterone Acetate (DMPA) And Cancer Of The Endometrium And Ovary," *Contraception,* 49: 203–209 (Mar. 1994).

Mulheron, G.W., et al., "Rat ThecalInterstitial Cells Express Transforming Growth Factor–Beta Type 1 and 2 Is Regulated By Gonadotropin In Vitro," *Endocrin,* 129: 368–374 (1991).

Mulheron, G.W. et al., "Rat Granulosa Cells Express Transforming Growth Factor–Beta Type 2 Messenger Ribonucleic Acid Which Is Regulated By Fillide Stimulating Hormone In Vetro," *Endocrin,* 126:1777–1779 (1990).

Mutch, D.G., et al., "Biology Of Epithelial Overian Cancer," *Clin. Obstet. Gynecol.,* 37:406–422 (1994).

O'Brien V. et al., "Expression Of THe Integrin Alpha 5 Subunit In HT29 Colon Carcinoma Cells Suppresses Apoptosis Triggered By Serum Deprivation," Ex Cell. Res. 224(1): 208–213 (1996).

Oberhammer, F.A., et al., "Induction Of Apoptosis In Cultured Hepatocytes And In Regressing Liver By Transforming Growth Factor–Beta 1," Proc. Natl. Acad. Sci. USA, 89:408–5412 (1992).

Oridate N. et al., "Inhibition Of Proliferation And Injunction Of Apoptosis In Certical Carcinoma Cells by Retinoids: Implications For Chemo Prevention," J. Cell. Biochem, Suppl. 23:80–86 (1995).

Pasquele, R.M., et al. "Chemoprevention By S–Adenosyl–L–Methionine Of Rat Liver Carcinogenesis Intiated by 1,2–dimethylhydrazine Adn Promoted By Orotic Acid," Carcinogenesis 16(2): 427–30 (1995).

Pfleiderer, "di Problematik einer prophylaktischen Chemotherapie, einer der Remission bei der Therapie des Ovarialkarzinoms," *Gerburstsh U. Frauenheilk,* 36(2):132–139 (1976).

Physician's Desk Reference 1996, Product Information, pp. 1871–1876, 2135–2138, 2601–2604, 2759–2762, and 2813–2818 (1996).

Ponzoni, M. et al., "Differential Effects Of N–(4–hydroxyphenyl) Retinamide And Retinoic Acid On Neuroblastoma Cells: Apoptosis Versus Differentiation," *Can. Res.,* 55(4):853–61 (1995).

Qin, S., et al., "Cooperation Of Tyrosine Kinases p72syk and p53/561yn Regulates Calcium Mobilization In Chicken B Cell Oxidant Stress Signaling," *Eur. J. Biochem,* 236(2):443–9 (1996).

Rampalli, A.M., et al., "Insulin Regulates Expression Of c–fos And c–jun and Suppresses Apoptosis Of Lens Epithelial Cells," *Cell. Growth Differ.,* 6(8):945–53 (1995).

Reddy, B.S., et al., "Chemo Prevention Of Colon Carcinogenesis by Dietary Perillyl Alcohol," *Cancer Res.,* 57(3):420–5 (1997).

Roberts, A.B., et al. "Mechanistic Interrelationships Between Two Superfamilies: The Steroid Retinoid Receptors And Transforming Growth Factor–Beta," In: Cancer Surveys, vol. 14: Growth Regulation By Nuclear Hormone Receptors, *Imperial Cancer Research Fund,* pp. 205–217 (1992).

Rodriguez, G.C., et al., "Epidermal Growth Factor Receptor Expression In Normal Ovarian Epithelium And Ovarian Cancer. II. Relationship Between Receptor Expression And Response To Epidermal Growth Factor," *Am. J. Obstet. Gynecol.,* 164:745–750 (1991).

Rotello, R.J., et al., "Coordinated Regulation of Apoptosis And Cell Proliferation By Transforming Growth Factor–Beta 1 In Cultured Uterine Epithelial Cells," *Proc. Natl. Acad. Sci. USA,* 88:3412–3415 (1991).

Rudel, H.W., "Pharmacology Of Contraceptive Steroids," Chapter 19, In: Gynecology and Obstetrics J. Sciarra, Editor, 1996 revised edition, Lippincott, Philadelphia, pp. 3–6 (1996).

Sankaranarayanan, R., et al., "Retinoids As Cancer–Preventive Agents," [Review] *IARC Sci. Publ., (139)*:47–59 (1996).

Schildkraut, J.M. et al., "Relationship Between Lifetime Ovulatory Cycles And Overexpression Of Mutant p53 In Epithelial Ovarian Cancer," *J. National Cancer Institute,* 89(13):932–938 (Jul. 2, 1997).

Scott, J.S., "How To Induce Ovarian Cancer: And How Not To," *British Medical J., 289:*781–784 (Sep. 29, 1984).

Seewaldt, V.L. et al., "All–Trans–Retinoic Acid Mediates GI Arrest But Not Apoptosis Of Normal Human Mammary Epithelial Cells," *Cell Growth Differs.,* 6(7):631–41 (1995).

Syvala, H. et al., "Expression Of The Chicken Progesterone Receptor Forms A And B Is Differentially Regulated By Estrogen In Vivo," *Biochemical and Biophysical Research Communications, 231:*573–576 (1997).

Taetle, R., et al., "Effects Of Transforming Growth Factor––Beta 1 On Growth And Apoptosis Of Human Acute Myelogenous Leukemia Cells," *Cancer Research, 53:*3386–3393 (1993).

Takayama, S. et al., "Evolutionary Conservation Of Function Among Mammalian, Avian, And Viral Homologs Of The bcl–2 Oncoprotein," *DNA Cell. Biol. 13(7):*679–92 (1994).

Thompson, H.J. et al., "Sulfone Metabolite Of Sulindac; Inhibits Mammary Carcinogenesis," *Cancer Res.,* 57(2):267–71 (1997).

Thompson H.J. et al., "Ip C. Comparison Of The Effects Of An Organic And Inorganic Form Of Selenium On A Mammary Carcinoma Cell Line," *Carcinogenesis 15*(2):183–6 (1994).

Toma, S. et al., "Effects of Al–Trans–Retinoic Acid And 13–Cis–Retinoic Acid On Breast–Cancer Cell Lines: Growth Inhibition And Apoptosis Induction," *Int. J. Cancer, 70*(5):619–27 (1997).

Vilgrasa, X. et al., "Differential Expression of bcl–2 and bcl–x During Chicken Spermatogenesis," *Mol. Reprod. Dev., 47(1):*26–9 (1997).

Wakefield, L. et al., "Regulation Of Transforming Growth Factor–Beta Subtypes By Members Of The Steroid Hormone Superfamily," *J. Cell. Sci. Suppl. 13:*139–148 (1990).

Wijsman, J.H. et al., "A New Method To Detect Apoptosis In Paraffin Sections: In Situ End–Labeling Of Fragmented DNA," *J. Histochem. Cytochem., 41:*7–12 (1993).

Woolveridge, I., et al., "The Inhibition Of Androstenedione Production In Mature Thecal Cells From The Ovary Of The Domestic Hen (*Gallus domesticus*): Evidence For the Involvement Of Progestins," *Steroids, 62:*214–220 (1997).

Yanagihara, K. et al., "Transforming Growth Factor–Beta 1 Induces Apoptotic Cell Death In Cultured Human Gastric Carcinoma Cells," *Cancer Res., 52:*4042–4045 (1992).

PCT International Search Report; PCT/US97/16601.

Dolivet et al., "Current Knowledge On The Action Of Retionoids In Carcinoma Of The Head And Neck," [Review], *Rev. Laryngol. Otol. Rhinol. (Bord) 117(1)*:19–26 (1996) (English abstract).

Etches et al., "Reptilian And Avian Follicular Hierarchies: Models For The Study Of Ovarian Development," *J. Exp. Zoo., Suppl. 4:*112–122 (1990).

Fukuda et al., "Induction Of Apoptosis by Transforming Growth Factor–1 In The Rat Hepatoma Cell Fine McA–RH7777: A Possible Associate With Tissue Transglutaminase Expression," *Hepatology, 18:*945–953 (1993).

Gould, "Cancer Chemoprevention And Therapy By Monoterpenes," *Environ. Health Perspect., 105 (Suppl 4)*:977–9 (1997).

Kuo, "Antiproliferative Potency Of Sturcturally Distinct Dietary Flavonoids On Human Colon Cancer Cells," *Cancer Lett., 110(1–2)*:41–8 (1996).

Mayr et al., "Sequence Of An Exon Of Tumour Suppressor p53 Gene—A Comparative Study In Domestic Animals: Mutation In A Feline Comparative Study In Domestic Animals; Mutation In A Feline Solid Mammary Carcinoam" *Br. Vet. J., 151(3)*:325–9 (1995).

Wilson "Adeno–Carcinomata In Hens Kept In A Constant Environment," *Poult. Sci., 37:*1253 (1958).

Milligan et al., "Programmed Cell Death During Development Of Animals," *Cellular Aging and Cell Death:* Wiley–Liss Inc., Holbrook, et al., (Eds), pp. 181–208 (1996).

Canman et al., "DNA Damage Responses: P–53 Induction, Cell Cycle Pertubations, And Apoptosis," *Cold Spring Harbor Symp. Quant. Biol., 59:*277–286 (1994).

Baker et al., "Etiology, Biology, And Epidemiology Of Ovarian Cancer," *Seminars in Surgical Oncology 10:*242–248 (1994).

Amos et al., "Genetic Epidemiology Of Epithelial Ovarian Cancer," *Cancer 71:*566–72 (1993).

Wittemore, Characteristics Relating to Ovarian Cancer Risk: Implications For Preventing And Detection,Gynecologic Oncology 55: S15–S19, 1994.

Greene et al., "The Epidemiology Of Ovarian Cancer," *Seminars In Oncology, 11:*209–225 (1984).

Wittemore et al., "Characteristics Relating to Ovarian Cancer Risk: Collaborative Analysis Of 12 US Case–Control Studies," *Am. J. Epidem. 136:*1212–1220 (1992).

Wu et al., "Personal And Environmental Characteristics Related To Epithelial Ovarian Cancer," *Am. J. Epidem., 108(6)*: 1216–1227 (1988).

Rossing et al., "Ovarian Tumors In A Cohort Of Infertile Women," *New Engl. J. Med., 331:*771–776 (1994).

Casagrande et al., "Incessant Ovulation" and "Ovarian Cancer," *Lancet* at pp. 170–172 (Jul. 28, 1979).

Rosenberg et al., (the WHO Collaborative Study Of Neoplasia And SteroiD Contraceptives) "A Case Control Study Of Oral Contraceptive Use and Invasive Epithelial Ovarian Cancer," *Am. J. Epidem., 139:*654–661 (1994).

Stanford et al., "Epithelial Ovarian Cancer And Combined Oral Contraceptives," *Int'l J. Epidem., 18:*538–545 (1989).

Lee et al., "The Reduction In Risk Of Ovarian Cancer Associated With Oral Contraceptive Use," *New Engl. J. Med., 316:*650–655 (1987).

Gross et al., "The Estimated Effect Of Oral Contgraceptive Use On The Cumulative Risk Of Epithelial Ovarian Cancer," *Obstetrics Gynecology, 83:*419–24 (1994).

Franseschi et al., "Pooled Analysis Of 3 European Case–Control Studies Of Epithelial Ovarian Cancer: III. Oral Contraceptive Use," *Int'l J. Cancer, 49:*61–65 (1991).

Rosenblatt et al., "High–Dose and Low–Dose Combined Oral Contraceptives: Protection Against Epithelial Ovarian Cancer and The Length Of The Protective Effect," *J. Cancer, 28A:* 1872–76, 1992.

Stanford et al., (The WHO Collaborative Study Of Neoplasia And Steroid), "Depot–Medroxyprogesterone Acetate (DMPA) And Risk Of Epithelial Ovarian Cancer," *Int'l J. Cancer, 49:*191–195 (1991).

Liang et al., "Risk Of Breast, Uterine Corpus, And Ovarian Cancer In Women Receiving Medroxyprogesterone Injections," *JAMA, 249:*2909–2912 (1983).

Lowe et al., "P53–Dependent Apoptosis in Tumor Progression And In Cancer Therapy," Cellular Aging And Cell Death: Wiley–Liss Inc., Holbrook et al., (Eds.), pp. 209–234 (1996).

Lockshin et al., "The Biology of Cell Death and Its Relationship to Aging,," *Cellular Aging and Cell Death,* Wiley–Liss Inc., Holbrook et al., (Eds.), pp. 167–180 (1996).

Bast et al., "Ovarian Cancer," Harrison's Principles Of Internal Medicine, Thirteenth Edition, Isselbacher et al., (Eds.), McGraw–Hill, New York, Chapter 321, pp. 1853–1858 (1994).

Rodriguez et al., "Estrogen Replacemenet Therapy And Fatal Ovarian Cancer," *Am. J. Epidem., 141:*828–835 (1995).

Dunn, I.C., et al., "The Effect of Photoperiodic History On Egg Laying In Dwarf Broiler Hens," In: Physiology And Reproduction on: *Poultry Science, vol. 71,* pp. 2090–2098 (1992).

Christopherson, W.A. et al., "Responsiveness Of Human Carcinoma Cells Of Gynecologic Origin To 1,25–Dihydroxycholecalciferol," *Am. J. Obstet. Gynecol., 155(6)*:1293–1296 (1986).

Moore, T.B., et al., "Differentiating Effects of 1,25–Dihydroxycholecalciferol (D3) on La–N–5 Human Neuroblastoma Cells And Its Synergy With Retinoic Acid," *Journal Of Petriatric Hematology/Oncology, 17(4)*:311–317 (Nov., 1995).

Rustin, G.J.S. et al., "Trial Of Isotretinoin And Calcitriol Monitored By CA 125 In Patients With Ovarian Cancer," *British Journal Of Cancer, 74(9)*:1479–1481 (1996).

Saunders, D.E., et al., Repression Of c–myc Expression In Ovarian Carcinoma Cells by 1,25–Dihydroxyvitamin D3, Twenty–Third Annual Meeting Of The Society Of Gynecologic Oncologiest, Mar. 15–18, 1992. *Gynecol. Oncol., 45(1)*:83–84 (1992) (Abstract).

Saunders, D.E. et al., "Receptors for 1,25–Dihydroxyvitamin D3 in Gynecologic Neoplasms," *Gynecologic Oncology, 44(2)*:131–136 (1992).

Saunders, D.E. et al., "Nonreproductive Hormones As Biologic Modifiers In Ovarian Carcinomas," Twenty–Fourth Annual Meeting Of The Society Of Gynecologic Oncologiest, Feb. 7–10, 1993. *Gynecol. Oncol., 49(1)*:118 (1993) (Abstract).

Saunders, D.E. et al., "Inhibition Of c–myc In Breast And Ovarian Carcinoma Cells by 1,25–Dihydroxyvitamin D3, Retinoic Acid And Dexamethasone," *Anti–Cancer Drugs, 4(2)*:201–208 (1993).

Saunders, D.E. et al., "Inhibition Of Breast And Ovarian Carcinoma Cell Growth By 1,25–Dihydroxyvitamin D3, Combined With Retonic Acid Or Dexamethasone," *Anti-–Cancer Drugs*, 6(4):562–569 (1995).

Corder, E.H., et al., "Vitamin D And Prostate Cancer: a Prediagnostic Study With Stored Sera," *Cancer Epidemiology, Biomarkers & Prevention*, 2:467–472 (1993).

Santiso–Mere et al., "Positive Regulation Of The Vitamin D Receptor By Its Cognate Ligand In Heterolngous Expression Systems," *Molecular Endocrinology* 7(7):833–839 (1993).

Davoodi et al., "Modulation Of Vitamin D Receptor An Estrogen Receptor By 1,25 (OH)2–Vitamin D3 In T–47D Human Breast Cancer Cells," *J. Steroid Biochem. Molec. Biol.*, 54(3/4):147–153 (1995).

Colston et al., "1–25–Dihydroxyvitamin D3 And Malignant Melanoma: The Presence Of Receptors And Inhibition Of Cell Growth In Culture," *Endocrinology*, 108:1083–1086 (1981).

Sato et al., "Antitumor Effect of 1a–Hydroxyvitamin D3," *Tohoku J. Exp. Med.*, 138:445–446 (1982).

Eisman et al., "Suppression Of In Vivo Growth Of Human Cancer Solid Tumor Xenografts By 1,25–Dihydroxyvitamin D3," *Cancer Research*, 47:21–25 (1987).

Dokoh et al., "Influence of 1,25–Dihydroxyvitamin D3 on Cultured Osteogenic Sarcoma Cells: Correlation With The 1,25–Dihydroxyvitamin D3 Receptor," *Cancer Research*, 44:2103–2109 (1984).

Mangelsdorf et al., "1,25–Dihydroxyvitamin D3–induced Differentiation In A Human Promyelocytic Leukemia Cell Line (HL–60): Receptor Mediated Maturation To Macrophage–Like Cells," *J. Cell. Biol.*, 98:391–398 (1984).

Chida et al., "Inhibition Of Tumor In Mouse Skin By 1a, 25–Dihydroxyvitamin D31," *Cancer Research*, 45:5426–5430 (1985).

Oikawa et al., Antitumor Effect Of 22–oxa–1a–Dihydroxyvitamin D3, A Potent Angiogenesis Inhibitor, On Rat Mammary Tumors Induced by 7,12–Dimethylbenz[a]anthracene, *Anti–Cancer Drugs*, 2:475–480 (1991).

Frampton et al., "Inhibition Of Human Cancer Cell Growth By 1,25–Dihydroxyvitamin D3 Metabolites1," *Cancer Research*, 43:4443–4447 (1983).

Sporn, M.B. et al., "Prevention Of Carciogenesis With Vitamin D Analogs," *Proceedings American Association For Cancer Research*, No. 34, Abstracts 622 (Mar., 1993).

Saunders et al., "Additive Inhibition of RL95–2 Endometrial Carcinoma Cell Growth By Carboplatin and 1,25–Dihydroxyvitamin D3," *Gynecologic Oncology*, 51:155–159 (1993).

Welsh, J., "Induction Of Apoptosis In Breast Cancer Cells In Response To Vitamin D And Antiestrogens," *Biochem. Cell. Biol.*, 72:537–545 (1994).

Narvaez et al., "Characterization Of A Vitamin D3–Resistant MCF–7 Cell Line," *Endocrinology*, 137(2):400–409 (1996).

Lefkowitz et al., "Sunlight, Vitamin D, And Ovarian Cancer Mortality Rates In U.S. Women," *International Journal Of Epidemiology*, 23(6):1133–1136 (1994).

Studzinski et al., "Sunlight–Can It Prevent As Well As Cause Cancer?" *Cancer Research*, 55:4014–4022 (1995).

Speroff et al., "Steroid Contraception," *Clinical Gynecologic Endocrinology And Infirtility*, Chapter 15, Fourth Edition, pp. 461–498 (1989).

Hammond, "Climateric" *Danforth's Obstetrics And Gynecology*, Chapter 42, Seventh Edition, pp. 771–790 (1994).

Young, "Gynecologic Malignancies, Ovarian Cancer," *Harrison's Principles Of Internal Medicine*, Thirteenth Edition, pp. 1605–608 (1994).

Ravin, L.J. et al., *Remington's Pharmaceutical Sciences*, 18th Ed., Chpts. 75–92 (1990, Mack Publishing Co., Easton, PA 18042).

Wingo, P.A. et al., "Cancer Statistics, 1995," *CA Cancer Journal For Clinicians (A Journal Of The American Cancer Society)*, 45(1):30 (1995).

Dodd, R.C. et al., "Vitamin D Metabolites Change The Phenotype Of Monoblastic U937 Cells," *Proc. Natl. Acad. Sci., USA*, 80:7538–7541 (Dec., 1983).

Gao, Y. et al., "The Effects Of Chemotherapy Including Cisplatin On Vitamin D Metabolism," *Endocrine Journal*, 40(6):737–742 (1993).

United States Patent Application Serial No. 09/479,021 filed on Jan. 7, 2000 (Inventor: Rodriguez et al.); Notice of Allowance mailed on Jun. 22, 2001; Issue Fee paid by attorney for applicant on Jun 25, 2001.

* cited by examiner

PREVENTION OF OVARIAN CANCER BY ADMINISTRATION OF PRODUCTS THAT INDUCE TRANSFORMING GROWTH FACTOR-BETA AND/OR APOPTOSIS IN THE OVARIAN EPITHELIUM

This application is a continuation-in-part of U.S. Ser. No. 09/528,963 filed Mar. 21, 2000. This application is also a continuation-in-part of U.S. Ser. No. 09/532,340 filed Mar. 21, 2000 now abandoned, which was a continuation-in-part of U.S. Ser. No. 09/464,899 filed Dec. 16, 1999 U.S. Pat. No. 6,310,054, which was a continuation application of U.S. Ser. No. 08/713,834 filed on Sep. 13, 1996 U.S. Pat. No. 6,028,064, which also was a continuation-in-part of U.S. Ser. No. 09/118,143 filed on Jul. 16, 1998, U.S. Pat. No. 6,319,911 which was continuation-in-part of application Ser. No. 08/713,834 filed on Sep. 13, 1996 and issued as U.S. Pat. No. 6,028,064 on Feb. 22, 2000, and which was a continuation-in part of of U.S. Ser. No. 09/479,021 filed on Jan. 7, 2000, U.S. Pat. No. 6,444,658 which is a continuation of U.S. Ser. No. 08/873,010 filed on Jun. 11, 1997 which issued as U.S. Pat. No. 6,034,074 on Mar. 7, 2000 and which was a continuation-in-part of application Ser. No. 08/713,834 filed on Sep. 13, 1996 issued as U.S. Pat. No. 6,028,064 on Feb. 22, 2000.

FIELD OF THE INVENTION

The present invention relates generally to methods of preventing or reducing the risk of the development of ovarian cancer by pharmacological approaches available to women of all ages.

BACKGROUND OF THE INVENTION

Ovarian cancer is the fourth leading cause of cancer deaths among women in the United States and causes more deaths than all other gynecologic malignancies combined. In the United States, a woman's lifetime risk of developing ovarian cancer is 1 in 70. In 1992, about 21,000 cases of ovarian cancer were reported, and about 13,000 women died from the disease. Chapter 321, *Ovarian Cancer, Harrison's Principles of Internal Medicine*, 13th ed., Isselbacher et al., eds., McGraw-Hill, New York (1994), pages 1853–1858; *American Cancer Society Statistics, Cancer J. Clinicians*, 45:30 (1995). Epithelial ovarian cancer, the most common ovarian cancer, has a distinctive pattern of spread in which cancer cells migrate throughout the peritoneal cavity to produce multiple metastatic nodules in the visceral and parietal peritoneum and the hemidiaphragms. In addition, metastasis can occur to distant sites such as the liver, lung and brain. Early stage ovarian cancer is often asymptomatic and is detected coincidentally by palpating an ovarian mass on pelvic examination. In premenopausal patients, about 95% of these masses are benign. Even after menopause, 70% of masses are benign but detection of any enlargement requires evaluation to rule out malignancy. In postmenopausal women with a pelvic mass, a markedly elevated serum CA-125 level of greater than 65 U/ml indicates malignancy with a 96% positive predictive value. Chapter 321, *Ovarian Cancer, Harrison's Principles of Internal Medicine*.

Epithelial ovarian cancer is seldom encountered in women less than 35 years of age. Its incidence increases sharply with advancing age and peaks at ages 75 to 80, with the median age being 60 years. The single most important risk factor for this cancer is a strong family history of breast or ovarian cancer. In families in which ovarian, breast, endometrial or colon cancer can be tracked as an apparent autosomal dominant trait, the risk of this cancer can be as high as 50%. Having a single first-degree relative with ovarian cancer increases a woman's risk by at least three-fold, and having a personal history of breast or colorectal cancer increases the risk of subsequently developing ovarian cancer by two-fold. Chapter 321, *Ovarian Cancer, Harrison's Principles of Internal Medicine*. In addition, those with identifiable genetic mutations in genes such as BRCA1 or BRCA2 also have an increased risk. Baker et al., *Etiology, Biology, and Epidemiology of Ovarian Cancer, Seminars in Surgical Oncology* 10: 242–248, 1994; Amus et al., *Genetic Epidemiology of Epithelial Ovarian Cancer, Cancer* 71: 566–72, 1993; Whitmore, *Characteristics Relating To Ovarian Cancer Risk: Implications for Preventing and Detection, Gynecologie Oncology* 55, 515-19, 1994. Oncogenes associated with ovarian cancers include the HER-2/neu (c-erbB-2) oncogene, which is overexpressed in a third of ovarian cancers, the fins oncogene, and abnormalities in the p53 gene, which are seen in about half of ovarian cancers. A number of environmental factors have also been associated with a higher risk of epithelial ovarian cancer, including a high fat diet and intake of lactose in subjects with relatively low tissue levels of galactose-1-phosphate uridyl transferase.

In epidemiological studies, behaviors associated with decreased ovulation, such as pregnancy, breastfeeding and use of estrogen-progestin combination oral contraceptive medications, decrease the risk of ovarian cancer; use of estrogen-progestin combination oral contraceptives for as long as 5 years can reduce the risk of ovarian cancer by 50%. Greene et al., *The Epidemiology of Ovarian Cancer, Seminars Oncology*, 11: 209–225, 1984; Whitmore et al., *Characteristics Relating To Ovarian Cancer Risk: Collaborative Analysis of 12 US Case-Control Studies, American J. Epidemiology* 136: 1212–20, 1992. Conversely, early menarche, late menopause and nulliparity (no pregnancies) have been shown to increase the risk of ovarian cancer. The risk has been shown to positively correlate with the number of ovulatory cycles in a woman's lifetime. Wu et al., *Personal and Environmental Characteristics Related To Epithelial Ovarian Cancer, American J. Epidemiology*, Vol. 108(6) 1216–1227. The long-term use of ovulation-inducing ovarian hyperstimulants such as clomiphene has been shown to be associated with an increased risk of ovarian cancer in some women. Rossary et al., *Ovarian Tumors in a Cohort Of Infertile Women, New Engl. J. Med.*, 331: 771–6, 1994. Thus, some factors that favor prolonged and persistent ovulation have been thought to increase ovarian cancer risk, whereas some factors that suppress ovulation have been thought to decrease risk. Chapter 21, *Ovarian Cancer, Harrison's Principles of Internal Medicine*. These data have led to the "incessant ovulation" hypothesis for the development of ovarian cancer. Casagrande et al., *Incessant Ovulation and Ovarian Cancer, Lancet* at 170–73 (Jul. 28, 1979). This hypothesis is that repeated ovulation cycles, each of which involves the disruption and repair of the ovarian surface epithelium, may cause neoplastic transformation of the ovarian epithelium in susceptible individuals and that the risk of ovarian cancer is positively associated with the number of ovulation cycles in a woman's lifetime.

There is no established pharmaceutical approach to the prevention of ovarian cancer. For all women, especially those at high risk of developing this disease, the only option available at this time is surgical removal of the ovaries, with all of the attendant risks and subsequent adverse health consequences due to resulting estrogen deficiency.

Although epidemiological evidence suggests that the use of combination oral contraceptives, which contain both an estrogen and a progestin, is associated with a subsequent reduced risk of developing epithelial ovarian cancer, the mechanism for this protective effect is unknown, and oral contraceptive preparations are not currently approved for this purpose. The reduction in risk of ovarian cancer in women who have used estrogen-progestin combination oral contraceptives for at least three years is approximately 40 percent. Moreover, this protective effect increases with the duration of use and persists for up to two decades after discontinuation of use. Rosenberg et al., *A Case Control Study of Oral Contraceptive Use and Invasive Epithelial Ovarian Cancer, The WHO Collaborative Study of Neoplasia and Steroid Contraceptives; Epithelial Ovarian Cancer and Combined Oral Contraceptives, Int'l J. Epidemiology* 18: 538–45, 1989; Lee et al., *The Reduction in Risk of Ovarian Cancer Associated with Oral Contraceptive Use, New Engl. J. Med.* 316: 650–51, 1987; Thomas P. Gross, James J. Schlesselman, *The Estimated Effect of Oral Contraceptive Use on the Cumulative Risk of Epithelial Ovarian Cancer, Obstetrics Gynecology* 83: 419–24, 1994; Franceschi et al., *Pooled Analysis of 3 European Case-Control Studies of Epithelial Ovarian Cancer: III Oral Contraceptive Use, Int'l J. Cancer* 49: 61–65, 1991.

It was commonly believed that the protective effect of oral contraceptives is related to the ability of these drugs to inhibit ovulation. Estrogen-progestin combination oral contraceptives act primarily by suppressing the pituitary gland's production of gonadotropins, thereby inhibiting the hormonal stimulus for ovulation. These combination drugs also have direct inhibitory effects on the reproductive tract, including inducing changes in the cervical mucus that decrease the ability of sperm to enter the uterus, as well as changes in the endometrium that reduce the likelihood of implantation, and reducing fallopian tube motility and uterine secretions.

The epidemiological studies showing the protective effect of combination oral contraceptives evaluated older combination preparations which typically contained higher doses of drug than most contraceptive regimens used today. Common older regimens contained 50 micrograms or more of ethinyl estradiol (an estrogen) or 100 micrograms or more of mestranol (an estrogen) and greater than 1 mg of norethindrone, norethindrone acetate or norethynodrel (progestins). Various combinations of progestin and estrogen that have been used in oral contraceptives are shown in Table 1.

TABLE 1

Trends In Combinations of Progestin and Estrogen

| Progestin | Dose (mg) | Norethindrone Equivalent Dose (mg) | Estrogen | EE Equivalent Dose (mg) | Dose (mg) | P/E Ratio |
|---|---|---|---|---|---|---|
| Nore-thynodrel | 9.85 | 9.85 | Mestranol | 0.150 | 0.105 | 93.810 |
| | 5.00 | 5.00 | | 0.075 | 0.053 | 95.238 |
| | 2.50 | 2.50 | | 0.036 | 0.025 | 99.206 |
| | 2.50 | 2.50 | | 0.100 | 0.070 | 35.714 |
| Nore-thindrone | 10.00 | 10.00 | Mestranol | 0.060 | 0.042 | 238.095 |
| | 2.00 | 2.00 | | 0.100 | 0.070 | 28.571 |
| | 1.00 | 1.00 | | 0.050 | 0.035 | 28.571 |
| | 1.00 | 1.00 | | 0.080 | 0.056 | 17.857 |
| Nore- | 1.00 | 1.00 | Ethinyl | 0.050 | 0.050 | 20.000 |

TABLE 1-continued

Trends In Combinations of Progestin and Estrogen

| Progestin | Dose (mg) | Norethindrone Equivalent Dose (mg) | Estrogen | EE Equivalent Dose (mg) | Dose (mg) | P/E Ratio |
|---|---|---|---|---|---|---|
| thindrone | 0.50 | 0.50 | estradiol | 0.035 | 0.035 | 14.286 |
| | 0.40 | 0.40 | (EE) | 0.035 | 0.035 | 11.429 |
| Nore-thindrone acetate | 2.50 | 2.50 | EE | 0.050 | 0.050 | 50.000 |
| | 1.00 | 1.00 | | 0.050 | 0.050 | 20.000 |
| | 0.60 | 0.60 | | 0.030 | 0.030 | 20.000 |
| | 1.50 | 1.50 | | 0.030 | 0.030 | 50.000 |
| | 1.00 | 1.00 | | 0.020 | 0.020 | 50.000 |
| Ethynodiol diacetate | 1.00 | 1.00 | Mestranol | 0.100 | 0.070 | 14.286 |
| Ethynodiol diacetate | 1.00 | 1.00 | EE | 0.050 | 0.050 | 20.000 |
| dl-Norgestrel | 0.50 | 2.00 | EE | 0.050 | 0.050 | 10.000 |
| | 0.30 | 1.20 | | 0.030 | 0.030 | 10.000 |

Equivalencies
50 mg Mestranol = 35 mg Ethinyl estradiol (EE)
0.5 mg dl-Norgestrel = 2 mg Norethindrone Each block describes a specific combination of progestin and estrogen, e.g., norethynodrel and mestranol, and within each block older combinations are listed first, with successively newer combinations following. Two trends are evident. First, over time the dosage of each component has decreased. Second, the downward trend of the progestin component is steeper than the downward trend of the estrogen component. On a relative scale, therefore, estrogen has become more important over time. With this downward trend in dosage, it is apparent that the relative ratio of progestin to estrogen is trending downward.

All of the currently used low-dose combination oral contraceptives contain lower doses of both progestin and estrogen, as well as a lower ratio of progestin to estrogen. Table 2 below lists the progestin and estrogen content of selected commercial regimens.

TABLE 2

Composition of Selected Currently Marketed Oral Contraceptives

| COMBINATION TYPE | | | | |
|---|---|---|---|---|
| | | μg | | mg |
| FIXED TYPE | | | | |
| Estrogen content = 50 μg: | | | | |
| Ortho-Novum 1/50 | Mestranol | 50 | Norethindrone | 1.0 |
| Norinyl 1/50 | Mestranol | 50 | Norethindrone | 1.0 |
| Ovcon 50 | Ethinyl estradiol | 50 | Norethindrone | 1.0 |
| Ovral | Ethinyl estradiol | 50 | Norgestrel | 0.5 |
| Damulen | Ethinyl estradiol | 50 | Ethynodiol diacetate | 1.0 |
| Norlestrin 2.5/50 | Ethinyl estradiol | 50 | Norethindrone acetate | 2.5 |
| Norlestrin 1/50 | Ethinyl estradiol | 50 | Norethindrone acetate | 1.0 |
| Estrogen content < 50 μg: | | | | |
| Ortho-Novum 1/35 | Ethinyl estradiol | 35 | Norethindrone | 1.0 |
| Norinyl 1 + 35 | Ethinyl estradiol | 35 | Norethindrone | 1.0 |
| Modicon | Ethinyl estradiol | 35 | Norethindrone | 0.5 |
| Brevicon | Ethinyl estradiol | 35 | Norethindrone | 0.5 |
| Ovcon 35 | Ethinyl estradiol | 35 | Norethindrone | 0.4 |
| Demulen 1/35 | Ethinyl estradiol | 35 | Ethynodiol diacetate | 1.0 |

TABLE 2-continued

Composition of Selected Currently Marketed Oral Contraceptives

| Loestrin 1.5/30 | Ethinyl estradiol | 30 | Norethindrone acetate | 1.5 |
| --- | --- | --- | --- | --- |
| Loestrin 1/20 | Ethinyl estradiol | 20 | Norethindrone acetate | 1.0 |
| Nordette | Ethinyl estradiol | 30 | Levonorgestrel | 0.15 |
| Lo-Ovral | Ethinyl estradiol | 30 | Norgestrel | 0.3 |
| Desogen | Ethinyl estradiol | 30 | Desogestrel | 0.15 |
| Ortho-cept | Ethinyl estradiol | 30 | Desogestrel | 0.15 |
| Ortho-cyclen | Ethinyl estradiol | 35 | Norgestimate | 0.25 |
| BIPHASIC TYPE | | | | |
| Ortho-Novum 10/11 | | | | |
| First 10 days | Ethinyl estradiol | 35 | Norethindrone | 0.5 |
| Next 11 days | Ethinyl estradiol | 35 | Norethindrone | 1.0 |
| TRIPHASIC TYPE | | | | |
| Ortho-Novum 7/7/7 | | | | |
| First 7 days | Ethinyl estradiol | 35 | Norethindrone | 0.5 |
| Second 7 days | Ethinyl estradiol | 35 | Norethindrone | 0.75 |
| Third 7 days | Ethinyl estradiol | 35 | Norethindrone | 1.0 |
| Tri-Norinyl | | | | |
| First 7 days | Ethinyl estradiol | 35 | Norethindrone | 0.5 |
| Next 9 days | Ethinyl estradiol | 35 | Norethindrone | 1.0 |
| Next 5 days | Ethinyl estradiol | 35 | Norethindrone | 0.5 |
| Triphasil | | | | |
| First 6 days | Ethinyl estradiol | 30 | Levonorgestrel | 0.05 |
| Second 5 days | Ethinyl estradiol | 40 | Levonorgestrel | 0.075 |
| Third 10 days | Ethinyl estradiol | 30 | Levonorgestrel | 0.125 |
| Tri-Levein | | | | |
| First 6 days | Ethinyl estradiol | 30 | Levonorgestrel | 0.05 |
| Second 5 days | Ethinyl estradiol | 40 | Levonorgestrel | 0.075 |
| Third 10 days | Ethinyl estradiol | 30 | Levonorgestrel | 0.125 |
| Ortho Tri-Cyclen | | | | |
| First 7 days | Ethinyl estradiol | 35 | Norgestimate | 0.18 |
| Second 7 days | Ethinyl estradiol | 35 | Norgestimate | 0.215 |
| Third 7 days | Ethinyl estradiol | 35 | Norgestimate | 0.25 |
| PROGESTOGEN ONLY | | | | |
| Micronor | None | | Norethindrone | 0.35 |
| Nor Q.D. | None | | Norethindrone | 0.35 |
| Ovrette | None | | Norgestrel | 0.075 |

It has not been definitively established by prior publications of others that the newer low-dose combination oral contraceptives are associated with the same protective effect as the older high-dose combination contraceptives. Rosenblatt et al., *High Dose and Low Dose Combined Oral Contraceptives: Protective Against Epithelial Ovarian Cancer and The Length of the Protective Effect, Eur. J. Cancer,* 28: 1870–76, 1992.

Despite the overall safety of combination oral contraceptives, their use is associated with increased risks in women smokers older than age 35, for women of all ages who are at increased risk for myocardial infarction, for women with liver disease, and for women older than age 40. Serious and potentially fatal side effects include deep vein thrombosis, pulmonary emboli, myocardial infarction, thromboembolic stroke, hemorrhagic stroke, and high blood pressure. In the 35–39 year old age group, the use of oral contraceptives among women smokers doubles their risk of death. After age 40, the mortality rate even in non-smoker women using oral contraceptives (32.0 per 100,000) is greater than in women using no contraception (28.2 per 100,000), while the mortality rate for smoker women is quadrupled (117.6 vs. 28.2 per 100,000). [Chapter 340, *Disorders of the Ovary and Female Reproductive Tract, Harrison's Principles of Internal Medicine,* pages 2017–2036.]

Progestin-only contraceptives do not reliably inhibit ovulation, but are nevertheless contraceptively effective, presumably due to direct effects on the reproductive tract. The actual contraceptive mechanism of action is unclear. Prior epidemiological studies have exhibited no consistent pattern of either increasing or decreasing risk of ovarian cancer according to duration of use. *The WHO Collaborative Study of Neoplasia and Steroid Contraceptives Depot-Medroxyprogesterone Acetate(DMPA) and Risk of Epithelial Ovarian Cancer, Int'l J. Cancer.* 49:191–195 (1991); Liam et al., *Risk of Breast, Uterine, Corpus, and Ovarian Cancer in Women Receiving/Medroxyprogesterone Injections, J. Am. Med. Ass'n* 249:2909–2912 (1983). Thus, unlike the data available for progestin-estrogen combination contraceptives, the available epidemiologic evidence relating to progestin-only contraceptives does not suggest that the use of a progestin reduces the risk of epithelial ovarian cancer. One epidemiologic study has suggested that hormone replacement therapy with estrogen alone may be associated with an increased risk of developing ovarian cancer. Rodriguez et al., *Estrogen Replacement Therapy and Fatal Ovarian Cancer, Am. J. Epidemiology,* 141:828–835 (1995).

Estrogen, alone or with low doses of progestin, is also used as hormonal replacement therapy in menopausal women. For long term use, Premarin (conjugated equine estrogen) is generally given at a dose of 0.625 mg orally daily (equivalent to 10 to 20 μg ethinyl estradiol orally per day) or an equivalent dose transdermally. Other regimens add cyclic progestins or continuous low-dose progestins, typically 2.5 to 10 mg per day of Provera (medroxyprogesterone acetate). Table 3 lists the estrogen contents (and other hormonal ingredients, where applicable) for various hormone replacement products.

TABLE 3

Estrogen Content of Common Hormone Replacement Regimens

| Name | Estrogen | mg | Other Hormone | mg | Regimen |
| --- | --- | --- | --- | --- | --- |
| Premarin (tablet) | Conjugated Estrogens | 0.3/ 0.625/ 0.9/ 1.25 2.5/ | — | — | 0.3–1.25 mg daily, administered continuously (daily, with no breaks) or days 1–25 of month |
| Premarin (cream) | Conjugated Estrogens | 0.625/1 g of cream | — | — | ½–2 g daily; 3 weeks on, 1 week off |

TABLE 3-continued

Estrogen Content of Common Hormone Replacement Regimens

| Name | Estrogen | mg | Other Hormone | mg | Regimen |
|---|---|---|---|---|---|
| Prempro (tablets) | Conjugated Estrogens | 0.625 | Medroxy-progesterone acetate | 5 mg or 2.5 mg | Continuous |
| Premphase (two types of tablets) | Conjugated Estrogens | 0.625 | Medroxy-progesterone acetate | 5 mg | Continuous |
| Days 1–14 | Yes | | No | | |
| Days 15–28 | Yes | | Yes | | |
| Estratest | Esterified Estrogens | 1.25 | Methyl-testosterone (Androgen) | 2.5 mg | 3 weeks on; 1 week off |
| Estratest H.S. | Esterified Estrogens | 0.625 | Methyl-testosterone (Androgen) | 1.25 mg | 3 weeks on; 1 week off |
| Estrace (tablets) | Estradiol | .5–2 | — | — | 3 weeks on; 1 week off |
| Climara (patch) | Estradiol (four different patches; dosages per day) | 0.025/ 0.051 0.0751 0.10 mg released per day | — | — | Continuous |

Vitamin D

The disclosure of Ser. No. 08/873,010, now issued U.S. Pat. No. 6,034,074, entitled Prevention Of Ovarian Cancer By Administration Of A Vitamin D Compound, is incorporated herein by reference. Vitamin D is a fat soluble vitamin which is essential as a positive regulator of calcium homeostasis. In the skin 7-Dehydrocholesterol (pro-Vitamin $D_3$) is photolyzed by ultraviolet light to pre-Vitamin $D_3$, which spontaneously isomerizes to Vitamin $D_3$. Vitamin $D_3$ (cholecalciferol), is converted into an active hormone by hydroxylation reactions occurring in the liver to produce 25-hydroxyvitamin $D_3$ which is then converted in the kidneys to produce 1,25-dihydroxyvitamin $D_3$ (1,25-dihydroxycholecalciferol, calcitriol, $1,25(OH)_2D_3$) which is transported via the blood to its classic target organs, namely, the intestine, kidney, and bones. Vitamin D deficiency in childhood produces rickets, which is characterized by inadequate calcification of cartilage and bone. In adults, Vitamin D deficiency leads to softening and weakening of bones, known as osteomalacia. The major therapeutic uses of Vitamin D are divided into four categories: (1) prophylaxis and cure of nutritional rickets, (2) treatment of metabolic rickets and osteomalacia, particularly in the setting of chronic renal failure, (3) treatment of hypoparathyroidism, and (4) prevention and treatment of osteoporosis. Recommended daily dietary allowances of Vitamin D by the Food and Nutrition Board of the United States National Research Council (1989) were 10 mg cholecalciferol (400 IU Vitamin D) daily for females age 11–24 and 5 mg cholecalciferol (200 IU Vitamin D) daily for females age 25 and older. Normal serum levels of 25-hydroxyvitamin $D_3$ are not closely regulated and it has a biological half-life of several weeks with blood levels typically ranging from 15 to 80 ng/mL. Serum levels of 1,25-dihydroxyvitamin $D_3$ are more closely regulated and typically range from 15–60 pg/mL. Serum 1,25-dihydroxyvitamin $D_3$ has a half-life of 6–8 hours. 1,25-dihydroxyvitamin $D_3$ partitions into cells by virtue of its lipophilicity, binds to intracellular receptors, and translocates to the nucleus where the complex controls the transcription of a number of genes, many of which relate to calcium metabolism. Corder et al., *Cancer Epidemiology, Biomarkers & Prevention* 2:467–472 (1993).

Certain compounds are known to upregulate the functional human Vitamin D receptor ("VDR"). For example, Santiso-Mere et al., *Molecular Endocrinology* Vol. 7, No. 7, pp.833–839 (1993) teach the expression of functional human vitamin D receptor (VDR) in *Saccharomyces cerevisiae*. This reference further teaches up-regulation of the VDR by 1,25-dihydroxyvitamin $D_3$. Davoodi et al.,*J Steroid Biochem. Molec. Biol.* 54: No. 3/4, pp. 147–153 (1995) relates to the effect of 1,25-dihydroxyvitamin $D_3$ on upregulation of the VDR. Davoodi et al. teach that progestins and trans-retinoic acid may also upregulate the VDR. Davoodi et al., at pp. 149–50.

Also of interest is the epidemiologic study of Lefkowitz et al., *International Journal of Epidemiology* vol 23, No. 6 pp 1133–1136 (1994) reporting that sunlight exposure may reduce the risk of ovarian cancer mortality. Using population based data regarding ovarian cancer mortality in large cities across the United States, as well as geographically based long-term sunlight data reported by the National Oceanic and Atmospheric Administration, the authors found an inverse correlation between regional sunlight exposure and ovarian cancer mortality risk. The publication refers to the antineoplastic effect of vitamin D against cancer cell lines and tumors as demonstrated in in vivo and in vitro studies and suggests that this anti-cancer cell effect may be reducing the ovarian cancer mortality rates for the regions with more sunlight. Thus, this study teaches that Vitamin D may have an effect on malignant cells. There is no teaching or suggestion that sunlight may have any effect on non-neoplastic cells or that the protective effect of sunlight may be mediated by an effect of enhanced levels of Vitamin D on non-neoplastic ovarian epithelial cells in vivo.

Studzinski et al., *Cancer Research* 55:4012–4022 (1995) also discuss the potential effect of Vitamin D from sunlight on retarding neoplastic progression of various cancers. Studzinski et al. refer to evidence that Vitamin D retards growth of cancer cells in vivo and in vitro, induces differentiation of cancer cells, and induces apoptosis in cancer cells, and that these effects may prevent cancer progression. Studzinski et al. do not suggest or imply that Vitamin D may have a preventative benefit through effect on non-malignant cells.

Thus, while the art prior to the work of applicant and his coworker reports various therapeutic activities of Vitamin D and its analogues and derivatives in retarding tumor growth, the effect of Vitamin D on ovarian carcinoma cells is unclear. Moreover there exists no suggestion that Vitamin D has activity in causing apoptosis in non-neoplastic cells or in inhibiting the conversion of non-neoplastic cells to neoplastic cells in any manner.

SUMMARY OF THE INVENTION

There remains a need in the art for methods and compositions which prevent cancers such as epithelial ovarian cancer by inhibiting the conversion of normal and dysplastic ovarian epithelial cells to neoplastic cells via biologic effects unrelated to ovulation inhibition. There is also a need to develop OCP and HRT regimens which are maximally protective against ovarian cancer. The present application, as well as the prior applications of applicant and applicant with a co-worker, address these needs.

The present invention provides a method for preventing the development of epithelial ovarian cancer by administering agents which promote TGF-$\beta$ expression in ovarian epithelial cells and/or which promote apoptosis of such cells, either alone or in combination with other agents, including other agents which increase apoptosis and/or induce increased TGF-$\beta$ expression. A method is provided of preventing ovarian cancer comprising administering to a female subject an amount of product effective to increase TGF-$\beta$ expression and/or apoptosis in ovarian epithelial cells of the female subject.

A method is provided for selecting the appropriate agent (s) through testing of candidate agents for TGF-$\beta$ response. In particular, human ovarian epithelial cells are treated in vitro with candidate agents and a measurement made for promotion of TGF-$\beta$ response. Based on these determinations, the agent(s) is used in a pharmacological dose for maximally reducing the risk of ovarian cancer.

Pharmaceutical compositions and regimens are provided for prevention of ovarian cancer which comprises HRT and OCP formulations with the addition of an agent which increases TGF-$\beta$ expression in the ovarian epithelium. A method of reducing the risk of ovarian cancer through the administration of such pharmaceutical compositions is also contemplated by the present invention. This invention also contemplates compositions comprising the hormonal products found in the prior HRT and OCP formulations, but in dosages and schedules that maximize upregulation of TGF-$\beta$ in the ovarian epithelium and which confer maximal protection against ovarian cancer.

It is further the object of this invention to expand the clinical usage of progestin drugs beyond the current use of these drugs as oral contraceptive agents in young women or as part of estrogen-progestin hormone replacement regimens in postmenopausal women. One aspect of the invention provides a method for preventing the development of ovarian cancer comprising administering to a female subject a composition consisting essentially of a progestin product (i.e., a progestin product alone without an estrogen product) or comprising a progestin product in the absence of an estrogen.

The invention also provides a method for preventing the development of ovarian cancer comprising administering a progestin product to a female subject according to a regimen that is not effective for contraception. This can be accomplished in a number of ways, including altering the dosage of progestin product, the type of progestin product, the ratio of progestin product to estrogen product, or the timing of administration.

With regard to infertile female subjects, the present invention further provides a method for preventing the development of ovarian cancer comprising administering products according to a regimen that is different from that currently used for hormone replacement therapy and/or OCP use. Again, this can be accomplished in a number of ways, including altering the dosage, timing, ratio of progestin product to estrogen product, or the type of progestin product, or by addition of other agents which induce increased TGF-$\beta$ expression in ovarian epithelial cells and/or induce apoptosis in ovarian epithelial cells.

It is contemplated that the preventive product useful for the composition of this invention includes any product that increases TGF-$\beta$ expression. These products could include progestins, estrogens, androgens, androgen antagonists, progestin antagonists, estrogen antagonists, or other agents including those selected from the group consisting of the retinoids, dietary flavanoids, anti-inflammatory drugs, monoterpenes, S-adenosyl-L-methionine, selenium and vitamin D compounds. One embodiment of the invention comprises combining progestins with one or more of the above-mentioned compounds. The additional agent(s) used with the progestin may be selected to improve the activity of the progestin agent for preventing ovarian cancer or to reduce any side effects of the progestin agent. Preferably if estrogen is used as the second agent, it is used in doses lower than those currently used in combination OCP regimens or in doses selected to provide a progestin/estrogen product ratio that is higher than the ratio currently used in combination OCPs. Similarly, if estrogen is used as the second agent for a HRT formulation, then it is preferably used in estrogenic doses lower than those currently used in HRT regimens, or in doses selected to provide a progestin/estrogen product ratio that is higher than the ratio currently used in HRT regimens. Alternatively, the compositions can include estrogens having antiestrogenic activity, particularity in breast tissue.

The present invention is based on the discovery that administration of progestin induced increased TGF-$\beta$ expression in vivo in the ovarian epithelial cells of monkeys, and that the increased TGF-$\beta$ expression was highly correlative with apoptosis. Apoptosis is one of the most important mechanisms used for the elimination of cells that have sustained DNA damage and which are thus prone to transformation into malignant neoplasms. TGF-$\beta$ is an important regulator of apoptosis. Therefore, the association between estrogen-progestin combination oral contraceptive use and a reduced risk of ovarian cancer may be explained by the progestin's ability to upregulate TGF-$\beta$ expression. This is a departure from the widely accepted theory that suppression of "incessant ovulation" is responsible for this reduced risk.

The invention thus contemplates that administration of progestin alone can be effective for preventing the development of ovarian cancer, contrary to suggestions that progestin has no effect on risk of ovarian cancer. In addition to providing the use of high dosages of progestin products, high potency progestin products and/or high ratios of progestin products to estrogens in promoting TGF-$\beta$ expression of ovarian epithelial cells to prevent ovarian cancer, the invention provides the use of other TGF-β and/or apoptosis promoting agents, including agents selected from the group consisting of the retinoids, dietary flavanoids, anti-inflammatory drugs, monoterpenes, S-adenosyl-L-methionine, selenium and vitamin D compounds to promote TGF-β expression and/or apoptosis in ovarian epithelial cells.

This discovery opens up the possibility of developing pharmacological approaches available to women of all ages to reduce the risk of ovarian cancer by selection of one or more agents which upregulate TGF-β expression in ovarian epithelial cells.

DETAILED DESCRIPTION OF THE INVENTION

The present invention generally relates to methods for preventing the development of epithelial ovarian cancer by administering one or more TGF-β inducing agents.

As discussed in the applicant's prior application Ser. No. 08/713,834, incorporated herein by reference, the applicant discovered that administration of progestin alone induced a marked increase in apoptosis in vivo in the ovarian epithelial cells of monkeys. Apoptosis is a process whereby a genetic program within the cell is activated to trigger a specific series of events within the cell eventually leading to the death and efficient disposal of the cell. Richard Lockshin, Zahra Zakeri, *The Biology of Cell Death and Its Relationship to Aging in Cellular Aging and Cell Death*, pp. 167–180, 1996. Wiley-Liss Inc., Editors: N. J. Holbrook, G. Martin, R. Lockshin. C. Miligan, L. Schwartz, *Programmed Cell Death During Development of Animals in Cellular Aging and Cell Death*, pp. 181–208, 1996. Wiley-Liss Inc. P53-Dependent *Apoptosis in Tumor Progression and in Cancer Therapy*, Scott W. Lowe, H. Earl Ruley in *Cellular Aging and Cell Death*, pp. 209–234, 1996. Wiley-Liss, Inc.

For cells that have sustained DNA damage, apoptosis is one of the most important mechanisms used for the elimination of these cells, the preservation of which could otherwise lead to the development of malignant neoplasms. Canman et al., *DNA Damage Responses: P-53 Induction, Cell Cycle Pertubations, and Apoptosis, Cold Spring Harbor Symp. Ouant. Biol.*, 59:277–286 (1994). Thus, the apoptosis pathway is a virtually universal safeguard to prevent the persistence and proliferation of damaged cells that can be lethal to the organism. For normal tissues, the processes of cell proliferation and cell death are usually in a steady-state balance, and the apoptosis mechanism not only serves to prevent overgrowth of tissue, but also to eliminate those cells that are aberrant and therefore prone to resist normal growth regulatory controls.

An accelerated rate of apoptosis would facilitate the destruction and thereby removal of ovarian surface epithelial cells which have defective DNA and which have the potential to transform into cancer. Given the importance of the apoptotic pathway for removal of abnormal cells from tissues, and thus the protection of normal tissues from neoplastic transformation, it is likely that the induction of apoptosis by progestins is one of the major (if not the major) mechanisms underlying the effect of combination oral contraceptives in reducing the risk of ovarian cancer.

This novel explanation for the association between estrogen-progestin combination OCP use and a reduced risk of ovarian cancer is a complete departure from the widely accepted theory that suppression of "incessant. ovulation" is responsible for this reduced risk. This finding thus leads to the discovery that progestin alone or estrogen-progestin combinations may be administered in ways that do not effectively inhibit ovulation or otherwise inhibit contraception, yet which still prevent ovarian cancer. Since the protective mechanism for progestin containing compounds is related to a direct biological effect on the ovarian epithelium, it is likely that the use of progestin drugs in postmenopausal women who are not ovulating will also be protective against the development of epithelial ovarian carcinoma.

The invention is further based on the discovery that use of progestin alone induced more apoptosis in vivo in ovarian epithelial cells of monkeys than the combination of estrogen and progestin, which in turn induced significantly more apoptosis than estrogen alone. The implications of this discovery are that the progestin component of the oral contraceptive is responsible for this effect, and that administration of progestin alone may be effective for preventing the development of ovarian cancer, contrary to established reports that it has no effect on risk of ovarian cancer. Since the human-equivalent dose of the progestin only dose given the monkeys is insufficient to reliably block ovulation in women, yet showed the greatest degree of apoptosis (and thus protection), this indicates that ovulatory blockade per se is not essential for the protective effect, and that progestin product only (or with estrogen product) in doses less than sufficient to prevent ovulation is effective in preventing ovarian cancer. A further implication of this discovery is that estrogens may decrease the ovarian cancer protective effects of progestins, and that combination estrogen/progestin regimens that have either weak estrogens or anti-estrogens may be more protective against ovarian cancer than comparable regimens containing a strong estrogenic component.

Transforming Growth Factor Beta

The present application is based further on the discovery that administration of progestin induced increased TGF-β expression in the ovarian epithelium in primates and that the degree of expression was highly correlative with apoptosis. See Example 1 set forth below in this application for a description of the test leading to this initial discovery.

The regulation of apoptosis is complex, and influenced by numerous families of transcriptional factors, tumor suppressor genes, and oncogenes. Recently, TGF-β has been shown to be of prominent importance in the regulation of apoptosis. TGF-β has been implicated in the apoptotic pathway of a variety of cell types. Correlation between the degree of TGF-β expression and apoptosis has been shown in tissues such as the breast and prostate, and the apoptotic activity of hormones such as the retinoids has been shown to be mediated at least in part through the activity of TGF-β. Interestingly, multiple members of the steroid hormone superfamily including the retinoids, vitamin D, and estrogens have been shown to modulate expression of TGF-β, and the promoter region for specific TGF-β isotypes such as TGF-β3 contains features suggesting hormonal regulation.

Accordingly, TGF-β may play a role in the prevention of epithelial ovarian cancer through induction of apoptosis in ovarian epithelial cells or through some other biologic mechanism or through some combination thereof.

The TGF-β family of molecules is part of a larger family of cytokines that exert a wide range of biologic effects on a variety of cell types and tissues. At least five TGF-β molecules have been characterized (TGF-β's 1–5). Of these, only three major isoforms of TGF-β, TGF-β-1, -2, and -3 have been identified in mammalian systems. These three isoforms are highly homologous, and localized to three different chromosomes (19q13, 1q41, and 14q24, respectively). In addition, placental TGF-β has also been recently isolated.

The Transforming Growth Factor Beta superfamily consists of a large group of over forty related peptide growth and differentiation factors, including the TGF-β isoforms, the bone morphogenetic proteins ("BMP"), activins/inhibins, decapentaplegic product, as well as Mullerian inhibitory substance ("MIS"). J. Taipale, et al., in "Extracellular Matrix-Associated Transforming Growth Factor-β: Role in Cancer Cell Growth and Invasion," describe portions of the TGF-β superfamily as follows: "The BMP family includes the bone morphogenetic proteins (BMPs 2–7), growth and differentiation factor-1 (GDF-1), and Drosophilia decapentaplegic (dpp) Xenopus Vgl, and dorsalin-1 (Massagué et al., 1994; Basler et al., 1993). Multiple members of the BMP family have key roles in bone morphogenesis and epithelial-mesenchymal interactions during embryonic pattern formation (Kingsley, 1994). The activin family consists of activin A and activin B. Activins regulate the secretion of pituitary follicle-stimulating hormone (FSH). The MIS family includes Muüllerian inhibiting substance, which mediates Muüllerian duct regression in male embryos. The rather specific functions of the TGF-β superfamily proteins are reflective of the purification and cloning strategies used, and a large number of other effects are likely to be assigned to many of the individual members. Multiple new TGF-β superfamily members have been cloned that are difficult to assign to the above subfamilies. Therefore, a more open classification has been suggested based on a continuum of homologous factors, forming defined clusters with close homologs (Massagué et al., 1994) (FIG. 2)." In J. Massagué, "TGF-β Signal Transduction," the TGF-β family is described as follows: "Based on sequence comparisons between the bioactive domains, the TGF-β family can be ordered around a subfamily that includes mammalian BMP2 and BMP4 and their close homologue from Drosophilia, Dpp. All other known family members progressively diverge from this group, starting with the BMP5 subfamily, followed by the GDF5 (growth and differentiation factor 5) subfamily, the Vg1 subfamily, the BMP3 subfamily, various intermediate members, the activin subfamily, the TGF-β subfamily, and finally several distantly related members (Table 1) (1–17)."

Transforming Growth Factor Beta is a potent growth inhibitor of a variety of cell types including epithelial cells. It is therefore essential for maintenance of epithelial homeostasis. During the process of neoplastic transformation, tumor cells often become resistant to TGF-β thereby removing a natural growth inhibitor and allowing continual proliferation. In addition to the inhibitory effects of TGF-β on cell growth, it has numerous other effects including effects on cellular differentiation, adhesion, extracellular matrix deposition, and programmed cell death (apoptosis). There is strong evidence in support of the concept that TGF-β is a potent tumor suppressor. Inactivation of the TGF-β pathway is a common finding in human tumors.

The transcriptional regulation of TGF-β is just now beginning to be elucidated. The promoter for TGF-β-1 contains multiple regulatory cites that can be activated by numerous early genes, oncogenes as well as viral transactivating proteins. The TGF-β-1 promoter is suppressed by various tumor suppressor genes, including the products of the retinoblastoma gene. In contrast, the promoters for TGF-β-2 and 3 contain features suggesting hormonal and developmental control. For example, a Raloxifene response element has been described on the TGF-β-3 promoter. Multiple members of the steroid hormone superfamily modulate expression of TGF-β including the retinoids, vitamin D, and estrogens (in particular, estrogens having antiestrogenic activity such as Tamoxifen and Raloxifene).

The availability and bioactivity of TGF-β is highly regulated. TGF-β is secreted from cells in the form of a latent complex, which is then sequestered by the extracellular matrix and activated by a variety of mechanisms including the plasminogen activator proteolytic pathway. The activity of TGF-β is mediated through the TGF-β receptors, which are transmembrane serine/threonine kinases designated Type 1 and Type 2. These receptors share significant homology. Upon binding of a divalent TGF-β molecule to the Type 2 receptor, the Type 2 receptor phosphorylates the Type 1 receptor. The Type 1 receptor in turn activates the Smad proteins, which then translocate the signal to the nucleus, where the signal is transcribed, and downstream genes are activated, leading to a specific cellular response. The TGF-β and Vitamin D signaling pathways may be converging through a common Smad signaling molecule (Smad 3). TGF-β signaling enhances the Vitamin D signal. Yanagisawa, et al., Convergence of Transforming Growth Factor-β and Vitamin D Signaling Pathways on SMAD Transcriptional Coactivators, Science, Vol. 283, pp. 1317–21.

The available experimental evidence suggests that TGF-β can play opposite roles with respect to the process of cancer progression: early on, TGF-β functions as a potent tumor suppressor, whereas in advanced tumors, TGF-β enhances tumor growth and metastatic potential. The switch from a tumor suppressor to tumor enhancer is probably associated with the acquisition of aberrations in the TGF-β signaling pathway, ranging from defects in TGF-β receptors, to mutations in the genes that encode for the Smad proteins that transfer the TGF-β signal from the cell membrane to the nucleus. In the absence of growth inhibitory effects of TGF-β, the stimulatory effects of TGF-β on matrix deposition and angiogenesis become prominent, thereby conferring a growth advantage to tumor cells.

Fortunately, disregulation of the TGF-β pathway is thought to be a late event in carcinogenesis. This has significant implications for the chemoprevention of cancer, in that agents that induce or activate TGF-β may confer chemopreventive effects when given to individuals who are at risk for but do not yet have cancer. Indeed, well known chemopreventive agents such as the retinoids and the antiestrogen Tamoxifen, which confer protection against cancers of upper aero-digestive tract and breast, have been demonstrated to induce TGF-β in these organs.

Accordingly, it is contemplated that TGF-β could confer protection against epithelial ovarian cancer through one of the following mechanisms or a combination thereof: (1) inhibition of proliferation of ovarian epithelial cells; (2) induction of differentiation in ovarian epithelial cells; (3) activation of or enhancement of the protective effects of other agents such as Vitamin D; and (4) apoptosis of ovarian epithelial cells. It is contemplated that a combination of agents that act at different points in the TGF-β pathway could have additive or synergistic effect that lead to maximal prevention of ovarian epithelial cancer. Furthermore, it is contemplated that the optimal protective effects of TGF-β against ovarian cancer would occur in the setting where no cancerous cells are present in the ovarian epithelium. Thus, one aspect of the invention involves first confirming that a female subject has no indication of cancer or cancerous cells in the ovarian epithelium, and then after such confirmation administering to the subject with one or more of the regimens of this invention.

Unless otherwise indicated (for example, by using the phrase "TGF-β isoforms"), the term "TGF-β" as used herein refers to the molecules in the TGF-β superfamily. The invention further contemplates introducing one or more molecules in TGF-β superfamily to induce one or more of the effects in the ovarian epithelium mentioned in the above paragraph. One aspect of the invention contemplates direct introduction of TGF-β molecules into the patient. Another aspect of the invention contemplates increasing the amount of TGF-β molecules by introduction of other compositions which in turn increase of the amount of TGF-β molecules.

This invention contemplates delivering TGF-β through direct delivery systems, such as a smart liposome system. For example, one or more TGF-β isoforms, such as TGF-β-1 (or alternatively any other TGF-β isoforms, including 2, 3, 4, 5 and/or placental TGF-β) is packaged in a liposome with a lock and key mechanism to deliver the TGF-β to the ovarian surface. The liposome can be also equipped with a lock and key mechanism so that the TGF-β can be delivered in addition or in the alternative to other organs such as the uterus, if desired. For example, the liposome could have an antibody which is designed to uniquely bind to the ovarian surface and/or any other organ surfaces. The liposome can also have other antibodies that allow it to bind to other surfaces such as the uterus.

Various Embodiments Of The Invention

The invention provides a method of preventing ovarian cancer comprising administering to a female subject an amount of a product effective to increase TGF-β expression in ovarian epithelial cells of the female subject. The invention also provides a method of administering to a female subject an amount of progestin product effective to increase TGF-β expression in ovarian epithelial cells of the female subject. The methods of the present invention will be particularly advantageous when applied to females at high risk of developing ovarian cancer. As a further aspect of the invention it is contemplated that the methods and regimens of doses of the present invention which use high dosages of progestins, high potency progestins and/or high ratios of progestins to estrogens may be effective in preventing not only ovarian cancer, but also the occurrence of endometrial cancer.

The term "progestin," "progestin product" or "progestogenic agent" as used herein in the descriptions of the various embodiments of the invention includes any drug which binds to the progestin receptor and induces a progestational effect. This definition thus includes all of the known progestins, derivatives of progesterone or testosterone that have progestin activity, and progestin antagonists having a progestational effect. It is contemplated that not only presently available progestins but also progestins introduced in the future will be useful according to the present invention. The progestins that are clinically useful for this invention comprise (a) the naturally occurring 21-carbon steroid, specifically progesterone itself and 17-hydroxyprogesterone and their derivatives; (b) the 21-carbon progesterone derivatives, specifically medroxyprogesterone, and megestrol; and (c) the 19-nortestosterone and its derivatives such as norethindrone and norgestrel. The known synthetic progestins are mainly derivatives of 17-alpha-hydroxyprogesterone or 19-nortestosterone. These progestins can be classified into three groups: the pregnane, estrane, and gonane derivatives. The pregnane progestins, derived from 17-alpha-hydroxy-progesterone, include, for example, medroxyprogesterone acetate, chlormadinone acetate, megestrol acetate, and cyproterone acetate. These are generally 20% to 50% of the potency of norethindrone. The estranes, derived from 19-nortestosterone include norethindrone, norethynodrel, norethinodryl, lynestrenol, norethindrone acetate, ethynodiol diacetate, and norethindrone enanthate. All of these are metabolized to norethindrone and are roughly equivalent to the same dosage of norethindrone. The gonanes are derived from the basic estrane structure, with the addition of an ethyl group of position 13 of the molecule. This additional ethyl group confers augmented progestogenic activity, and also significant androgenic effects. Drugs in this group include, for example, norgestrel (-d and -l), norgestimate, desogestrel, and gestodene. All of these are roughly equivalent to four times the dose of norethindrone. The progestins further include dehydrogestrone; desogestrel; 3-ketodesogestrel; dienogest; norethisterone; norethisterone acetate; progesterone; trimegestone; 19-nor-17-hydroxy progesterone ester; D-17β-acetoxy-13β-ethyl-17α-ethinyl-gon-4-en-3-one oxime; 17-hydroxyprogesterone esters and 19-nor-17-hydroxyprogesterone esters, 17α-ethinyltestosterone, 17α-ethinyl-19-nortestosterone and derivatives thereof; 17-hyroxyprogesterone, 17-hydroxyprotesterone esters, 19-nor-17-hydroxyprogesterone, 19-nor-17-hydroxyprogesterone esters, 17α-ethinyltestosterone, 17α-ethinyl-19-nortestosterone, d-17β-acetoxy-13β-ethyl-17α-ethinyl-17β-hydroxygon-4-en-3-one, 13β-ethyl-17β-hydroxygon-4-en-3-one, 13β,17α-diethyl-17β-hydroxygon-4-en-3-one, chlormadione acetate, dimethistrone, 17α-ethinyl-β-acetoxy-19-norandrost-4-en-3 one oxime, 3-ketodesogestrel, desogestrel, gestodene, and gestodene acetate.

Progestogenic agents have a variety of biological effects including antifertility, inhibition of midcycle luteinizing hormone surge, inhibition of ovulation, inhibition of corpus lutetium function and development, and production of a secretory endometrium. In addition, the progestins have important effects on carbohydrate metabolism, lipid and lipoprotein metabolism and have cardiovascular effects.

Progestogenic potency can be measured by other biological outcomes, including the ability of these agents to bind to the progesterone receptor. The progestogenic activity of the various progestin derivatives can vary. In a review of the literature, Dorflinger has noted that the progestogenic potency of all these estrane drugs is equivalent, and exhibit only 5–10 percent of the progestogenic activity of levonorgestrel.

In addition to their progestogenic effects, the synthetic progestins have the ability to bind to both estrogen and androgen receptors, to a varying degree. These drugs can therefore have estrogenic, androgenic, antiestrogenic or antiandrogenic effects. For example, the estrane progestins are weak estrogen agonists, and therefor have slight estrogen activity. In contrast, the gonane levonorgestrel has no estrogenic activity, but does have androgenic activity. The 19-nortestosterone derivatives have androgenic activity mediated by variable binding to the androgen receptor.

Given the diverse binding patterns of the different synthetic progestins to various receptors (progestin, androgen and estrogen receptors), the estrogenic, progestogenic and androgenic activity can vary among the different synthetic progestin formulations, thus leading to varying degrees of progestational activity and androgenic side effects. For example, the progestational binding activity of norethindrone is less than 20% that of levonorgestrel and less than 10% that of 3-ketodesogestrel, the active metabolite of the progestin desogestrel, while the binding affinity of norethindrone to the androgen receptor is similar to that of 3-ketodesogestrel, and yet both compounds have less than 50% of the nuclear cell androgenic activity of levonorgestrel.

It is contemplated that the progestins with more androgenic activity and less estrogenic activity, such as levonorgestrel, may be preferred as more potent for preventing the development of ovarian cancer, including in the OCP and HRT regimens of this invention described herein. Such agents would include the 19-nortestosterone derivatives, such as norethindrone, norethynodrel, lynestrenol, norethindrone acetate, ethynodiol acetate, and norethindrone enanthate.

Table 4 below shows the bioeffects of some progestins where the quantity of progestin is held constant (i.e., effect per mg of progestin). The table is reproduced from *Principles and Practice of Endocrinology and Metabolism, Second Edition*, Chapter 102.

TABLE 4

EXTENT OF VARIOUS BIOEFFECTS OF PROGESTINS

| EFFECT | STRONG | WEAK |
| --- | --- | --- |
| ANDROGENIC | Norgestrel | Ethynodiol diacetate |
|  | Levonorgestrel | Norethindrone |
|  | Norethindrone acetate | Desogestrel |
| ESTROGENIC | Norethynodrel | Gestodene |
|  | Etnynodiol diacetate | Norgestimate |
|  | Norethindrone | Levonorgestrel |
| ANTIESTROGENIC | Norethindrone acetate | Norethindrone diacetate |
|  | Norgestrel | Norethindrone |
|  | Levonorgestrel | Ethynodiol diacetate |
|  | Desogestrel |  |
|  | Gestodene |  |
|  | Norgestimate |  |
| PROGESTATIONAL | Norgestrel |  |
|  | Levonorgestrel |  |
|  | Norethindrone |  |
|  | Norethindrone acetate |  |
|  | Ethynodiol diacetate |  |
|  | Norethynodrel |  |
|  | Desogestrel |  |
|  | Gestodene |  |
|  | Norgestimate |  |

Table 4 shows that various progestin have higher antiestrogenic effect. This invention contemplates that the progestins classified in Table 4 as "strong" for antiestrogenic effect (as well as other progestins having antiestrogenic strength at least as high as one or more of these progestins) are preferred progestins for this invention, including the OCP and HRT regimens described herein. The progestins classified as "strong" for progestational effect (as well as other progestins having progestational effect at least as high as one or more of those classified progestins) are also preferred progestins for this invention, including the OCP and HRT regimens described herein. Progestins classified as "strong" in both categories (as well as other progestins having progestational and antiestrogenic activity at least as high as one or more of such classified progestins) are also preferred, including for the OCP and HRT regimens described herein. Progestins classified as "strong" in androgenic effect in Table 4 (as well as other progestins having androgenic effect at least as high as one of those classified progestins) are also preferred for an aspect of this invention including for the OCP and HRT regimens described herein.

The term "upregulating agent which binds to the progestin receptor" includes any compounds which bind to the progestin receptor and further induces upregulation of TGF-β response and/or apoptosis in the ovarian epithelium. It is contemplated that an upregulating agent which binds to the progestin receptor, including such agents which induce no progestational effect, can be used in any of the regimens described herein (including HRT and OCP regimens) in addition to the agents described for each such regimen. It is contemplated that an upregulating agent which binds to the progestin receptor, including such agents which induce no progestational effect, can be used in lieu of the progestin identified in the regimens described herein, including the OCP and HRT regimens. It is preferred that the upregulating agent which binds to the progestin receptor induces upregulation of TGF-β response and/or induces apoptosis in the ovarian epithelium at a rate per mg at least as high as compared to levonorgestrel.

The term "estrogen" and "estrogen product" as used herein includes natural estrogens such as estrone, estrone sulfate, estrone sulfate piperazine salt, estradiol and estriol, and their esters, as well as ethinyl estradiol, mestranol (a 50 mg dosage of which is equivalent to 35 mg of ethinyl estradiol), conjugated equine estrogen, esterified estrogens, estropipate, 17α-ethinylestradiol, esters and ethers of 17α-ethinylestradiol such as, for example, 17α-ethinylestradiol 3-dimethylamino propionate, 17α-ethinylestradiol 3-cyclopentyl ether (quinestrol) and 17α-ethinylestradiol 3-methyl ether (mestranol), estradiol-17beta, estradiol valerate, piperazine estrone sulphate, estriol succinate, and polyestrol phosphate and other estrogen equivalents and estrogen agonists and antagonists (but, as is commonly understood in the art, does not include progestins (even progestins having estrogenic activity)).

In one aspect of the invention, a method is provided for preventing the development of ovarian cancer comprising administering to a female subject a composition consisting essentially of a progestin product (i.e., a progestin product alone without an estrogen product) or a composition comprising a progestin product with other active agents, but in the absence of an estrogen. The female subject may be a fertile female or an infertile female, including perimenopausal and postmenopausal women. The most preferred product for administration would be an agent that provides the greatest rate of TGF-β response in ovarian epithelial cells with the least side effects, and/or the greatest rate of apoptosis of ovarian epithelial cells with the least side effects. Use of a progestin product for longer durations, or at higher doses, at appropriate intervals, and/or use of an agent that maximizes TGF-β expression in ovarian epithelial cells and/or apoptosis, without creating unacceptable side effects, in fertile or infertile women may reduce the risk of ovarian cancer further than that previously achieved by combination oral contraceptive use.

Another aspect of the present invention contemplates expanding the clinical usage of progestin drugs beyond the current use of these drugs as oral contraceptive agents in young women or as part of estrogen-progestin hormone replacement regimens in postmenopausal women. In addition, methods are provided for preventing the development of ovarian cancer comprising administering a progestin product to a fertile female subject both according to regimens that are effective for contraception and according to regimens that are not effective for contraception. This can be accomplished in a number of ways, including altering the dosage of progestin product, the type of progestin product, the ratio of progestin product to estrogen product, or the timing of administration. Also specifically contemplated is administration of a progestin product in doses higher than those currently used for contraception. In addition, other TGF-β inducing agents and/or apoptosis-inducing agents can be added to the OCP formulations to enhance their ovarian cancer preventive effect.

Oral contraceptive administration regimens are selected to simulate the normal menstrual cycle, which averages 28 days in women of reproductive age. The menstrual cycle begins at the onset of a menstrual bleeding episode and lasts until the onset of the next. Thus, day 1 of a cycle would be the first day of menstruation, and day 28 would be the day before the onset of the next menstrual bleeding episode. Oral contraceptives are typically taken daily, at the same time each day, for 21 days, followed by a placebo for the next 7 days. The female generally experiences a menstrual bleeding episode during the seven-day placebo period. Thus, a woman first starting on oral contraceptives is generally instructed to begin taking them at some time between day 1 and 7.

The oral contraceptives must be taken according to the daily regimen for a full menstrual cycle before they are effective for contraception. A woman beginning an oral contraceptive regimen is not effectively protected against conception if the oral contraceptives are taken for less than the full menstrual cycle, if they are not taken daily, and if they are not taken for 21 consecutive days. A minimum blood level of the exogenously administered estrogen or progestin hormones must be maintained daily in order to suppress ovulation. If the blood level drops too low, ovulation may occur and the other inhibitory mechanisms on the reproductive tract may fail to prevent conception.

According to another aspect of present invention, a regimen of progestin product administration that is not effective and/or not intended for contraception would include, for example, administering or delivering (regardless of whether the route of administration is oral or via injection or implant) progestin products in doses lower than those effective for contraceptive use and/or lower than those previously used in contraceptives; administering progestin products with estrogen products at a progestin/estrogen ratio that is higher than that previously used in contraceptives; administering the drug for less than one menstrual cycle; administering the drug for nonconsecutive menstrual cycles, e.g., every other cycle; administering the drug for one or more menstrual cycles for fewer than 21 consecutive days in each cycle; delivering the drug (regardless of whether the route of administration is oral or via injection or implant) with a less than daily frequency; or administering the drug for one or more menstrual cycles according to a regimen that fails to maintain a contraceptive blood level of the drug or its active metabolite for 21 consecutive days in each cycle. A regimen of progestin product administration that is different from that currently used for contraception would also include administering the progestin product at a daily dose higher or at a higher dose per unit of time than that currently used for contraception. A unit of time could consist of one day, one to three days, as many as five days, 5 days to two weeks, two to four weeks, or one to three months or longer. Exemplary regimens according to this aspect of the invention include administering progestin product at a dose equal to or greater than 2.5 mg daily, equal to or higher than 5 mg daily, or equal to or higher than 10 mg daily of a norethindrone equivalent dose. Another exemplary regimen includes administering progestin product at a dose less than a dose equivalent to 1 mg daily of norethindrone, more preferably less than 0.2 mg daily, or less than 0.05 mg daily, and possibly as low as 0.025 mg daily of a norethindrone equivalent dose. A further exemplary regimen includes administering a progestin product with an estrogen product at a ratio of greater than 50:1 by weight in norethindrone/ ethinyl estradiol equivalent doses with a ratio greater than 100:1 or 239:1 by weight being preferred ratios. Additional exemplary regimens include administering any dose of progestin product with a less than daily frequency; or administering any dose of progestin product for a brief time, e.g., one week only, during the menstrual cycle.

It is contemplated that the most desirable mode of administration may be administering the progestin product for a brief period sufficient to induce TGF-$\beta$ expression and/or produce apoptotic turnover of damaged ovarian cells, followed by repeated dosing periods at intervals, for example monthly, two to six times per year or every 1, 3, 5 or 10 years, selected to provide apoptotic turnover adequate to prevent malignant transformations. The most preferable progestin product for administration would be a product that maximizes TGF-$\beta$ expression and/or the apoptotic turnover of ovarian epithelial cells and minimizes any side effects.

This invention further includes a method for preventing the development of ovarian cancer comprising administering a TGF-$\beta$ inducing agent in an OCP regimen which is effective for contraception. Thus, this invention contemplates that regimens known to be effective for contraceptive use, including the regimens and formulations discussed in the text and tables of the background section of this application, are modified to include a second progestin (preferably one having progestational effect per mg at least as high as one or more of the progestins listed as "strong" in this category in Table 4and/or having antiestrogenic effect per mg at least as high as one or more of the progestins listed as "strong" in this category in Table 4 and/or having androgenic effect per mg at least as high as one or more of the progestins listed as "strong" in that category in Table 4), a Vitamin D component, or any other TGF-$\beta$ inducing agent. The agent can be put in one or more of the pills on the OCP regimen, including the otherwise placebo pills or pills containing hormones.

One embodiment of this invention further contemplates the use, in any of the formulations discussed herein, including OCP regimens, of progestins having progestational activity per mg at least as high as one or more of the progestins listed as "strong" in this category in Table 4. Further, the progestins having progestational activity as high as such listed progestins in uterine and ovarian epithelium tissues can be preferred in this aspect of the invention. Further, the progestins having antiprogestational activity with respect to the breast tissues can be another preferred aspect of this invention. Such progestins are useful for any of the OCP regimens described herein either as the sole progestin or as a second progestin added to one or more of the daily dosages in an amount sufficient to protect the breast tissues. When used as a second progestin in a regimen, the dosage of the second progestin is provided in one embodiment at a dosage equivalent of at least 0.125 mg of levonorgestrel, alternatively at least 0.25, alternatively at least 0.5, and alternatively at least 1.0, and alternatively at least 2.0, or alternatively at least 3.0 or more. (Preferably, the OCP regimens utilize a progestin having a progestational effect per mg as strong as levonorgestrel and/or an antiestrogenic effect per mg as strong as levonorgestrel.)

Further, the invention contemplates the use, in any of the formulations discussed herein, including OCP regimens, of progestins having antiestrogenic effect per mg at least as high as one or more of the progestins listed as "strong" in that category in Table 4. Particularly, progestins having antiestrogenic activity with respect to the ovarian epithilium and/or antiestrogenic activity with respect to the uterus and/or antiestrogenic activity with respect to the breast can be used for regimens of this invention, including any of the OCP regimens described herein either as the sole progestin or as a second progestin added to one or more of the daily dosages in an amount sufficient to protect the breast tissues, the ovarian epithilium and/or the uterus. When used as a second progestin in a regimen, the dosage of the second progestin is provided in one embodiment at a dosage equivalent of at least 0.125 mg of levonorgestrel, alternatively at least 0.25, alternatively at least 0.5, and alternatively at least 1.0, and alternatively at least 2.0, or alternatively at least 3.0 or more. (Preferably, the OCP regimens utilize a progestin having a progestational effect per mg as strong as levonorgestrel and/or an antiestrogenic effect per mg as strong as levonorgestrel.)The invention includes a contraceptive kit comprising tablets according to any of the regimens for oral contraception described in this application. The regimen is formulated to increase the TGF-$\beta$ expression and/or apoptotic effect of the regimen in the manner as taught in this application. For example, the regimens of this invention include the OCP regimens described in Table 2, but modified to increase TGF-$\beta$ expression and/or apoptosis induction by increasing the level of progestin in one or more tablets in each cycle or by increasing the level of progestin in one or more tablet one of the months in a three month cycle or by adding a different progestin in one or more of the tablets. Alternatively, another non-progestin agent could be added to one or more of the tablets to increase TGF-$\beta$ expression and/or apoptotic inductionor the formulation could be modified by changing the progestin to one which is more potent for TGF-$\beta$ upregulation or apoptotic effect. This invention contemplates both mono-phasic and multi-phasic regimens (including both OCP, HRT and other types of regimens). By the term "mono-phasic" as used herein, applicant means that within a cycle, the daily dosage of the therapeutically active compounds remains constant, except for placebo days, if any, in the regimen. For example, a regimen having 21 days of a constant level of progestin and estrogen with 7 days of placebo is mono-phasic as used herein. However, if another therapeutically active compound such as a vitamin or a retinoid is added to the otherwise placebo, then the regimen would not be mono-phasic as used herein: it would be multi-phasic, specifically bi-phasic, according to this application's use of the term.

By the term "multi-phasic" as used herein, applicant means that within a cycle, the daily dosage of the therapuetically active compounds varies at least once so that there are at least two phases with different levels and/or types of therapuetically active compounds. Accordingly, as the "phase" term is used herein by applicant, each "phase" in a multi-phase regimen is either the first phase having one or more therapuetically active compounds or a subsequent phase having one or more therapuetically active compounds with different levels and/or types of therapuetically active compounds as compared to the immediately prior phase. For example, a 28-day regimen having 21 days of a constant level of progestin and estrogen with 7 days of a estrogen bridge would be multi-phasic as used herein, specifically bi-phasic. A regimen having 7 days of progestin A, followed by 7 days of progestin B, followed by 7 days of progestin A at the same level as the first 7 days, followed by 7 days of placebo would be multi-phasic, having three phases and thus tri-phasic as those terms are used in this application.

The invention contemplates multi-phasic regimens, including OCP and HRT regimens, having two phases, having at least two phases, having three phases, having at least three phases, having four phases, having at least four phases, having five phases, having at least five phases, having six phases, having at least six phases, having seven phases, having at least seven phases, having eight phases, having at least eight phases, having nine two phases, having at least nine phases, having ten phases, having at least ten phases, having eleven phases, having at least eleven phases, having twelve phases, having at least twelve phases, having thirteen phases, having at least thirteen phases, having fourteen phases, having at least fourteen phases, having fifteen phases, having at least fifteen phases, having sixteen phases, or having at least sixteen phases.

This invention contemplates mono-phasic or multi-phasic OCP regimens for reducing the risk of ovarian cancer by increasing TGF-$\beta$ expression and/or apoptosis in the ovarian epithelium where the regimens have at least one or more of the daily dosages having at least 0.5 mg of norgestimate, preferably at least 0.8, more preferably at least 1.2, and even more preferably at least 1.8, and most preferably at least 2.5 or more. In multi-phasic regimens, this phase of the regimen is administered at least one day, more preferable at least two days or alternatively at least 3 days. Preferred ranges for the length of this phase in multi-phasic regimens are from 1–15 days, from 2–11 days, and from 3–7 days. The estrogen level used in this regimen preferably has no daily dosage exceeding 50 mcg EE dosage equivalent, and more preferably not to exceed 35 mcg, and even more preferably not to exceed 20 mcg, and most preferably 15 mcg or less, with EE and 17-Beta estradiol being preferred estrogens. A weaker estrogen or an estrogen having antiestrogenic activity (such as SERMs discussed below) can be used or added as a second estrogen to any of the regimens of this paragraph. One version of the regimen of this paragraph has the total dosage of norgestimate in a cycle not to exceed 8 mg. Another version of the regimen of this paragraph has the total dosage of norgestimate in a cycle exceeding 10 mg, preferably exceeding 15 mg. The cycle for the regimen is preferably 28 days, but other lengths are contemplated. The regimen of this paragraph can be bi-phasic, or can have at least three phases, and includes triphasic regimens. This invention provides a method of contraception which comprises administering to a female of child bearing age the OCP regimen of this paragraph. Alternatively, this invention contemplates a HRT regimen for post-menopausal women, and a HRT regimen for peri-menopausal women, having the ingredients and dosages mentioned above in this paragraph, except the estrogen dosages are 5 mcg or less EE dosage equivalent.

This invention contemplates mono-phasic or multi-phasic OCP regimens for reducing the risk of ovarian cancer by increasing TGF-$\beta$ expression and/or apoptosis in the ovarian epithelium where the regimens have at least one or more of the daily dosages having at least 2.1 mg of one or more of the progestins from the group consisting of norethindrone, and norethynodrel, preferably at least 2.5, more preferably at least 3.0, even more preferably at least 4.0, more preferably at least 5.0, more preferably at least 10 mg, and most preferably at >10 mg. In multi-phasic regimens, this phase of the regimen is administered at least one day, more preferable at least two days or alternatively at least 3 days. Preferred ranges for the length of this phase in multi-phasic regimens are from 1–15 days, from 2–11 days, and from 3–7 days. The estrogen level used in this regimen preferably has no daily dosage exceeding 50 mcg EE dosage equivalent, and more preferably not to exceed 35 mcg, and even more preferably not to exceed 20 mcg, and most preferably 15 mcg or less, with EE and 17-Beta estradiol being preferred estrogens. A weaker estrogen or an estrogen having antiestrogenic activity (such as SERMs discussed below) can be used or added as a second estrogen to any of the regimens of this paragraph. One version of the regimen of this paragraph has the total dosage of norethindrone in a cycle not to exceed 10 mg. Another version of the regimen of this paragraph has the total dosage of norgestimate in a cycle exceeding 20 mg, preferably exceeding 25 mg, more preferably exceeding 30 mg and even more preferably exceeding 40 mg. The cycle for the regimen is preferably 28 days, but other lengths are contemplated. The regimen of this paragraph can be bi-phasic, or can have at least three phases, and includes triphasic regimens. One version of the invention of this paragraph is a mono-phasic regimen with 10 mg or more of norethindrone daily dosage with an estrogen daily dosage of less than 50 mcg EE dosage equivalent, and more preferably not to exceed 35 mcg, and even more preferably not to exceed 20 mcg, and most preferably not to exceed 15 mcg. Alternatively, a multi-phasic regimen is used with at least one phase having 10 mg norethindrone or more and another phase having, preferably less than 10 mg norethindrone, with estrogen daily dosages of less than 50 mcg EE dosage equivalent, and more preferably not to exceed 35 mcg, even more preferably not to exceed 20 mcg, and most preferably not to exceed 15 mcg. This invention provides a method of contraception which comprises administering to a female of child bearing age the OCP regimen of this paragraph. Alternatively, this invention contemplates a HRT regimen for post-menopausal women, and a HRT regimen for peri-menopausal women, having the ingredients and dosages mentioned above in this paragraph, except the estrogen dosages are 5 mcg or less EE dosage equivalent.

This invention contemplates mono-phasic or multi-phasic OCP regimens for reducing the risk of ovarian cancer by increasing TGF-β expression and/or apoptosis in the ovarian epithelium where the regimens have at least one or more of the daily dosages having at least 0.25 mg of levonorgestrel, alternatively at least 0.5, alternatively at least 1.0, and alternatively at least 1.5, and alternatively at least 2.0, or alternatively at least 3.0, or alternatively at least 4.0 or more. In multi-phasic regimens, this phase of the regimen is administered at least one day, more preferable at least two days or alternatively at least 3 days. Preferred ranges for the length of this phase in multi-phasic regimens are from 1–15 days, from 2–11 days, and from 3–7 days. The estrogen level used in this regimen preferably has no daily dosage exceeding 50 mcg EE dosage equivalent, and more preferably not to exceed 35 mcg, and even more preferably not to exceed 20 mcg, and most preferably 15 mcg or less, with EE and 17-Beta estradiol being preferred estrogens. A weaker estrogen or an estrogen having antiestrogenic activity (such as SERMs discussed below) can be used or added as a second estrogen to any of the regimens of this paragraph. One version of the regimen of this paragraph has the total dosage of levonorgestrel in a cycle not to exceed 12 mg and alternatively not to exceed 10 mg and alternatively not to exceed 7.5 mg. Another version of the regimen of this paragraph has the total dosage of levonorgestrel in a cycle exceeding 15 mg, preferably exceeding 25 mg, more preferably exceeding 30 mg and even more preferably exceeding 40 mg. The cycle for the regimen is preferably 28 days, but other lengths are contemplated. The regimen of this paragraph can be bi-phasic, or can have at least three phases, and includes triphasic regimens. One version of the invention of this paragraph is a mono-phasic regimen with 0.25 mg or more of levonorgestrel daily dosage with an estrogen daily dosage of less than 50 mcg EE dosage equivalent, and more preferably not to exceed 20 mcg, and most preferably not to exceed 15 mcg. Alternatively, a multi-phasic regimen is used with at least one phase having 0.25 mg or levonorgestrel or more and another phase having less levonorgestrel, preferably less than 0.25 mg levonorgestrel, with estrogen daily dosages of less than 50 mcg EE dosage equivalent, and more preferably not to exceed 20 mcg, and most preferably not to exceed 15 mcg. This invention provides a method of contraception which comprises administering to a female of child bearing age the OCP regimen of this paragraph. Alternatively, this invention contemplates a HRT regimen for post-menopausal women, and a HRT regimen for peri-menopausal women, having the ingredients and dosages mentioned above in this paragraph, except the estrogen dosages are 5 mcg or less EE dosage equivalent.

This invention contemplates mono-phasic or multi-phasic OCP regimens for reducing the risk of ovarian cancer by increasing TGF-β expression and/or apoptosis in the ovarian epithelium where the regimens have at least one or more of the daily dosages having at least 0.5 mg of norgestrel, alternatively at least 1.0, alternatively at least 1.5, and alternatively at least 2.0, and alternatively at least 3.0, or alternatively at least 4.0 or more. In multi-phasic regimens, this phase of the regimen is administered at least one day, more preferable at least two days or alternatively at least 3 days. Preferred ranges for the length of this phase in multi-phasic regimens are from 1–15 days, from 2–11 days, and from 3–7 days. The estrogen level used in this regimen preferably has no daily dosage exceeding 50 mcg EE dosage equivalent, and more preferably not to exceed 35 mcg, and even more preferably not to exceed 20 mcg, and most preferably 15 mcg or less, with EE and 17-Beta estradiol being preferred estrogens. A weaker estrogen or an estrogen having antiestrogenic activity (such as SERMs discussed below) can be used or added as a second estrogen to any of the regimens of this paragraph. One version of the regimen of this paragraph has the total dosage of norgestrel in a cycle not to exceed 12 mg and alternatively not to exceed 10 mg and alternatively not to exceed 7.5 mg. Another version of the regimen of this paragraph has the total dosage of norgestrol in a cycle exceeding 15 mg, preferably exceeding 25 mg, more preferably exceeding 30 mg and even more preferably exceeding 40 mg. The cycle for the regimen is preferably 28 days, but other lengths are contemplated. The regimen of this paragraph can be bi-phasic, or can have at least three phases, and includes triphasic regimens. One version of the invention of this paragraph is a mono-phasic regimen with 0.5 mg or more of norgestrel daily dosage with an estrogen daily dosage of less than 50 mcg EE dosage equivalent, and more preferably not to exceed 35 mcg, and even more preferably not to exceed 20 mcg, and most preferably not to exceed 15 mcg. Alternatively, a multi-phasic regimen is used with at least one phase having 0.5 mg or norgestrel or more and another phase having less norgestrel, preferably less than 0.5 mg norgestrel, with estrogen daily dosages of less than 50 mcg EE dosage equivalent, and more preferably not to exceed 35 mcg, even more preferably not to exceed 20 mcg, and most preferably not to exceed 15 mcg. This invention provides a method of contraception which comprises administering to a female of child bearing age the OCP regimen of this paragraph. Alternatively, this invention contemplates a HRT regimen for post-menopausal women, and a HRT regimen for peri-menopausal women, having the ingredients and dosages mentioned above in this paragraph, except the estrogen dosages are 5 mcg or less EE dosage equivalent.

This invention contemplates mono-phasic or multi-phasic OCP regimens for reducing the risk of ovarian cancer by increasing TGF-β expression and/or apoptosis in the ovarian epithelium where the regimens have at least one or more of the daily dosages having at least 1.0 mg of norethindrone acetate, alternatively at least 1.5, alternatively at least 2.0, and alternatively at least 2.5, and alternatively at least 3.0, or alternatively at least 4.0 or more. In multi-phasic regimens, this phase of the regimen is administered at least one day, more preferable at least two days or alternatively at least 3 days. Preferred ranges for the length of this phase in multi-phasic regimens are from 1–15 days, from 2–11 days, and from 3–7 days. The estrogen level used in this regimen preferably has no daily dosage exceeding 50 mcg EE dosage equivalent, and more preferably not to exceed 35 mcg, and even more preferably not to exceed 20 mcg, and most preferably 15 mcg or less, with EE and 17-Beta estradiol being preferred estrogens. A weaker estrogen or an estrogen having antiestrogenic activity (such as SERMs discussed below) can be used or added as a second estrogen to any of the regimens of this paragraph. One version of the regimen of this paragraph has the total dosage of norethindrone acetate in a cycle not to exceed 12 mg and alternatively not to exceed 10 mg and alternatively not to exceed 7.5 mg. Another version of the regimen of this paragraph has the total dosage of norethindrone acetate in a cycle exceeding 15 mg, preferably exceeding 25 mg, more preferably exceeding 30 mg and even more preferably exceeding 40 mg. The cycle for the regimen is preferably 28 days, but other lengths are contemplated. The regimen of this paragraph can be bi-phasic, or can have at least three phases, and includes triphasic regimens. This invention provides a method of contraception which comprises administering to a female of child bearing age the OCP regimen of this paragraph. Alternatively, this invention contemplates a HRT regimen for post-menopausal women, and a HRT regimen for peri-menopausal women, having the ingredients and dosages mentioned above in this paragraph, except the estrogen dosages are 5 mcg or less EE dosage equivalent.

This invention contemplates mono-phasic or multi-phasic OCP regimens for reducing the risk of ovarian cancer by increasing TGF-$\beta$ expression and/or apoptosis in the ovarian epithelium where the regimens have at least one or more of the daily dosages having at least 0.7 mg of desogestrol, alternatively at least 1.2, alternatively at least 1.8, and alternatively at least 2.4, and alternatively at least 3.0, or alternatively at least 4.0 or more. In multi-phasic regimens, this phase of the regimen is administered at least one day, more preferable at least two days or alternatively at least 3 days. Preferred ranges for the length of this phase in multi-phasic regimens are from 1–15 days, from 2–11 days, and from 3–7 days. The estrogen level used in this regimen preferably has no daily dosage exceeding 50 mcg EE dosage equivalent, and more preferably not to exceed 35 mcg, and even more preferably not to exceed 20 mcg, and most preferably 15 mcg or less, with EE and 17-Beta estradiol being preferred estrogens. A weaker estrogen or an estrogen having antiestrogenic activity (such as SERMs discussed below) can be used or added as a second estrogen to any of the regimens of this paragraph. One version of the regimen of this paragraph has the total dosage of desogestrol in a cycle not to exceed 12 mg and alternatively not to exceed 10 mg and alternatively not to exceed 7.5 mg. Another version of the regimen of this paragraph has the total dosage of desogestrol in a cycle exceeding 10 mg, preferably at least 15 mg, more preferably at least 20 mg and even more preferably at least 30 mg. The cycle for the regimen is preferably 28 days, but other lengths are contemplated. The regimen of this paragraph can be bi-phasic, or can have at least three phases, and includes triphasic regimens. This invention provides a method of contraception which com-prises administering to a female of child bearing age the OCP regimen of this paragraph. Alternatively, this invention contemplates a HRT regimen for post-menopausal women, and a HRT regimen for peri-menopausal women, having the ingredients and dosages mentioned above in this paragraph, except the estrogen dosages are 5 mcg or less EE dosage equivalent.

This invention contemplates mono-phasic or multi-phasic OCP regimens for reducing the risk of ovarian cancer by increasing TGF-$\beta$ expression and/or apoptosis in the ovarian epithelium where the regimens have at least one or more of the daily dosages having at least 4.1 mg of dienogest or drosprirenone, alternatively at least 5.0, alternatively at least 6.0, and alternatively at least 6.5, and alternatively at least 7.0, or alternatively at least 8.0 or more. In multi-phasic regimens, this phase of the regimen is administered at least one day, more preferable at least two days or alternatively at least 3 days. Preferred ranges for the length of this phase in multi-phasic regimens are from 1–15 days, from 2–11 days, and from 3–7 days. The estrogen level used in this regimen preferably has no daily dosage exceeding 50 mcg EE dosage equivalent, and more preferably not to exceed 35 mcg (as used herein "$\mu$g" and "mcg" each mean microgram), and even more preferably not to exceed 20 mcg, and most preferably 15 mcg or less, with EE and 17-Beta estradiol being preferred estrogens. A weaker estrogen or an estrogen having antiestrogenic activity (such as SERMs discussed below) can be used or added as a second estrogen to any of the regimens of this paragraph. One version of the regimen of this paragraph has the total dosage of dienogest or drosprirenone in a cycle not to exceed 20 mg and alternatively not to exceed 15 mg and alternatively not to exceed 9.0 mg. Another version of the regimen of this paragraph has the total dosage of dienogest or drosprirenone in a cycle exceeding 30 mg, preferably exceeding 40 mg, more preferably exceeding 45 mg and even more preferably exceeding 50 mg. The cycle for the regimen is preferably 28 days, but other lengths are contemplated. The regimen of this paragraph can be bi-phasic, or can have at least three phases, and includes triphasic regimens. This invention provides a method of contraception which comprises administering to a female of child bearing age the OCP regimen of this paragraph. Alternatively, this invention contemplates a HRT regimen for post-menopausal women, and a HRT regimen for peri-menopausal women, having the ingredients and dosages mentioned above in this paragraph, except the estrogen dosages are 5 mcg or less EE dosage equivalent.

This invention contemplates mono-phasic or multi-phasic OCP regimens for reducing the risk of ovarian cancer by increasing TGF-$\beta$ expression and/or apoptosis in the ovarian epithelium where the regimens have at least one or more of the daily dosages having at least 0.5 mg of ethynodiol diacetate, alternatively at least 1.0, alternatively at least 1.5, and alternatively at least 2.0, and alternatively at least 3.0, or alternatively at least 4.0 or more. In multi-phasic regimens, this phase of the regimen is administered at least one day, more preferable at least two days or alternatively at least 3 days. Preferred ranges for the length of this phase in multi-phasic regimens are from 1–15 days, from 2–11 days, and from 3–7 days. The estrogen level used in this regimen preferably has no daily dosage exceeding 50 mcg EE dosage equivalent, and more preferably not to exceed 35 mcg, and even more preferably not to exceed 20 mcg, and most preferably 15 mcg or less, with EE and 17-Beta estradiol being preferred estrogens. A weaker estrogen or an estrogen having antiestrogenic activity (such as SERMs discussed below) can be used or added as a second estrogen to any of the regimens of this paragraph. One version of the regimen of this paragraph has the total dosage of ethynodiol diacetate in a cycle not to exceed 12 mg and alternatively not to exceed 10 mg and alternatively not to exceed 7.5 mg. Another version of the regimen of this paragraph has the total dosage of ethynodiol diacetate in a cycle exceeding 15 mg, preferably exceeding 25 mg, more preferably exceeding 30 mg and even more preferably exceeding 40 mg. The cycle for the regimen is preferably 28 days, but other lengths are contemplated. The regimen of this paragraph can be bi-phasic, or can have at least three phases, and includes triphasic regimens. One version of the invention of this paragraph is a mono-phasic regimen with 1.0 mg or more of ethinodiol diacetate daily dosage with an estrogen daily dosage of less than 50 mcg EE dosage equivalent, and more preferably not to exceed 35 mcg, and even more preferably not to exceed 20 mcg, and most preferably not to exceed 15 mcg. Alternatively, a multi-phasic regimen is used with at least one phase having 1.0 mg or ethinodiol diacetate or more and another phase having less ethinodiol diacetate, preferably less than 1.0 mg, with estrogen daily dosages of less than 50 mcg EE dosage equivalent, and more preferably not to exceed 35 mcg, even more preferably not to exceed 20 mcg, and most preferably not to exceed 15 mcg. This invention provides a method of contraception which comprises administering to a female of child bearing age the OCP regimen of this paragraph. Alternatively, this invention contemplates a HRT regimen for post-menopausal women, and a HRT regimen for peri-menopausal women, having the ingredients and dosages mentioned above in this paragraph, except the estrogen dosages are 5 mcg or less EE dosage equivalent.

This invention contemplates mono-phasic or multi-phasic OCP regimens for reducing the risk of ovarian cancer by increasing TGF-β expression and/or apoptosis in the ovarian epithelium where the regimens have at least one or more of the daily dosages having a progestin at a dosage equivalent of at least 0.25 mg of levonorgestrel, alternatively at least 0.5, alternatively at least 1.0, alternatively at least 1.5, alternatively at least 2.0, and alternatively at least 2.5, and alternatively at least 3.0, or alternatively at least 4.0 or more. In multi-phasic regimens, this phase of the regimen is administered at least one day, more preferable at least two days or alternatively at least 3 days. Preferred ranges for the length of this phase in multi-phasic regimens are from 1–15 days, from 2–11 days, and from 3–7 days. The estrogen level used in this regimen preferably has no daily dosage exceeding 50 mcg EE dosage equivalent, and more preferably not to exceed 35 mcg, and even more preferably not to exceed 20 mcg, and most preferably 15 mcg or less, with EE and 17-Beta estradiol being preferred estrogens. A weaker estrogen or an estrogen having antiestrogenic activity (such as SERMs discussed below) can be used or added as a second estrogen to any of the regimens of this paragraph. One version of the regimen of this paragraph has the total dosage of progestin at a dosage equivalent in a cycle not to exceed 12 mg of levonorgestrel and alternatively not to exceed 10 mg dosage equivalent and alternatively not to exceed 7.5 mg dosage equivalent. Another version of the regimen of this paragraph has the total dosage of progestin at a dosage equivalent in a cycle exceeding 15 mg of levonorgestrel, preferably exceeding 25 mg dosage equivalent, more preferably exceeding 30 mg dosage equivalent and even more preferably exceeding 40 mg dosage equivalent. The cycle for the regimen is preferably 28 days, but other lengths are contemplated. The regimen of this paragraph can be bi-phasic, or can have at least three phases, and includes triphasic regimens. This invention provides a method of contraception which comprises administering to a female of child bearing age the OCP regimen of this paragraph. Alternatively, this invention contemplates a HRT regimen for post-menopausal women, and a HRT regimen for peri-menopausal women, having the ingredients and dosages mentioned above in this paragraph, except the estrogen dosages are 5 mcg or less EE dosage equivalent.

This invention also provides a method of contraception which comprises administering to a female of child bearing age for 23–25 consecutive days, a first phase combination of a progestin at a daily dosage of 40–500 mcg trimegestone, 250 mcg-4 mg dienogest, or 250 mcg-4 mg drospirenone, and an estrogen at a daily dosage equivalent in estrogenic activity to 10–30 mcg ethinyl estradiol for 9–13 days beginning on day 1 of the menstrual cycle, wherein the same dosage of the progestin and estrogen combination is administered in each of the 9–13 days, and a second phase combination of a progestin at a daily dosage of 40–500 mcg trimegestone, 250 mcg-4 mg dienogest, or 250 mcg-4 mg drospirenone, and an estrogen at a daily dosage equivalent in estrogenic activity to 10–30 mcgethinyl estradiol, for 11–15 days beginning on the day immediately following the last day of administration of the first phase combination, wherein the same dosage of the progestin and estrogen combination is administered in each of the 11–15 days, provided that the daily dosage of second phase progestin is greater than the daily dosage of the first phase progestin and that the daily dosage of the second phase estrogen is greater than or equal to the daily dosage of the first phase estrogen and wherein the regimen is modified so that one or more of the daily dosages further includes a TGF-Beta upregulating agent and/or apoptosis-inducing agent such as one or more selected from the group of the retinoids, dietary flavanoids, anti-inflammatory drugs, monoterpenes, S-adenosyl-L-methionine, selenium and vitamin D compounds (in one of the hormonal dosages and/or otherwise placebos). Alternatively, the regimen is modified such that one or more of the daily dosages includes at least 1.0 mg trimegestone, at least 5.0 mg dienogest, or at least 5.0 mg drospirenone.

This invention further includes a method of contraception which comprises administering orally to a female of child bearing age for 23–25 consecutive days, a first phase combination of a progestin at a daily dosage selected from the group consisting of 40–500 mcg trimegestone, 250 mcg-4 mg dienogest, and 250 mcg-4 mg drospirenone, and an estrogen at a daily dosage equivalent in estrogenic activity to 10–30 mcg ethinyl estradiol for 3–8 days beginning on day 1 of the menstrual cycle, wherein the same dosage of the progestin and estrogen combination is administered in each of the 3–8 days, a second phase combination of a progestin at a daily dosage selected from the group consisting of 40–500 mcg trimegestone, 250 mcg-4 mg dienogest, and 250 mcg-4 mg drospirenone, and an estrogen at a daily dosage equivalent in estrogenic activity to 10–30 mcg ethinyl estradiol, for 4–15 days beginning on the day immediately following the last day of administration of the first phase combination, wherein the same dosage of the progestin and estrogen combination is administered in each of the 4–15 days, a third phase combination of a progestin at a daily dosage selected from the group consisting of 40–500 mcg trimegestone, 250 mcg-4 mg dienogest, and 250 mcg-4 mg drospirenone, and an estrogen at a daily dosage equivalent in estrogenic activity to 10–30 mcg ethinyl estradiol, for 4–15 days beginning on the day immediately following the last day of administration of the second phase combination, wherein the same dosage of the progestin and estrogen combination is administered in each of the 4–15 days, and an estrogen phase estrogen at a daily dosage equivalent in estrogenic activity to 5–30 mcg ethinyl estradiol, for 3–5 days beginning on the day immediately following the last day of administration of the third phase combination, wherein the same dosage of the estrogen is administered in each of the 3–5 days, provided that the daily dosage of the combination administered in the first phase is not the same as the daily dosage of the combination administered in the second phase and that the daily dosage of the combination administered in the second phase is not the same as the daily dosage of the combination administered in the third phase and wherein the regimen is modified so that one or more of the daily dosages further includes a further TGF-Beta upregulating agent and/or apoptosis-inducing agent such as one or more selected from the group of the retinoids, dietary flavanoids, anti-inflammatory drugs, monoterpenes, S-adenosyl-L-methionine, selenium and vitamin D compounds (in one of the hormonal dosages and/or otherwise placebos). Alternatively, the regimen is modified such that one or more of the daily dosages includes at least 1.0 mg trimegestone, at least 5.0 mg dienogest, or at least 5.0 mg drospirenone.

This invention further provides a method of contraception which comprises administering to a female of child bearing age a first phase of a combination of a progestin at a daily dosage equivalent in progestational activity to 40–125 mcg levonorgestrel and an estrogen at a daily dosage equivalent in estrogenic activity to 10–20 mcg ethinyl estradiol for 3–8 days beginning on day 1 of the menstrual cycle. The same daily dosage of the progestin and estrogen is administered for each of the 3–8 days. A second phase of a combination of a progestin at a daily dosage equivalent in progestational activity to 40–125 mcg levonorgestrel and an estrogen at a daily dosage equivalent in estrogenic activity to 10–20 mcg ethinyl estradiol is administered for 4–15 days beginning on the day immediately following the last day of administration of the first phase. The same daily dosage of the progestin and estrogen is administered for each of the 4–15 days. A third phase of a combination of a progestin at a daily dosage equivalent in progestational activity to 40–125 mcg levonorgestrel and an estrogen at a daily dosage equivalent in estrogenic activity to 10–20 mcg ethinyl estradiol is administered for 4–15 days beginning on the day immediately following the last day of administration of the second phase. The same daily dosage of the progestin and estrogen is administered for each of the 4–15 days. The total administration for all three phases is 23–25 days. The daily dosage of the progestin/estrogen combination administered in any phase is distinct from the dosage of the progestin/estrogen combination administered in either of the other two phases. The regimen is modified so that one or more of the daily dosages further includes a TGF-Beta upregulating agent and/or apoptosis-inducing agent such as one or more selected from the group of the retinoids, dietary flavanoids, anti-inflammatory drugs, monoterpenes, S-adenosyl-L-methionine, selenium and vitamin D compounds (in one of the hormonal dosages and/or otherwise placebos). Alternatively, the regimen is modified such that one or more of the daily dosages includes a progestin dosage equivalent of at least 0.3 mg of levonorgestrel, alternatively at least 0.5, alternatively at least 1.0, and alternatively at least 1.5, and alternatively at least 2.0, or alternatively at least 3.0 or more.

The invention further includes a method of contraception which comprises administering for 21 successive days to a female of childbearing age a combination of an estrogen and a progestin in a low but contraceptively effective daily dosage corresponding in estrogenic activity to 0.02–0.05 mg of 17α-ethinylestradiol and in progestogenic activity to 0.065–0.75 mg of norethindrone for 5–8 days; for the next 7–11 days an estrogen daily dosage equal to 0.02–0.05 mg of 17α-ethinylestradiol and in progestogenic activity to 0.250–1.0 mg of norethindrone; and for the next 3–7 days an estrogen daily dosage equal to 0.02–0.05 mg of 17α-ethinylestradiol and in progestogenic activity 0.35–2.0 mg of norethindrone; followed by 6–8 days without estrogen and progestogen administration, provided that the estrogen daily dosage can be the same for each period and wherein the regimen is modified so that one or more of the daily dosages further includes a TGF-Beta upregulating agent and/or apoptosis-inducing agent such as one or more selected from the group of the retinoids, dietary flavanoids, anti-inflammatory drugs, monoterpenes, S-adenosyl-L-methionine, selenium and vitamin D compounds (in one of the hormonal dosages and/or otherwise placebos). Alternatively, the regimen is modified such that one or more of the daily dosages includes a progestin dosage equivalent of at least 2.1 mg of norethindrone, preferably at least 2.5, more preferably at least 3.0, and even more preferably at least 4.0, and most preferably at least 5.0.

This invention further contemplates a method of contraception comprising the steps of sequentially-administering to a female of child bearing age: (1) for about 4 to about 7 days, a composition I containing about 0.5–1.5 mg norethindrone acetate and about 10–50 mcg ethinyl estradiol, (2) for about 5 to about 8 days, a composition II containing about 0.5–1.5 mg norethindrone acetate and about 10–50 mcg ethinyl estradiol, and (3) for about 7 to about 12 days, a composition III containing 0.5–1.5 mg norethindrone acetate and about 10–50 mcg ethinyl estradiol, wherein the amount of ethinyl estradiol is increased stepwise by the amount of at least 5 mcg in each step and wherein the regimen is modified so that one or more of the daily dosages further includes a TGF-Beta upregulating agent and/or apoptosis-inducing agent such as one or more selected from the group of the retinoids, dietary flavanoids, anti-inflammatory drugs, monoterpenes, S-adenosyl-L-methionine, selenium and vitamin D compounds (in one of the hormonal dosages and/or otherwise placebos). Alternatively, the regimen is modified such that one or more of the daily dosages includes at least 1.7 mg of norethindrone acetate, alternatively at least 2.0, and alternatively at least 2.5, and alternatively at least 3.0, or alternatively at least 4.0 or more.

This invention further includes contraceptive regimens which consist of the administration of a combination of a progestin (50–75 μg gestodene, 75–125 μg levonorgestrel, 60–150 μg desogestrel, 60–150 μg 3-ketodesogestrel, 100–300 μg drospirenone, 100–200 μg cyproterone acetate, 200–300 μg norgestimate, or 350–750 μg norethisterone) and an estrogen (15–25 μg EE dosage equivalent) for 23–24 days per cycle and wherein the regimen is modified so that one or more of the daily dosages further includes a TGF-Beta upregulating agent and/or apoptosis-inducing agent such as one or more selected from the group of the retinoids, dietary flavanoids, anti-inflammatory drugs, monoterpenes, S-adenosyl-L-methionine, selenium and vitamin D compounds (in one of the hormonal dosages and/or otherwise placebos). Alternatively, the regimen is modified such that one or more of the daily dosages includes at least 250 μg gestodene, at least 350 μg levonorgestrel, at least 400 μg desogestrel, at least 400 μg 3-ketodesogestrel, at least 750 μg drospirenone, at least 600 μg cyproterone acetate, at least 800 μg norgestimate, or at least 2.25 mg norethisterone.

This invention further contemplates triphasic progestin/estrogen combinations in which the amount of the estrogenic component is increased stepwise over the three phases. Contraceptive steroid combinations are taken for 4–7 days during the first phase (5 days being preferred); for 5–8 days during the second phase (7 days preferred); and for 7–12 days during the third phase (9 days being preferred). Following the administration of 21-days of the contraceptive steroid combination, placebo is taken for 7 days. For all three phases, 0.5–1.5 mg of norethindrone acetate is used in the progestin, with 1 mg being preferred. 10–30 $\mu$g EE is used in the first phase, 20–40 $\mu$g in the second, and 30–50 $\mu$g in the third phase and wherein the regimen is modified so that one or more of the daily dosages further includes a TGF-Beta upregulating agent and/or apoptosis-inducing agent such as one or more selected from the group of the retinoids, dietary flavanoids, anti-inflammatory drugs, monoterpenes, S-adenosyl-L-methionine, selenium and vitamin D compounds (in one of the hormonal dosages and/or otherwise placebos). Alternatively, the regimen is modified such that one or more of the daily dosages includes at least 1.8 mg of norethindrone, preferably at least 2.5, more preferably 3.0, and even more preferably 4.0, and most preferably 5.0.

This invention also contemplates triphasic progestin/estrogen combination regimens in which contraceptive hormones are administered for 21 days. Contraceptive steroid combinations are taken for 5–8 days during the first phase (7 days being preferred); for 7–11 days during the second phase (7 days preferred); and for 3–7 days during the third phase (7 days being preferred). In all three phases, an estrogen at a daily dosage equivalent to 20–50 $\mu$g EE is administered in combination with a progestin having a daily dosage equivalent to 65–750 $\mu$g norethindrone in the first phase, 0.25–1.0 mg norethindrone in the second phase, and 0.35–2.0 mg norethindrone in the third phase, and wherein the regimen is modified so that one or more of the daily dosages further includes a TGF-Beta upregulating agent and/or apoptosis-inducing agent such as one or more selected from the group of the retinoids, dietary flavanoids, anti-inflammatory drugs, monoterpenes, S-adenosyl-L-methionine, selenium and vitamin D compounds (in one of the hormonal dosages and/or otherwise placebos). Alternatively, the regimen is modified such that one or more of the daily dosages includes at least 2.1 mg of norethindrone, preferably at least 2.5, more preferably 3.0, and even more preferably 4.0, and most preferably 5.0.

This invention also contemplates triphasic 21-day progestin/estrogen combination regimens in which a combination of 40–70 $\mu$g gestodene and an estrogen at a daily dosage equivalent of 20–35 $\mu$g EE is administered for 4–6 days in the first phase; 50–100 $\mu$g gestodene and an estrogen at a daily dosage equivalent of 30–50 $\mu$g EE is administered for 4–6 days in the second phase; and 80–120 $\mu$g gestodene and an estrogen at a daily dosage equivalent of 20–50 $\mu$g EE is administered for 9–11 days in the third phase, and placebo is administered for 7 days following the 21-day contraceptive steroid regimen; and wherein the regimen is modified so that one or more of the daily dosages further includes a TGF-Beta upregulating agent and/or apoptosis-inducing agent such as one or more selected from the group of the retinoids, dietary flavanoids, anti-inflammatory drugs, monoterpenes, S-adenosyl-L-methionine, selenium and vitamin D compounds (in one of the hormonal dosages and/or otherwise placebos). Alternatively, the regimen is modified such that one or more of the daily dosages includes at least 200 mcg of gestodene, preferably at least 300, more preferably 600, and even more preferably 1000, and most preferably 1500.

Alternatively, another agent could be added to one or more of the tablets of the OCP formulations, including any of the formulations described in the Background, to increase TGF-$\beta$ expression and/or apoptotic induction, or by adding another progestin or changing the progestin to one which is more potent for TGF-$\beta$ upregulation or apoptotic effect.

It is contemplated that the higher doses of progestins in the preferred regimens for either monophasic, biphasic, triphasic or any other multi-phasic schedules can alternatively be given in units of time comprising 1 day, 1–3 days, 3–5days, 6–10 days, 10–14 days, or longer. Furthermore, these units of time could be applicable to a regimen comprising a one month cycle, 2 month cycle, 3–6 month cycle or longer. It is further contemplated that exemplary regimens according to this invention would consist of administering progestins in the lowest doses possible, except for the units of time during which progestin dose would be markedly increased in order to maximize TGF-$\beta$ expression and/or apoptosis in the ovarian epithelium. The objective of this approach would be to devise a contraceptive regimen with the least side effects and least overall exposure to progestin, while at the same time maximizing preventive effects against ovarian cancer. An estrogen having a weak estrogenic activity or antiestrogenic activity can be added to any of the formulations mentioned in this paragraph in lieu of or in addition to the estrogen in the current formulation.

Yet another aspect of the present invention provides a method for preventing the development of ovarian cancer in infertile female subjects, comprising administering a progestin product according to a regimen for hormone replacement therapy. Again, this can be accomplished in a number of ways, including altering the dosage, timing, ratio of progestin product to estrogen product, or the type of progestin product. Other contemplated regimens would include, for example, administering or delivering progestin product in doses lower or higher than those previously used in hormone replacement therapy; or administering a progestin product with estrogen product at a progestin/estrogen ratio that is higher than that previously used in hormone replacement therapy. In addition, or in the alternative, other TGF-$\beta$ inducing agents could be added.

Estrogen is the primary agent in hormone replacement therapy. Postmenopausal women are generally given estrogen alone, or with low doses of progestins. The hormones may be administered continuously or cyclically. Continuous administration is typically 0.625 mg Premarin (a conjugated equine estrogen) daily or its equivalent, with 2.5 mg Provera (medroxyprogesterone acetate) daily. Cyclical administration is typically 25 consecutive days of 0.625 mg Premarin daily, with 10 mg Provera daily on days 16 through 25, followed by 5 days of no hormone treatment (during which time these women will menstruate).

Exemplary regimens according to this aspect of the present invention include HRT regimens with doses of progestin product less than a daily dose equivalent to 2.5 mg of medroxyprogesterone acetate daily, or less than 0.5 mg daily of a norethindrone equivalent dose. Another exemplary regimen includes a dose of progestin product greater than a daily dose equivalent to 10 mg of medroxyprogesterone acetate daily for 10 days every month. Exemplary regimens according to this aspect of the invention include administering progestin product at a daily dose equal to or greater than 2.5 mg daily, equal to or higher than 5 mg daily, or equal to or higher than 10 mg daily of a norethindrone equivalent dose. Alternatively, a regimen useful according to the invention is that by which is administered a cumulative monthly dosage greater than the equivalent of 50 mg or more preferably 100 mg of norethindrone. Thus, the invention provides progestin product dosages which are greater than those currently administered on a daily and/or monthly basis.

It is contemplated that preferred HRT regimens according to an aspect of the invention would contain the lowest possible daily doses of both estrogen and progestin, but with intervening phases containing significantly higher doses of progestin in order to maximize biologic effects on the ovarian epithelium such as induction of TGF-$\beta$ and or apoptosis. Accordingly, the preferred regimens would minimize risks/side effects by lowering average daily dose of hormone during the majority of each hormone cycle, but would provide for maximal prevention against ovarian cancer via use of "pulsed" high dose exposure to progestins.

This invention contemplates HRT regimens comprising estrogen and progestin such as Prempro where medroxyprogesterone acetate is administered at daily doses greater than 10 mg daily, preferably greater than 20 mg daily, and more preferably at least 30 mg daily of more for a phase of time that could last one day, one to three days, three to five days, 5–14 days or more; and with regimen cycles lasting one month, two months, three months or more. Alternatively, a more potent progestin such as levonorgestrel is substituted for provera for one or more of the days of the regimen, at doses such as at least 0.25 mg per day, more preferably at least 0.5 mg per day, most preferably at least 1 mg per day or more, for a phase of time such as that described above. The levonorgestrel is alternatively added as an additional progestin in the regimen in one or more of the daily dosages.

Ideally, the optimal regimen for HRT would use the lowest dosages of estrogen and progestin products possible in combination with cyclic high dosages of progestin to achieve protection. According to one such regimen a daily dosage of estrogen comparable to 0.325 mg to 0.625 mg conjugated estrogen, i.e. 0.010 or 0.015 mg ethinyl estradiol, plus 0.05 mg levonorgestrel is administered daily for days 1–25 followed by administration on days 26–30 of the same dosage of an estrogen product plus 0.15 or more preferably 0.25 mg or more preferably 0.5 or even more preferably 1 mg of levonorgestrel. This invention specifically includes modifications of each of the current regimens of HRT formulations to maximize the protective effect of the regimen. These modifications include adding an additional agent to the regimen, specifically a TGF-$\beta$ inducing and/or apoptosis inducing agent. This invention contemplates taking any of the current formulations and adding to one or more daily dosages in the regimen a Vitamin D compound. In addition, this invention contemplates taking any of the known HRT formulations and adding a retinoid to one or more of the daily dosages in the regimen. This invention further contemplates taking any one of the known HRT formulations, and changing them to contain a more potent progestin. This invention further contemplates adding higher pulses of progestin at one or more points during the one-month cycle or three-month cycle of HRT usage. This added pulse of progestin would be at amounts greater than 5 mg of medroxyprogesterone acetate or equivalents thereof per day, preferably with the pulsed amount being at least 10 mg of progestin-equivalent to medroxyprogesterone acetate or more per day, and even more preferably at dosages of 20 mg or more preferably at least 30 mg equivalent of medroxyprogesterone acetate in one or more daily dosages during the cycle. The duration of the higher pulse of progestin could be as long as one day, more preferably as long as three days, even more preferably as long as 4–10 days during a one month cycle. This invention further contemplates substituting the estrogen in the current regimens with a weaker estrogen or an estrogen having higher anti-estrogenic activity, such as tamoxifen or raloxifene. The invention further contemplates combining two or more of the above modifications discussed above in this paragraph. (Preferably, the HRT regimens utilize a progestin having a progestational effect per mg as strong as levonorgestrel and/or an antiestrogenic effect per mg as strong as levonorgestrel.)

This invention further provides a HRT regimen which comprises a first phase comprising an estrogen at a daily dosage equivalent in estrogenic activity of 0.2–2.5 mg conjugated estrogens for 3–20 days, with estradiol, estrified estrogens, and conjugated estrogens being preferred and conjugated estrogens most preferred, and with 0.3–0.625 mg being the preferred daily dosage range and 0.3 mg most preferred, and with 10–18 days being the preferred length of the first phase and 14 days most preferred. The HRT regimen comprises a second phase comprising an estrogen at a daily dosage equivalent in estrogenic activity of 0.2–2.5 mg conjugated estrogens and a progestin at a daily dosage equivalent in progestinal activity of 2.5–10 mg medroxyprogesterone acetate for 3–20 days, with estradiol, estrified estrogens, and conjugated estrogens being preferred estrogens and conjugated estrogens most preferred, and with 0.3–0.625 mg dosage equivalent of conjugated estrogens being preferred daily estrogen dosage and 0.3 mg most preferred and with medroxy-progesterone acetate, levonorgestrel, norgestrol, and gestodene being preferred progestins, and medroxy-progesterone most preferred progestin (with 2.5 and 5 mg dosage equivalent of medroxy-progesterone acetate being most preferred), and with 10–18 days being the preferred length of the second phase and 14 days most preferred. The regimen is modified so that one or more of the daily dosages further includes a TGF-Beta upregulating agent and/or apoptosis-inducing agent such as one or more selected from the group of the retinoids, dietary flavanoids, anti-inflammatory drugs, monoterpenes, S-adenosyl-L-methionine, selenium and vitamin D compounds (in one of the hormonal dosages and/or otherwise placebos). Alternatively, the regimen is modified such that one or more of the daily dosages includes a progestin dosage equivalent of at least 0.3 mg of levonorgestrel, alternatively at least 0.5, alternatively at least 1.0, and alternatively at least 1.5, and alternatively at least 2.0, or alternatively at least 3.0 or more. The regimen of this paragraph can be bi-phasic, or can have at least three phases, and includes triphasic regimens, but preferably is less than 5 phases. This invention provides administering the HRT regimen of this paragraph to a post-menopausal female who is no longer ovulating or to a climacteric female. (Preferably, the HRT regimens of this paragraph utilize at least one progestin having a progestational effect per mg as strong as levonorgestrel and/or an antiestrogenic effect per mg as strong as levonorgestrel.)

This invention contemplates HRT regimens for reducing the risk of ovarian cancer by increasing TGF-$\beta$ expression and/or apoptosis in the ovarian epithelium where the regimens have at least one phase with one or more of the daily dosages in one of the phases having at least 0.3 mg of norgestimate, preferably at least 0.5, more preferably at least 1.0, and even more preferably at least 1.5, and most preferably at least 2.0 or more. This phase of the regimen is administered at least one day, more preferable at least two days or alternatively at least 3 days. Preferred ranges for the length of this phase are from 1–15 days, from 2–11 days, and from 3–7 days. The estrogen level used in this regimen preferably has no daily dosage exceeding 50 mcg EE dosage equivalent, and more preferably not to exceed 35 mcg, and even more preferably not to exceed 25 mcg, with EE, conjugated estrogens, and 17-Beta estradiol being preferred estrogens. A weaker estrogen or an estrogen having antiestrogenic activity (such as SERMs) can be used or added as a second estrogen to any of the regimens of this paragraph. One version of the regimen of this paragraph has the total dosage of norgestimate in a cycle not to exceed 5 mg. Another version of the regimen of this paragraph has the total dosage of norgestimate in a cycle exceeding 8 mg, preferably exceeding 12 mg. The cycle for the regimen is preferably 28 days, but other lengths are contemplated such as 20–35 days. The regimen of this paragraph can be mono-phasic, can be bi-phasic, or can have at least three phases, and includes triphasic regimens, but preferably is less than 5 phases. This invention provides administering the HRT regimen of this paragraph to a post-menopausal female who is no longer ovulating or to a climacteric female.

This invention contemplates HRT regimens for reducing the risk of ovarian cancer by increasing TGF-$\beta$ expression and/or apoptosis in the ovarian epithelium where the regimens have at least one phase with one or more of the daily dosages in one of the phases having at least 0.5 mg of norethindrone, preferably at least 1.0, more preferably at least 2.0, and even more preferably at least 3.0, and most preferably at least 4.0. This phase of the regimen is administered at least one day, more preferable at least two days or alternatively at least 3 days. Preferred ranges for the length of this phase are from 1–15 days, from 2–11 days, and from 3–7 days. The estrogen level used in this regimen preferably has no daily dosage exceeding 50 mcg EE dosage equivalent, and more preferably not to exceed 35 mcg, and even more preferably not to exceed 25 mcg, with EE, conjugated estrogens, and 17-Beta estradiol being preferred estrogens. A weaker estrogen or an estrogen having antiestrogenic activity (such as SERMS) can be used or added as a second estrogen to any of the regimens of this paragraph. One version of the regimen of this paragraph has the total dosage of norethindrone in a cycle not to exceed 10 mg. Another version of the regimen of this paragraph has the total dosage of norgestimate in a cycle exceeding 20 mg, preferably exceeding 25 mg, more preferably exceeding 30 mg and even more preferably exceeding 40 mg. The cycle for the regimen is preferably 28 days, but other lengths are contemplated such as 20–35 days. The regimen of this paragraph can be mono-phasic, can be bi-phasic, or can have at least three phases, and includes triphasic regimens, but preferably is less than 5 phases. This invention provides administering the HRT regimen of this paragraph to a post-menopausal female who is no longer ovulating or to a climacteric female the HRT regimen of this paragraph.

This invention contemplates HRT regimens for reducing the risk of ovarian cancer by increasing TGF-$\beta$ expression and/or apoptosis in the ovarian epithelium where the regimens have at least one phase with one or more of the daily dosages in one of the phases having at least 0.3 mg of levonorgestrel, alternatively at least 0.5, alternatively at least 1.0, and alternatively at least 1.5, and alternatively at least 2.0, or alternatively at least 3.0 or alternatively at least 4.0, or alternatively greater than 5.0. This phase of the regimen is administered at least one day, more preferable at least two days or alternatively at least 3 days. Preferred ranges for the length of this phase are from 1–15 days, from 2–11 days, and from 3–7 days. The estrogen level used in this regimen preferably has no daily dosage exceeding 50 mcg EE dosage equivalent, and more preferably not to exceed 35 mcg, and even more preferably not to exceed 25 mcg, with EE, conjugated estrogens, and 17-Beta estradiol being preferred estrogens. A weaker estrogen or an estrogen having antiestrogenic activity (such as SERMs) can be used or added as a second estrogen to any of the regimens of this paragraph. One version of the regimen of this paragraph has the total dosage of levonorgestrel in a cycle not to exceed 12 mg and alternatively not to exceed 10 mg and alternatively not to exceed 7.5 mg. Another version of the regimen of this paragraph has the total dosage of levonorgestrel in a cycle exceeding 10 mg, preferably exceeding 15 mg, more preferably exceeding 20 mg and even more preferably exceeding 30 mg or exceeding 40 mg. The cycle for the regimen is preferably 28 days, but other lengths are contemplated such as 20–35 days. The regimen of this paragraph can be mono-phasic, can be bi-phasic, or can have at least three phases, and includes triphasic regimens, but preferably is less than 5 phases. This invention provides administering the HRT regimen of this paragraph to a post-menopausal female who is no longer ovulating or to a climacteric female.

This invention contemplates HRT regimens for reducing the risk of ovarian cancer by increasing TGF-$\beta$ expression and/or apoptosis in the ovarian epithelium where the regimens have at least one phase with one or more of the daily dosages in one of the phases having at least 0.3 mg of norgestrel, alternatively at least 0.8, alternatively at least 1.2, and alternatively at least 1.8, and alternatively at least 2.5, or alternatively at least 4.0 or more. This phase of the regimen is administered at least one day, more preferable at least two days. or alternatively at least 3 days. Preferred ranges for the length of this phase are from 1–15 days, from 2–11 days, and from 3–7 days. The estrogen level used in this regimen preferably has no daily dosage exceeding 50 mcg EE dosage equivalent, and more preferably not to exceed 35 mcg, and even more preferably not to exceed 25 mcg, with EE, conjugated estrogens, and 17-Beta estradiol being preferred estrogens. A weaker estrogen or an estrogen having antiestrogenic activity (such as SERMs) can be used or added as a second estrogen to any of the regimens of this paragraph. One version of the regimen of this paragraph has the total dosage of norgestrel in a cycle not to exceed 12 mg and alternatively not to exceed 10 mg and alternatively not to exceed 7.5 mg. Another version of the regimen of this paragraph has the total dosage of norgestrol in a cycle exceeding 12 mg, preferably exceeding 18 mg, more preferably exceeding 25 mg and even more preferably exceeding 30 mg. The cycle for the regimen is preferably 28 days, but other lengths are contemplated such as 20–35 days. The regimen of this paragraph can be mono-phasic, can be bi-phasic, or can have at least three phases, and includes triphasic regimens, but preferably is less than 5 phases. This invention provides administering the HRT regimen of this paragraph to a post-menopausal female who is no longer ovulating or to a climacteric female.

This invention contemplates HRT regimens for reducing the risk of ovarian cancer by increasing TGF-$\beta$ expression and/or apoptosis in the ovarian epithelium where the regimens have at least one phase with one or more of the daily dosages in one of the phases having at least 0.3 mg of norethindrone acetate, alternatively at least 0.8, alternatively at least 1.2, and alternatively at least 1.8, and alternatively at least 3.0, or alternatively at least 4.0 or more. This phase of the regimen is administered at least one day, more preferable at least two days or alternatively at least 3 days. Preferred ranges for the length of this phase are from 1–15 days, from 2–11 days, and from 3–7 days. The estrogen level used in this regimen preferably has no daily dosage exceeding 50 mcg EE dosage equivalent, and more preferably not to exceed 35 mcg, and even more preferably not to exceed 25 mcg, with EE, conjugated estrogens, and 17-Beta estradiol being preferred estrogens. A weaker estrogen or an estrogen having antiestrogenic activity (such as SERMs) can be used or added as a second estrogen to any of the regimens of this paragraph. One version of the regimen of this paragraph has the total dosage of norethindrone acetate in a cycle not to exceed 12 mg and alternatively not to exceed 10 mg and alternatively not to exceed 7.5 mg. Another version of the regimen of this paragraph has the total dosage of norethindrone acetate in a cycle exceeding 12 mg, preferably exceeding 18 mg, more preferably exceeding 25 mg and even more preferably exceeding 35 mg. The cycle for the regimen is preferably 28 days, but other lengths are contemplated such as 20–35 days. The regimen of this paragraph can be mono-phasic, can be bi-phasic, or can have at least three phases, and includes triphasic regimens, but preferably is less than 5 phases. This invention provides administering the HRT regimen of this paragraph to a post-menopausal female who is no longer ovulating or to a climacteric female.

This invention contemplates HRT regimens for reducing the risk of ovarian cancer by increasing TGF-β expression and/or apoptosis in the ovarian epithelium where the regimens have at least one phase with one or more of the daily dosages in one of the phases having at least 0.2 mg of desogestrol, alternatively at least 0.5, alternatively at least 0.9, and alternatively at least 1.5, and alternatively at least 2.5, or alternatively at least 3.5 or more. This phase of the regimen is administered at least one day, more preferable at least two days or alternatively at least 3 days. Preferred ranges for the length of this phase are from 1–15 days, from 2–11 days, and from 3–7 days. The estrogen level used in this regimen preferably has no daily dosage exceeding 50 mcg EE dosage equivalent, and more preferably not to exceed 35 mcg, and even more preferably not to exceed 25 mcg, with EE, conjugated estrogens, and 17-Beta estradiol being preferred estrogens. A weaker estrogen or an estrogen having antiestrogenic activity (such as SERMs) can be used or added as a second estrogen to any of the regimens of this paragraph. One version of the regimen of this paragraph has the total dosage of desogestrol in a cycle not to exceed 12 mg and alternatively not to exceed 10 mg and alternatively not to exceed 7.5 mg. Another version of the regimen of this paragraph has the total dosage of desogestrol in a cycle exceeding 15 mg, preferably exceeding 25 mg, more preferably exceeding 30 mg and even more preferably exceeding 40 mg. The cycle for the regimen is preferably 28 days, but other lengths are contemplated such as 20–35 days. The regimen of this paragraph can be mono-phasic, can be bi-phasic, or can have at least three phases, and includes triphasic regimens, but preferably is less than 5 phases. This invention provides administering the HRT regimen of this paragraph to a post-menopausal female who is no longer ovulating or to a climacteric female.

This invention contemplates HRT regimens for reducing the risk of ovarian cancer by increasing TGF-β expression and/or apoptosis in the ovarian epithelium where the regimens have at least one phase with one or more of the daily dosages in one of the phases having at least 2.0 mg of dienogest or drosprirenone, alternatively at least 3.5, alternatively at least 4.5, and alternatively at least 5.5, and alternatively at least 7.0, or alternatively at least 8.0 or more. This phase of the regimen is administered at least one day, more preferable at least two days or alternatively at least 3 days. Preferred ranges for the length of this phase are from 1–15 days, from 2–11 days, and from 3–7 days. The estrogen level used in this regimen preferably has no daily dosage exceeding 50 mcg EE dosage equivalent, and more preferably not to exceed 35 mcg, and even more preferably not to exceed 25 mcg, with EE, conjugated estrogens, and 17-Beta estradiol being preferred estrogens. A weaker estrogen or an estrogen having antiestrogenic activity (such as SERMs) can be used or added as a second estrogen to any of the regimens of this paragraph. One version of the regimen of this paragraph has the total dosage of dienogest or drosprirenone in a cycle not to exceed 12 mg and alternatively not to exceed 10 mg and alternatively not to exceed 7.5 mg. Another version of the regimen of this paragraph has the total dosage of dienogest or drosprirenone in a cycle exceeding 15 mg, preferably exceeding 25 mg, more preferably exceeding 30 mg and even more preferably exceeding 50 mg. The cycle for the regimen is preferably 28 days, but other lengths are contemplated such as 20–35 days. The regimen of this paragraph can be mono-phasic, can be bi-phasic, or can have at least three phases, and includes triphasic regimens, but preferably is less than 5 phases. This invention provides administering the HRT regimen of this paragraph to a post-menopausal female who is no longer ovulating or to a climacteric female.

This invention contemplates HRT regimens for reducing the risk of ovarian cancer by increasing TGF-β expression and/or apoptosis in the ovarian epithelium where the regimens have at least one phase with one or more of the daily dosages in one of the phases having at least 7 mg of medroxyprogesterone acetate, preferably at least 10, more preferably 12, and even more preferably 20, and most preferably 30 or more. This phase of the regimen is administered at least one day, more preferable at least two days or alternatively at least 3 days. Preferred ranges for the length of this phase are from 1–15 days, from 2–11 days, and from 3–7 days. The estrogen level used in this regimen preferably has no daily dosage exceeding 50 mcg EE dosage equivalent, and more preferably not to exceed 35 mcg, and even more preferably not to exceed 25 mcg, with EE, conjugated estrogens, and 17-Beta estradiol being preferred estrogens. A weaker estrogen or an estrogen having antiestrogenic activity (such as SERMs) can be added to any of the formulations mentioned in this paragraph. One version of the regimen of this paragraph has the total dosage of medroxyprogesterone acetate in a cycle not to exceed 25 mg. Another version of the regimen of this paragraph has the total dosage of norgestimate in a cycle exceeding 40 mg, preferably exceeding 50 mg. The cycle for the regimen is preferably 28 days, but other lengths are contemplated such as 20–35 days. The regimen of this paragraph be mono-phasic, can be bi-phasic, or can have at least three phases, and includes triphasic regimens, but preferably is less than phases. This invention provides administering the HRT regimen of this paragraph to a post-menopausal female who is no longer ovulating or to a climacteric female.

This invention contemplates HRT regimens for reducing the risk of ovarian cancer by increasing TGF-β expression and/or apoptosis in the ovarian epithelium where the regimens have at least one phase with one or more of the daily dosages in one of the phases having a progestin at a dosage equivalent of at least 0.3 mg of levonorgestrel, alternatively at least 0.5, alternatively at least 1.0, and alternatively at least 1.5, and alternatively at least 2.0, or alternatively at least 3.0, or alternatively at least 4.0, or alternatively greater than 5.0. This phase of the regimen is administered at least one day, more preferable at least two days or alternatively at least 3 days. Preferred ranges for the length of this phase are from 1–15 days, from 2–11 days, and from 3–7 days. The estrogen level used in this regimen preferably has no daily dosage exceeding 50 mcg EE dosage equivalent, and more preferably not to exceed 35 mcg, and even more preferably not to exceed 25 mcg, with EE, conjugated estrogens, and 17-Beta estradiol being preferred estrogens. A weaker estrogen or an estrogen having antiestrogenic activity (such as SERMs) can be added to any of the formulations mentioned in this paragraph. One version of the regimen of this paragraph has the total dosage of progestin at a dosage equivalent in a cycle not to exceed 12 mg of levonorgestrel and alternatively not to exceed 10 mg dosage equivalent and alternatively not to exceed 7.5 mg dosage equivalent. Another version of the regimen of this paragraph has the total dosage of progestin at a dosage equivalent in a cycle exceeding 10 mg of levonorgestrel, preferably exceeding 15 mg dosage equivalent, more preferably exceeding 20 mg dosage equivalent and even more preferably exceeding 30 mg dosage equivalent or exceeding 40 mg. The cycle for the regimen is preferably 28 days, but other lengths are contemplated such as 20–35 days. The regimen of this paragraph can be mono-phasic, can be bi-phasic, or can have at least three phases, and includes triphasic regimens, but preferably is less than 5 phases. This invention provides administering the HRT regimen of this paragraph to a post-menopausal female who is no longer ovulating or to a climacteric female.

Any of the HRT regimens of this invention can be modified to include an additional progestin (preferably one having progestational effect per mg at least as high as one or more of the progestins listed as "strong" in this category in Table 4 and/or having antiestrogenic effect per mg at least as high as one or more of the progestins listed as "strong" in this category in Table 4), a Vitamin D component, or any other TGF-$\beta 2$ inducing agent. The agent can be put in one or more of the pills on the OCP regimen, including the otherwise placebo pills or daily dosages containing hormones.

The HRT regimens of this invention are formulated to increase the TGF-$\beta$ expression and/or apoptotic effect of the regimen in the manner as taught in this application. For example, the regimens of this invention include the HRT regimens described in Table 3, but modified to increase TGF-$\beta$ expression and/or apoptosis induction by increasing the level of progestin in one or more tablets in each cycle or by increasing the level of progestin in one or more tablet one of the months in a three month cycle or by adding a different progestin in one or more of the tablets. Alternatively, another non-progestin agent could be added to one or more of the tablets to increase TGF-$\beta$ expression and/or apoptotic inductionor the formulation could be modified by changing the progestin to one which is more potent for TGF-$\beta$ upregulation or apoptotic effect.

One embodiment of this invention further contemplates these use in the HRT regimens of this invention of progestins having progestational activity per unit dosage at least as high as one or more of the progestins listed as "strong" in this category in Table 4. Further, the progestins having progestational activity as high as such listed progestins in uterine and ovarian epithilium tissues can be preferred in this aspect of the invention. Further, the progestins having antiprogestational activity with respect to the breast tissues can be another preferred aspect of this invention. Such progestins are useful for any of the HRT regimens described herein either as the sole progestin or as a second progestin added to one or more of the daily dosages in an amount sufficient to protect the breast tissues. When used as a second progestin in one more daily doses of a regimen, the dosage of the second progestin is provided in one embodiment at a daily dosage equivalent of at least 0.125 mg of levonorgestrel, alternatively at least 0.25, alternatively at least 0.5, and alternatively at least 1.0, and alternatively at least 2.0, or alternatively at least 3.0 or more. (Preferably, the HRT regimens utilize a progestin having a progestational effect per mg as strong as levonorgestrel and/or an antiestrogenic effect per mg as strong as levonorgestrel.)

Further, the invention contemplates the use, in any of the HRT regimens of this invention of progestins having antiestrogenic effect per mg at least as high as one or more of the progestins listed as "strong" in that category in Table 4. Particularly, progestins having antiestrogenic activity with respect to the ovarian epithilium and/or antiestrogenic activity with respect to the uterus and/or antiestrogenic activity with respect to the breast can be used for regimens of this invention, including any of the OCP regimens described herein either as the sole progestin or as a second progestin added to one or more of the daily dosages in an amount sufficient to protect the breast tissues, the ovarian epithilium and/or the uterus. When used as a second progestin in one or more of the daily doses of a regimen, the dosage of the second progestin is provided in one embodiment at a daily dosage equivalent of at least 0.125 mg of levonorgestrel, alternatively at least 0.25, alternatively at least 0.5, and alternatively at least 1.0, and alternatively at least 2.0, or alternatively at least 3.0 or more. (Preferably, the HRT regimens utilize a progestin having a progestational effect per mg as strong as levonorgestrel and/or an antiestrogenic effect per mg as strong as levonorgestrel.)

Another aspect of this invention is the use of statements in conjunction with HRT regimens stating that the HRT regimens are effective for preventing or reducing the risk of developing epithelial ovarian cancer. The statement can be in the form of a written statement or an oral statement. The statement can be in the form of a written statement attached to packing inserts or used as a label in connection with the product.

This invention further contemplates the use of statements with OCP or HRT regimens that the formulations have TGF-$\beta$ inducing and/or apoptosis-agent inducing effects or that the formulations have been designed to provide enhanced protection against ovarian cancer. The statements can be written or oral. The statements can be in the form of a written statement provided in connection with the product, including, for example, package inserts and/or label.

This invention includes prescribing HRT regimens, including the HRT regimens described herein, in postmenopausal women who are no longer ovulating for the purpose of reducing or preventing the risk of ovarian cancer. This invention further includes prescribing HRT regimens, including the HRT regimens described herein, in climacteric women for the purpose of reducing or preventing the risk of ovarian cancer.

The invention provides preferred regimens for prevention of ovarian epithelial cancer in postmenopausal women in need thereof who are no longer ovulating and do not require a regime which is contraceptive but may be desirous of hormone replacement therapy. For any of the HRT regimens of this invention which include an estrogen component, there is desired sufficient estrogen product to provide both bone protection and cardiac protection and decrease risk of Alzheimer's and decrease vasomotor symptoms. Any suitable estrogen product can be used which provides these therapeutic effects. It is preferred in accordance with another aspect of this invention that the estrogen used in the HRT regimens of this invention have anti-estrogenic effect with respect to the ovarian epithilium and/or have anti-estrogenic effect with respect to the uterus and/or have anti-estrogenic effect with respect to the breast.

It is known that estrogen products having different affinities and activities with different estrogen receptors (ERα and Erβ) and different subspecies of those receptors can be selected to provide the desired estrogenic effects. However, the anti-estrogen products can be preferred. Thus, the preferred estrogens include selective estrogen receptor modulators ("SERM"). For example, those compounds include Clomiphene, Tamoxifen (4 OH tamoxifen), Nafoxidene, Droloxifene, Toremifene, Idoxifene, Raloxifene, and Isoflavones (phytoestrogens). This invention contemplates using any of the above estrogens in HRT formulations of the invention, for example, as complete or partial substitutes for the estrogens in the HRT formulations identified in this application.

A further exemplary regimen includes doses of progestin product with estrogen product at a ratio of greater than 1:1 by weight in norethindrone/ethinyl estradiol equivalent doses, or a ratio of greater than 50:1 or 100:1. It is also contemplated that the most desirable mode of administration may be administering the progestin product for a brief period sufficient to induce TGF-β expression and/or produce apoptotic turnover followed by repeated dosing periods at selected intervals adequate to prevent malignant transformations. A presently preferred progestin product is levonorgestrel or the 19-nortestosterone derivatives. The most preferable progestin product for administration would be a product that maximizes TGF-β effect and/or the apoptotic turnover of ovarian epithelial cells and minimizes any side effects.

Yet another aspect of the present invention involves administration of TGF-β-1, TGF-β-2 or TGF-β-3 directly to the female subject. This invention contemplates the potential delivery of TGF-β specifically to the ovarian epithelium by using smart liposomes and other advanced drug delivery systems that selectively are targeted to the ovarian epithelium. This method of delivery would result in the promotion of the absorption of TGF-β in the ovarian epithelial cells.

The present invention yet further provides a novel use of progestin product in preparation of a non-contraceptive medicament for prevention of ovarian cancer in female subjects, as well as a novel use of progestin product in preparation of a medicament for prevention of ovarian cancer in infertile female subjects.

The invention also provides therapeutic compositions for promotion of TGF-β response and/or apoptosis of ovarian epithelial tissue for prevention of ovarian cancer, compositions which comprise a non-progestin/non-estrogen TGF-β inducing agent and/or a non-progestin/non-estrogen apoptosis promoting agent selected from the group consisting of the retinoids, dietary flavanoids, anti-inflammatory drugs, monoterpenes, S-adenosyl-L-methionine, selenium and vitamin D compounds.

Retinoids are natural derivatives and synthetic analogues of vitamin A. They are particularly interesting as chemopreventive agents because of their diverse cellular effects, including inhibition of cellular proliferation, induction of cellular differentiation, induction of apoptosis, cytostatic activity, ability to inhibit growth factor synthesis, and ability to affect immunity and extracellular matrix formation. The use of vitamin A analogues is limited by the requirement for large pharmacological doses in order to reach therapeutic efficacy. High dosages of naturally occurring retinoids produce significant side effects.

By modifying the basic retinoid structure, analogues with reduced toxicity have been developed. An example of such a compound is Fenretinide N-(4-hydroxyphenyl) retinamide, a retinamide derivative of vitamin A, which is a promising chemopreventive compound with therapeutic efficacy in a variety of carcinogenesis models. Fenretinide (4-HPR) is currently being evaluated in clinical trials as a chemopreventive agent for oral leukoplakia, breast and lung cancer. This compound can be used in any of the formulations of this invention mentioning the use of retinoids.

Retinoids have a basic molecular structure consisting of a cyclic end group, a polyene side chain and polar end group. Chemical manipulation of the polar end group and the polyene side chain produced the first-generation synthetic retinoids. The most widely studied of these molecules are tretinoin in vitro and isotretinoin (13-cis-retinoic acid) in vivo. The retinamides, such as fenretinide (4HPR), or N-(4-hydroxyphenyl) retinamide, are a group of first-generation retinoids in which the terminal carboxyl group of retinoic acid is replaced by an N-substituted carboxyamide group. The second generation retinoids were developed by altering the cyclic end group. The prototype second-generation molecule is etretinate. Cyclization of the polyene side chain has produced the retinoidal benzoic acid derivatives, or arotinoids. The arotinoid TTNPB and its ethylester (R013-6298) are less toxic and over 1000 times more potent than first-or second-generation retinoids in several standard screening tests.

Retinoids include, for example, retinoic acid, N-(4-hydroxyphenl) retinamide-O-glucuronide, N-(4-hydroxyphenyl) retinamide, O-glucuronide conjugates of retinoids, N-(4-hydroxyphenyl) retinamide and its glucuronide derivative, retinyl-B-glucuronide, the glucuronide conjugates of retinoic acid and retinol, tretinoin, etretinate, arotinoid, isotretinoin, retinyl acetate, acitretin, adapalene, and tazarotene. This invention contemplates using these retinoids in any of the regimens of this invention mentioning the use of retinoids, including any of the HRT and OCP regimens of this invention.

There is evidence for a significant role of retinol and its derivatives in the ovary. Vitamin A is essential for the maintenance of normal reproductive functions in both female and male rats. Of the human organ studies, the ovary has the highest concentration of cellular retinol binding protein and expresses nuclear retinoic acid receptor. It has also been reported that the growth of human ovarian carcinoma cell lines and normal human ovarian epithelial cells may be inhibited by TGF-β. There is some evidence to suggest that the growth inhibitory effect of retinoids on some cells is mediated by induction of secretion of specific isoforms of TGF-β. The mechanisms underlying antitumor effects have not been fully elucidated.

This invention contemplates using any of the retinoids in any of the regimens of this invention mentioning the use of retinoids, including regimens with progestins, including in single unit dosages. The invention further includes using retinoids in HRT and/or oral contraceptive formulations and regimens. This invention further contemplates using one or more of the retinoids in formulations and/or regimens without progestins. The retinoids can be combined in a regimen and/or can be combined in a single unit dosage with one or more agents, including estrogens, dietary flavanoids, anti-inflammatory drugs, selenium compounds, monoterpenes, S-adenosyl-L-methionine, vitamin D compounds and/or other agents capable of inducing apoptosis in ovarian epithelial cells. Such combinations can be used in HRT and/or contraceptive regimens, and the combination can be found in single unit dosages. The preferred retinoids are those capable of inducing apoptosis in ovarian epithelial cells. Suitable retinoids can be tested for the ability to induce apoptosis using the tests similar to those described herein for progestins. The most preferred product for administration would be an agent that provides the greatest rate of TGF-$\beta$ response in ovarian epithelial cells with the least side effects, and/or the greatest rate of apoptosis of ovarian epithelial cells with the least side effects. The preferred daily dosage of 4HPR or any other retinoid is at least 200 mg of a 4HPR equivalent dosage (equivalent in terms of either retinoidal potency or ability to induce apoptosis and/or increased TGF-$\beta$ expression in ovarian epithelial cells), with at least 400 mg being more preferred, at least 800 mg even more preferred, and at least 1600 mg even more preferred.

The term "anti-inflammatory drug" includes both steroidal drugs containing cortisone or its derivatives and non-steroidal anti-inflammatory drugs (NSAIDs), which do not contain cortisone or its derivatives. The corticosteroids suppress both acute and chronic phases of inflammatory disorders making them powerful anti-inflammatory drugs. They inhibit cytokine production and the migration and activation of inflammatory cells and are especially involved in carbohydrate, protein, and fat metabolism. Corticosteroids may also induce lymphocyte apoptosis. Corticosteroids are frequently used as part of the treatment for numerous conditions including severe allergies or skin diseases, asthma, and arthritis. The administration of corticosteroids is problematic, however, because in addition to reducing inflammation these agents also suppress immune system response and can retard various aspects of essential cellular repair processes.

Included among the corticosteroids are beclomethasone dipropionate, budesonide, flunisolide, fluticasone propionate, triamcinolone acetonide, methylprednisolone, prednisolone, prednisone, halobetasol, mometasone, hydrocortisone, desondide, flumethasone pivalate, fluocinolone acetonide, alclometasone dipropionate, desonide, hydrocortisone valerate, clocortolone pivalate, halobetasol propionate, clobetasol propionate, betamethasone, diflorasone diacetate, mometasone furoate.

The NSAIDs, which include aspirin, are the most commonly used drugs in the world, primarily because of they tend to reduce swelling, inflammation, pain, and sometimes fever, without many of the side effects associated with the steroidal drugs. NSAIDs produce their beneficial results by inhibiting the enzyme cyclooygenase (COX), a rate-limiting enzyme that synthesizes prostaglandins. These prostaglandins affect aspects of inflammation, renal blood flow, hemostasis, and gastric cytoprotection. Therefore, use of NSAIDs can cause gastrointestinal (GI) complications such as gastric and duodenal ulcers and may also interfere with blood's clotting ability. Although the occurrence of these side effects is relatively small, in the 2–4% range, because of the extremely high usage of these compounds, any adverse effects can affect a large number of people and cause significant expense.

Two COX isoforms are found in the body. The COX-1 isoform is expressed constitutively in the body and is primarily involved in the production of prostaglandins that promote platelet aggregation and that contribute to several of the homeostatic functions in the GI tract and the kidneys. For example, COX-1 is the predominate form of COX in GI tract mucosa. It is the inhibition of COX-1 that creates many of the organ-specific toxicity complications of NSAIDs. COX-2 is the inducible form of COX and is upregulated by cytokines at inflammatory sites. COX-2 is dynamically expressed in response to local injury, but also seems to promote GI mucosal healing of chemically induced injuries.

Traditional prescription and over the counter NSAIDs including aspirin, ibuprofen, katoprofen, naproxen, fenoprofen, flurbiprofen, oxaprozin, piroxicam, sulindac, mefenamic acid, meclofenamate, diclofenac, diclofenac, etodolac, indomethicin, ketorolac, tolmetin, nabumetone, salsalate, and meloxicam tend to inhibit both COX-1 and COX-2. More recent drugs like celecoxib and rofecoxib are COX-2 selective inhibitors meant to avoid many of the GI tract complications that occur with COX-1 inhibitors.

This invention contemplates using any of the anti-inflammatory drugs, both steroidal and NSAIDs, in any of the regimens of this invention mentioning the use of anti-inflammatory drugs, including regimens with progestins, including in single unit dosages. The invention further includes using anti-inflammatory drugs in HRT and/or oral contraceptive formulations and regimens. This invention further contemplates using one or more of the anti-inflammatory drugs in formulations and/or regimens without progestins. The anti-inflammatory drugs can be combined in a regimen and/or can be combined in a single unit dosage with one or more agents, including estrogens, dietary flavanoids, retinoids, monoterpenes, S-adenosyl-L-methionine, selenium, vitamin D compounds and/or other agents capable of inducing apoptosis in ovarian epithelial cells. Such combinations can be used in HRT and/or contraceptive regimens, and the combination can be found in single unit dosages. The preferred anti-inflammatory drugs are those capable of inducing apoptosis in ovarian epithelial cells. Suitable anti-inflammatory drugs can be tested for the ability to induce apoptosis using the tests similar to those described herein for progestins. The most preferred product for administration would be an agent that provides the greatest rate of TGF-$\beta$ response in ovarian epithelial cells with the least side effects, and/or the greatest rate of apoptosis of ovarian epithelial cells with the least side effects. The preferred daily dosage of celecoxib or any other selective inhibitor anti-inflammatory drugs is at least 50 mg of a celecoxib equivalent dosage (equivalent in terms of either anti-inflammatory potency or ability to induce apoptosis and/or increased TGF-$\beta$ expression in ovarian epithelial cells), with at least 100 mg being more preferred, at least 200 mg even more preferred and at least 400 mg even more preferred. A preferred daily dosage of ibuprofin or other anti-inflammatory drugs is at least 100 mg of an ibuprofen equivalent dosage (equivalent in terms of either anti-inflammatory potency or ability to induce apoptosis and/or increased TGF-$\beta$ expression in ovarian epithelial cells), with at least 200 mg being more preferred, at least 400 mg even more preferred and at least 800 mg even more preferred.

Dietary flavanoids include phytoestrogens which are compounds found in plants that exhibit estrogenic effects on the body. There are three primary classes of phytoestrogens—isoflavones, lignans, and coumestans. Similar to estrogen, these compounds affect the central nervous system, induce estrus, and stimulate female genital tract growth. More broadly, these compounds also include chemicals that have estrogen suggestive effects including induction of specific estrogen-responsive geneproducts, stimulation of estrogen receptor (ER) positive breast cancer cell growth, and binding to ER's. Phytoestrogens are structurally similar to natural and synthetic estrogens and antiestrogens with diphenolic structures. See the figure below:

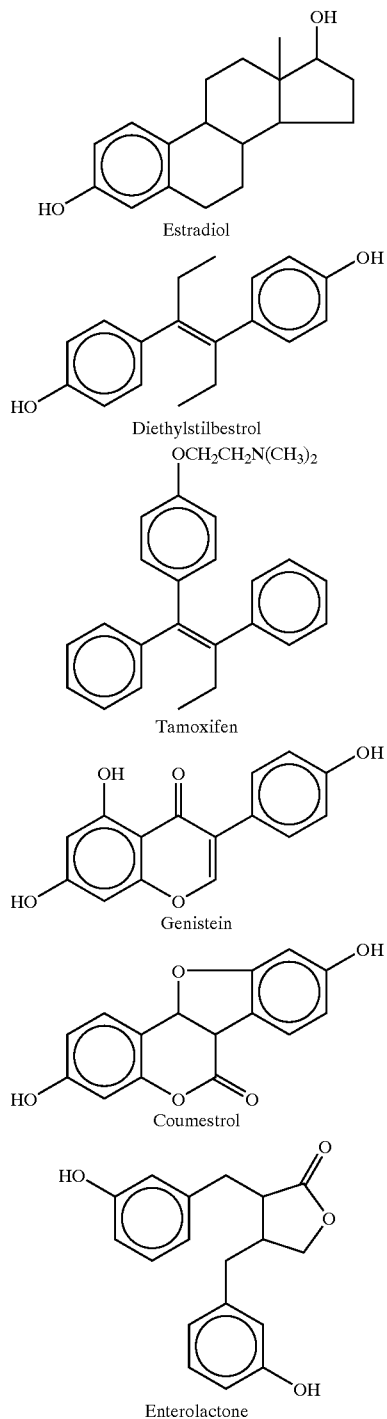

FIG. 1. Structures of estradiol (natural estrogen), diethylstilbestrol (synthetic estrogen), and tamoxifen (synthetic antiestrogen) shown for comparison with genistein (isoflavone), coumestrol (coumestan), and enterolactone (lignan).

Well over 300 different types of plants have been identified as possessing sufficient estrogenic activity to induce estrus in animals. Soybeans and soy containing foods are by far the most significant dietary source of phytoestrogens, while clover, chickpeas and various other legumes, bluegrass, alfalfa, split peas, kala chana seeds, pinto bean seeds, oilseeds such as flaxseed, dried seaweeds, and toothed medic also contain appreciable amounts. Isoflavones and coumestans are the most prevalent phytoestrogen compounds found in these and most other plants.

Isoflavones, lignans, and coumestans all include many different chemical compounds. For example, soybeans contain three main isoflavones that are each found in four chemical forms. The unconjugated forms, or aglycones, are daidzein, genistein, and glycitein. Each of these isoflavones is also found as a glucoside (daidzin, genistin, and glycitin), acetylglucoside and malonylglucoside. Processing of soy products is known to cause significant changes in the quantity and type (form) of isoflavones found in these foods. When soy flour is minimally processed it primarily contains the 6"-O-malonyladaidzin and 6"-O-malonylgenistin isomers. Further processing, such as heat-treating, will transform the malonyl isoflavones to their acetyl forms. These soy isoflavones have about one third as potent an agonist effect on the ER as estradiol but are only 0.001 as potent as estradiol when it comes to affecting the ER. If essence, the soy isoflavones are basically a type of selective ER modulator. Burke et al, Soybean Isoflavones as an Alternative to Traditional Hormone Replacement Therapy: Are We There Yet?, J. Nutr., 130: 664S–665S, 2000.

Although lignans have not been shown to induce estrus, they do produce other estrogen-like actions. Lignans found in humans come from the bacterial conversion of plant lignans in the gastrointestinal (GI) tract. The plant lignans, secoisolariciresinol and matairesinol, are the dietary precursors of enterodiol and enterolactone.

Isoflavones are similarly metabolized by bacteria in the GI tract. The isoflavone daidzein is metabolized to dihydrodaidzein, which is further metabolized to both equol and O-desmethylangolensin (O-DMA). Genistein is similarly metabolized to dihydrogenistein and then to 6'hydroxy-O-DMA.

Both isoflavones and lignans are absorbed and utilized through a series of conjugation/deconjugation steps with considerable variation in the actual percent metabolized depending on the individual and the type of processing that the food products have undergone. Isoflavones have been found in varying concentrations in urine, plasma, liver, lunge, kidney, brain, testis, spleen, skeletal muscle, and heart. Phytoestrogens have been shown to influence sexual differentiation, bind to the ER, affect the growth of estrogen dependent cells, affect the menstrual cycle and concentrations of reproductive formones in premenopausal women, increase vaginal cell maturation in postmenopausal women, improve cardiovascular risk factors, reduce LDL cholesterol and triglycerides, increase bone density, and potentially reduce osteoporosis associated with menopause. Kurzer, M. and Xiz Xu, Dietary Phytoestrogens, Annu. Rev. Nutr., 17:353–81, 1997. Studies have shown that countries consuming large amounts of isoflavones through soy and soy products have a markedly lower chronic disease burden than countries where relatively little soy is consumed. For example, cardiovascular disease and breast cancer mortality rates are four times lower for Japanese women than U.S. women. Endometrial cancer rates are also lower. Burke et al.

Phytoestrogens have also shown other chemopreventive activity with effects seen on leukemia and melanoma; human prostate, stomach, colon, and esophageal cancer; and rat mammary epithelial cells. This chemopreventive activity of phytoestrogens is generally believed to occur through the promotion of terminal differentiation of human tumor cells, which in turn inhibits cancer cell proliferation; inhibition of the cellular proliferation via effects on tyrosine kinases; inhibition of DNA topoisomerases' DNA replication promoting activity; enhancement of angiogenesis; antioxidant effects; and programmed cell death via apoptosis. The inhibition of cell proliferation by phytoestrogens may also involve transforming growth factor 1 signaling which includes cell specific activity and the attenuation of passage through cell cycle checkpoints via transcriptional regulation of selected proteins. Kim et al, *Mechanisms of Action of the Soy Isoflavone Genistein: Emerging Role for its Effects via Transforming Growth Factor B Signaling Pathways, Am. J. Clin Nutr.*, 68(suppl): 1418S–25S, 1998.

Although there are a large number of beneficial effects, there may also be some detrimental side effects from the consumption of large amounts of dietary phytoestrogens. It is still not entirely known what role these compounds play in the steroid hormone balance or whether they may compete with normal steroids and drugs. Most evidence though suggests that phytoestrogens are well tolerated. For example, there is no evidence of bleeding, breast tenderness or gastrointestinal symptoms in postmenopausal women, which when looked at in connection with the estrogen like effects of phytoestrogens has led to the suggested use of phytoestrogens in hormone replacement therapy. Phytoestrogens further include, triein, formonoetin, coumestrol, and biochanin A.

This invention contemplates using any of the dietary flavanoids in any of the regimens of this invention mentioning the use of dietary flavanoids, including regimens with progestins, including in single unit dosages. The invention further includes using dietary flavanoids in HRT and/or oral contraceptive formulations and regimens. This invention further contemplates using one or more of the dietary flavanoids in formulations and/or regimens without progestins. The dietary flavanoids can be combined in a regimen and/or can be combined in a single unit dosage with one or more agents, including estrogens, retinoids, anti-inflammatory drugs, selenium compounds, monoterpenes, S-adenosyl-L-methionine, vitamin D compounds and/or other agents capable of inducing apoptosis in ovarian epithelial cells. Such combinations can be used in HRT and/or contraceptive regimens, and the combination can be found in single unit dosages. The preferred dietary flavanoids are those capable of inducing apoptosis in ovarian epithelial cells. Suitable dietary flavanoids can be tested for the ability to induce apoptosis using the tests similar to those described herein for progestins. The most preferred product for administration would be an agent that provides the greatest rate of TGF-$\beta$ response in ovarian epithelial cells with the least side effects, and/or the greatest rate of apoptosis of ovarian epithelial cells with the least side effects. The preferred daily dosage of dietary flavanoids, especially isoflavones, is at least 10 mg, with at least 20 mg being more preferred, at least 50 mg even more preferred and 80 mg even more preferred. The preferred daily dosage of dietary flavanoids, especially isoflavones, is one that achieves a peak plasma level at least in the nanomolar range, or more preferably at least $1.0 \times 10^{-8}$ molar, even more preferably at least $1.0 \times 10^{-7}$ molar, even more preferably at least $1.0 \times 10^{-6}$ molar, and even more preferably at least $1.0 \times 10^{-5}$ molar.

Monoterpenes are nonnutritive dietary components found in the essential oils of citrus fruits and other plants. For example, orange oil naturally consists of 90–95% d-limonene. Monoterpenes are any of a class of terpenes $C_{10}H_{16}$ containing two isoprene units per molecule and are significantly responsible for the unique and fragrant smell of many plants. Monoterpenes function physiologically as chemoattractants or chemorepellents. These 10 carbon isoprenoids are not produced by mammals, fungi or other species but are derived from the mevalonate pathway in plants. D-limonene, the primary monoterpene constituent found in citrus fruits, peppermint and other plants, is formed by a limonene synthase catalyzed reaction where geranylpyrphosphate undergoes cyclization. Many other oxygenated monocyclic monoterpenes such as perillyl alcohol, perillaldehyde, menthol, carveol and carvone are then formed from limonene.

Many different plants can serve as dietary sources of monoterpenes. From citrus peel essential oils, caraway, and dill one can extract d-limonene; carvone from caraway and spearmint; perillyl alcohol from cherry and spearmint; and geraniol from lemongrass oil, a constituent in some herbal teas. Because of its distinctive fragrance and flavor, d-limonene is commonly used to give soaps, cosmetics, and various cleaning products a citrus smell and to give soft drinks, ice cream, fruit juices, pudding, and an assortment of baked goods additional flavor. Because of its high levels of d-limonene, orange essential oil is commercially available food flavoring agent. Humans therefore regularly consume or are exposed to monoterpenes in both their diet and environment. Limonene is metabolized to oxygenated metabolites in humans. In humans the three major serum metabolites of limonene produced are perillic acid, dihydroperillic acid, and limonene-1,2-diol. Limonene and/or its metabolites have been detected in serum, urine, lung, liver, and many other tissues. Higher concentrations are usually detected in adipose tissue and mammary gland than in less fatty tissues.

When limolene is administered either in pure form or as orange peel oil, it has inhibited the development of chemically induced rodent mammary, lung, skin, liver, and forestomach cancers. Limonene has also been shown to reduce the incidence of spontaneous lymphomas and inhibit the development of spontaneous neoplasms in mice. Furthermore, carvone, the primary monoterpene found in caraway seed oil, tends to prevent chemically induced lung and forestomach carcinoma development. The acyclic dietary monoterpene geraniol has in vivo antitumor activity against melanoma cells, hepatoma, and murine leukemia. In addition, perillyl alcohol has promotion phase chemopreventive activity against chemically induced rat liver cancer.

Monoterpene agents may have cancer blocking and/or suppressing activity. Limonene has been shown to have mammary cancer blocking activity by inducing total cytochrome P450, epoxide hydratase, glutathione-S-transferase, and UDP-glucuronyl transferase, thus leading to the urinary excretion of cancer causing agents. The blocking process tends to prevent chemical carcinogens from interacting with DNA, thus modulating carcinogen metabolism to less toxic forms.

The cancer suppressing chemopreventive activity of monoterpenes during the promotion phase of mammary and liver carcinogenesis may be due to inhibition of tumor cell proliferation, acceleration of the rate of tumor cell death and/or induction of tumor cell differentiation. The chemopreventive activity of perillyl alcohol during the promotion phase of liver carcinogenesis is associated with a marked increase in tumor cell death by apoptosis, or programmed cell death. Monoterpenes also have multiple pharmacologic effects on mevalonate metabolism, which could account for some of their tumor suppressive activity.

Other common monoterpenes include sobreol and menthol. In general, monoterpenes and their derivatives have been shown marked chemopreventive activity.

This invention contemplates using any of the monoterpenes in any of the regimens of this invention mentioning the use of monoterpenes, including regimens with progestins, including in single unit dosages. The invention further includes using monoterpenes in HRT and/or oral contraceptive formulations and regimens. This invention further contemplates using one or more of the monoterpenes in formulations and/or regimens without progestins. The monoterpenes can be combined in a regimen and/or can be combined in a single unit dosage with one or more agents, including estrogens, dietary flavanoids, retinoids, anti-inflammatory drugs, selenium compounds, S-adenosyl-L-methionine, vitamin D compounds and/or other agents capable of inducing apoptosis in ovarian epithelial cells. Such combinations can be used in HRT and/or contraceptive regimens, and the combination can be found in single unit dosages. The preferred monoterpenes are those capable of inducing apoptosis in ovarian epithelial cells. Suitable monoterpenes can be tested for the ability to induce apoptosis using the tests similar to those described herein for progestins. The most preferred product for administration would be an agent that provides the greatest rate of TGF-β response in ovarian epithelial cells with the least side effects, and/or the greatest rate of apoptosis of ovarian epithelial cells with the least side effects. The preferred daily dosage of monoterpenes is one that achieves a peak plasma level at least in the nanomolar range, or more preferably at least $1.0 \times 10^{-8}$ molar, even more preferably at least $1.0 \times 10^{31\ 7}$ molar, even more preferably at least $1.0 \times 10^{-6}$ molar, and even more preferably at least $1.0 \times 10^{-5}$ molar.

Selenium is an extremely potent, essential micronutrient in humans and other species. At levels of ~0.1 ppm (mg/kg) selenium serves as a micronutrient but becomes toxic once levels of 8–10 ppm are reached. Selenium compounds can be taken in foods such as selenium-enriched garlic or yeast (there is some evidence suggesting lower toxicity for some organic forms of selenium) or as synthetic selenium compounds. When selenium compounds, primarily selenite or selenomethionine because of their commercial availability, are used in levels above the dietary requirement, but below toxic levels (1–5 ppm), they have been known to suppress carcinogenesis. Ip, *Lessons from Basic Research in Selenium and Cancer Prevention*, *J. Nutr.* 128: 1845–1854, 1998. The tumor inhibiting effects have been noted in the mammary glands, skin, pancreas, colon, liver, and esophagus. Because of the high potency of most selenium compounds, there is a strong dose-dependent response. Many of the beneficial characteristics can be achieved at doses below the toxic level.

Studies with cell cultures have shown that selenium may reduce the effect of several mutagens particularly by inhibiting the initiation phase of these carcinogens. A variety of potential actions have been suggested as the mechanism of action behind this anticarcinogenic activity. These suggestions include effects on the immune and endocrine systems, initiation of apoptosis, production of cytotoxic selenium metabolites, alteration of the metabolism of carcinogens, inhibition of protein synthesis and specific enzymes, and protection against free radicals and oxidative damage through the action of selenium incorporation into glutathione peroxidase as an antioxidant. *Prevention of Prostate Cancer, The National Cancer Institute of the National Institutes of Health PDQ Prevention for Health Professionals on WebMD.com*, June 2000, http://my.webmd.com/content/dmk/dmk_article_5962880. The beneficial effects of selenium compounds seem to be greatly increased when the compounds selectively alter metabolic pathways as opposed to tissue proteins.

Other selenium compounds including selenobetaine, Se-methylselenocysteine, and selenobetaine methyl ester have been found to be equal to or greater than selenite or selenomethionine in cancer chemoprevention. Some of this increase in anticarcinogenic efficacy may be because these compounds have been shown to induce cell death predominantly by apoptosis in the in vitro system, while selenite is known to cause cell death by primarily by necrosis or acute lysis, although it too promotes apoptosis. In contrast, dimethylselenoxide and trimethylselenonium have much lower chemopreventive activity. Dimethylselenoxide is known to undergo rapid reduction to dimethylselenide which is then exhaled, while trimethylselenonium is excreted in urine. Precursor selenium compounds that are likely to have good anticarcinogenic activity are the ones that are able to produce a steady stream of monomethylated metabolite. Some findings have shown that very high levels of selenium can enhance programmed cell death thereby impairing cellular proliferation and potentially retarding tumor growth.

Selenium compounds further include, selenocyanates, selenocystine, monomethylated selenium, selenoethionine, and aromatic selenium compounds (e.g. p-methoxybenzeneselenol, benzylselenocyanate, 1,4-phenylene-bis (methylene) selenocyanate, triphenylselenonium, diphenylselenide, and methylphenylselenide). See the figure below:

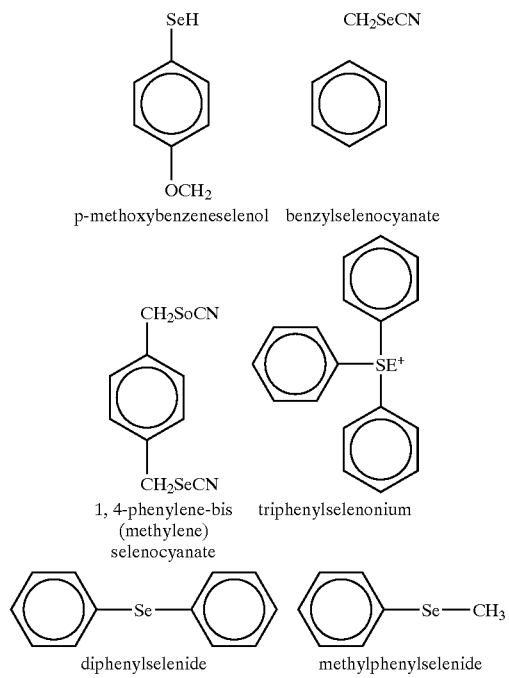

FIG. 2. Structures of aromatic selenium compounds

This invention contemplates using any of the selenium compounds in any of the regimens of this invention mentioning the use of selenium compounds, including regimens with progestins, including in single unit dosages. The invention further includes using selenium compounds in HRT and/or oral contraceptive formulations and regimens. This invention further contemplates using one or more of the selenium compounds in formulations and/or regimens without progestins. The selenium compounds can be combined in a regimen and/or can be combined in a single unit dosage with one or more agents, including estrogens, dietary flavanoids, retinoids, anti-inflammatory drugs, monoterpenes, S-adenosyl-L-methionine, vitamin D compounds and/or other agents capable of inducing apoptosis in ovarian epithelial cells. Such combinations can be used in HRT and/or contraceptive regimens, and the combination can be found in single unit dosages. The preferred selenium compounds are those capable of inducing apoptosis in ovarian epithelial cells. Suitable selenium compounds can be tested for the ability to induce apoptosis using the tests similar to those described herein for progestins. The most preferred product for administration would be an agent that provides the greatest rate of TGF-β response in ovarian epithelial cells with the least side effects, and/or the greatest rate of apoptosis of ovarian epithelial cells with the least side effects. The preferred daily dosage of selenium is at least 50 mg, at least 100 mg being more preferred, at least 200 mg even more preferred, at least 400 mg even more preferred, at least 800 mg yet more preferred and at least 1600 mg most preferred. Any of the compositions described herein may be administered by a variety of means including orally and by injection but may also be administered in the form of sustained release products by means selected from the group consisting of implants and transdermal patches. These compounds can be administered with progestins and/or estrogens in single unit dosages or as part of regimens with other compounds.

In addition to the delivery system in use for TGF-β described above, delivery systems can alternatively or in addition be used with other compounds. For example, the progestin compounds with this invention could be packaged in a smart liposome delivery system.

Other preferred ways of delivering progestins and/or other compounds of this invention to the ovarian surface would include surgery, wherein the TGF-β molecules themselves, or other compounds such progestins, are coated directly on the surface of the ovary. Other delivery systems for the progestin product would include direct placement of the compounds in the vagina and/or in the uterus. Such preferred methods include creams, slow release capsules or pessaries, or an intrauterine IUD that releases the drugs. These preferred methods of delivery minimize the risk of adverse side effects to other organs in the body.

According to each of the preceding and following aspects of the invention comprising multiphase regimens for administration of progestin products the additional TGF-β inducing agent and/or apoptosis promoting agent may be administered simultaneously with the progestin product or alternatively may be administered during a phase when the progestin product is not administered.

Another aspect of this invention contemplates the administration of agents to women for prevention of ovarian cancer made and/or formulated by a particular method. The method comprising testing an agent for TGF-β upregulation. Specifically, candidate agents, such as various progestins and other compounds as mentioned herein in this application, are tested by methods described in Examples 6, 7, 8, 9, 12 and/or 13 to determine their ability to induce biologic effects in ovarian epithelial cells. Based on the results of the study, the most potent candidates are selected with a consideration of side effects. A potential comparison to use would be to compare the ability of a compound to upregulate TGF-β response in ovarian epithelial cells as compared to levonogestrel on a per mg basis. One aspect of the invention is to test for TGF-β response in ovarian epithelial cells as compared to levonogestrel and to select an agent because based on the criteria that the TGF-β response for the agent is greater than or equal to for levonogestrel on a per mg basis. The method further comprises subsequently selling and/or prescribing the resulting composition and/or regimen for administration to a female subject in need thereof.

The invention further contemplates a method of selecting of the appropriate agent for a regimen for reducing the risk of epithelial ovarian cancer. The method comprises selection of an agent which maximally induces or increases TGF-β-3 upregulation in the ovarian epithelium. In the alternative, the invention contemplates that the optimal compound would be an agent that maximally upregulates TGF-β-1 in the ovarian epithelium. In the further alternative, the invention contemplates that the compound would be selected based on its ability to upregulate TGF-β-2 expression in the ovarian epithelium. Finally, it is contemplated that as another aspect of this invention that the candidate is selected based on its ability to upregulate the combination of TGF-β-1, TGF-β-2 and TGF-β-3, collectively, in the ovarian epithelium. In each instance, levonorgestrel can be used as a standard for comparison. In preferred embodiments, the agent is selected as being as effective as levonorgestrel in its TGF-β upregulation effect.

Further exemplary methods of preventing ovarian cancer according to the invention (e.g., methods beyond the use of estrogen and progestin products as oral contraceptive agents or as hormone replacement regimens in postmenopausal women) and corresponding exemplary regimens of doses are provided as follows.

One exemplary method (e.g., in premenopausal women) comprises administering to a female subject a multiphase regimen comprising a first phase in which an estrogen product is administered in combination with a progestin product; a second phase in which an estrogen product is administered in combination with a progestin product; and a third phase in which a progestin product is not administered; and wherein said first phase is about 14 days (2 weeks) or longer, or alternatively about 21 days or longer, or alternatively about 28 days or longer (e.g., greater than about 30, or 60, or 90, or 120 or 180 or 360 days) and wherein the progestin product administered in said second phase is at a dose effective to promote (or increase) apoptosis and/or TGF-β expression in ovarian epithelial cells and is characterized by at least twice, three-fold, 5-fold, 7-fold, 10-fold or 15-fold the effective dosage of the progestin product administered in said first phase. In premenopausal women, appropriate dosages in all phases may be selected to provide contraceptive effects as well, and dosages during the third phase may be selected so as to result in menses. An additional TGF-β inducing agent may be added.

Another exemplary method of preventing ovarian cancer comprises administering to a female subject a multiphase regimen comprising a first phase in which an estrogen product is administered; a second phase in which an estrogen product is administered in combination with a progestin product; and optionally a third phase in which a progestin product is not administered; and wherein said first phase is about 14 days (2 weeks) or longer, or alternatively about 21 days or longer, or alternatively about 28 days or longer (e.g., greater than about 30, or 60, or 90, or 120 or 180 or 360 days) and wherein the progestin product administered in said second phase is characterized by a dosage less than sufficient to prevent ovulation yet is a dose effective to promote apoptosis and/or TGF-β expression in ovarian epithelial cells.

A further exemplary method of preventing ovarian cancer comprises administering to a female subject a multiphase regimen comprising a first phase in which an estrogen product is administered; a second phase in which an estrogen product is administered in combination with a progestin product; and optionally a third phase in which a progestin product is not administered; and wherein said first phase is about 14 days (2 weeks) or longer, or alternatively about 21 days or longer, or alternatively about 28 days or longer (e.g., greater than about 30, or 60, or 90, or 120 or 180 or 360 days) and wherein the estrogen product administered in said first or second phase is characterized by a dosage less than sufficient to prevent ovulation and wherein the progestin product administered in said second phase is at a dose effective to promote apoptosis and/or TGF-β expression in ovarian epithelial cells.

Such methods characterized by administration of estrogen or progestin products at doses less than sufficient to prevent ovulation are particularly suitable for postmenopausal women.

According to an alternative aspect of the invention a method is provided of preventing ovarian cancer comprising administering to a female subject a multiphase regimen comprising a first phase in which an estrogen product is administered in combination with a progestin product; a second phase in which an estrogen product is administered in combination with a progestin product wherein the estrogen product is administered at a lower effective dosage than in said first phase; and a third phase in which an estrogen product is administered with a progestin product wherein the progestin product is administered at a higher effective dosage than in said first and second phases and promotes apoptosis and/or TGF-β expression in ovarian epithelial cells. Preferably the multiphase regimen has no breaks in hormone administration which would result in breakthrough bleeding, and would thus be particularly suitable for postmenopausal women.

The invention further provides a regimen of doses for prevention of ovarian cancer by promoting apoptosis in ovarian epithelial cells comprising a multiphase sequence of pharmaceutical dosages comprising a first series of dosages comprising an estrogen product and a progestin product; and a second series of dosages comprising an estrogen product and a progestin product; and wherein the number of dosages in the first series is sufficient for daily administration for a period of about 14 days (2 weeks) or longer, or alternatively about 21 days or longer, or alternatively about 28 days or longer (e.g., greater than about 30, or 60, or 90, or 120 or 180 or 360 days) and wherein the dosage of progestin product in said second series is effective to promote apoptosis and/or TGF-β expression in ovarian epithelial cells and is characterized by at least twice, three-fold, 5-fold, 7-fold, 10-fold or 15-fold the effective dosage of the progestin product in said first series. According to a preferred aspect this regimen further comprises a third series of dosages which are a placebo (to provide menses).

Additional regimens of dosages for prevention of ovarian cancer are those regimens for prevention of ovarian cancer comprising a multiphase sequence of pharmaceutical dosages comprising a first series of dosages comprising an estrogen product; and a second series of dosages comprising an estrogen product and a progestin product; and wherein the first series of dosages is sufficient for daily administration for a period of about 14 days (2 weeks) or longer, or alternatively about 21 days or longer, or alternatively about 28 days or longer (e.g., greater than about 30, or 60, or 90, or 120 or 180 or 360 days) and wherein the dosage of the progestin product in said second series is characterized by a dosage less than sufficient to prevent ovulation yet effective to promote apoptosis and/or TGF-β expression in ovarian epithelial cells. Alternatively, the dosage of the estrogen product in said second series is characterized by a dosage less than sufficient to prevent ovulation and the dosage of the progestin product in said second series is effective to promote apoptosis and/or TGF-β expression in ovarian epithelial cells.

The invention further provides a regimen of dosages for prevention of ovarian cancer comprising a multiphase sequence of pharmaceutical dosages comprising a first series of dosages comprising an estrogen product and a progestin product; a second series of dosages comprising an estrogen product and a progestin product wherein said estrogen product is administered at a lower effective dosage than in said first series; and a third series of dosages comprising a progestin product and an estrogen product wherein said progestin product is administered at a higher effective dosage than in said first series and promotes apoptosis. According to one preferred aspect of the invention, an additional apoptosis or TGF-β promoting agent may be combined with the progestin product in the third series. Alternatively, an additional TGF-β and/or apoptosis promoting agent may be administered during the first series.

According to one aspect of the invention, a regimen is provided which is contraceptive but which provides a particularly high dosage of a progestin product on a less frequent than a monthly basis designed to maximize the TGF-β and/or apoptotic effect of the progestin administration. Such regimens can include 60-day, 90-day, 180-day, 360-day and other regimens representing a duration of more than a single menstrual cycle.

Examples of 90 day regimens according to this aspect of the invention include those comprising administration for days 1–70 of a combination estrogen/progestin product such as 0.010 mg, 0.020 or 0.030 ethinyl estradiol+0.05 mg levonorgestrel or 0.010 mg, 0.020 mg or 0.03 mg ethinyl estradiol+0.075 mg levonorgestrel. During days 71–85 a different combination estrogen/progestin product is administered such as 0.030 mg ethinyl estradiol+0.15 mg or 0.25 mg or 0.5 mg levonorgestrel. This is then followed on days 86–90 with no drug administration or administration of a placebo. One effect of such a regimen is that menses would occur only once every three months corresponding to the period of administration of placebo. Such regimens could be altered with respect to dosages and timing and equivalent regimens could be prepared using combinations of other progestin and estrogen products according to the skill in the art.

Examples of 180 day regimens according to this aspect of the invention include those comprising administration for days 1–160 of a combination estrogen/progestin product such as 0.010 mg ethinyl estradiol+0.05 mg levonorgestrel or 0.020 mg ethinyl estradiol+0.05 mg levonorgestrel or 0.010 mg ethinyl estradiol+0.075 mg levonorgestrel or 0.020 mg ethinyl estradiol+0.075 levonorgestrel. During days 161–175 a different combination estrogen/progestin product is administered such as 0.030 mg ethinyl estradiol+0.15 mg, or 0.25 mg or 0.5 mg levonorgestrel. This is then followed on days 176–180 with no drug administration or administration of a placebo. Menses would then generally result only once every six months.

Other combination progestin/estrogen regimens are contemplated by the invention characterized by higher progestin to estrogen ratios.

According to one aspect of the invention, a regimen of dosages protective of ovarian epithelial cancer is provided for postmenopausal women with no uterus. Such a regimen provides essentially cyclic doses of high levels of progestin with or without estrogen. Suitable periodic regimens according to this aspect of the invention include a 30 day regimen comprising administration of an estrogen product alone such as at levels of 0.325 or 0.625 mg of conjugated estrogen for days 1–14 followed by a combination estrogen product with 0.15 mg or 0.25 mg or more levonorgestrel for days 15–25 followed by a placebo for days 26–30. Similar 60-day, 90-day, 180-day, 360-day and other regimens lasting multiples of 30 days and the like could be administered wherein, for example, an estrogen product is administered alone during days 1–40, 1–70, 1–160 or 1–340 respectively followed by administration of the combination estrogen/progestin product during days 41–55, 71–85, 161–175 or 341–355 and then followed by five days of a placebo (or no drug administration), respectively. Regimens of dosages (kits) providing such regimens can be supplied or kits comprising the progestin product component of such regimens can be provided to supplement an estrogen-only hormone replacement regimen in order to provide an ovarian cancer protective effect.

According to another aspect of the invention, a regimen for prevention of ovarian cancer in postmenopausal women is provided which is similar to that used in premenopausal women but would use the lowest dosages of estrogen and progestin products possible in combination with cyclic high dosages of progestin to achieve protection. According to one such regimen a dosage of estrogen comparable to 0.325 mg or 0.625 conjugated estrogen, i.e. 0.010 or 0.015 mg ethinyl estradiol, plus 0.05 levonorgestrel is administered daily for days 1–70 followed by administration on days 71–85 of the same dosage of an estrogen product plus 0.15 or 0.25 mg or more of levonorgestrel. A placebo (or no drug) is administered on days 86–90.

According to another regimen of the invention a progestin product is administered by sustained release such as by means of an implant which releases about 0.05 mg of levonorgestrel or its equivalent per day and is supplemented by administration of other apoptosis and/or TGF-β promoting agents such as a member selected from the group consisting of the retinoids, dietary flavanoids, anti-inflammatory drugs, monoterpenes, S-adenosyl-L-methionine, and Vitamin D products. The invention further provides regimens wherein the progestin product is administered at very high levels over short periods of time or where low levels of progestin products are administered followed by high levels for short durations. According to one example, progestin products are administered on a daily basis at levels of 0.05 mg levonorgestrel or less followed by administration of high levels of 0.15, 0.25, or 0.5 mg or more levonorgestrel for periods of 7 to 14 days.

A further ovarian cancer prevention regimen according to the invention comprises hormone administration to postmenopausal women with a uterus which is continuous with no breaks and which therefore achieves its effects while preventing breakthrough bleeding. A 60-day regimen according to this aspect of the invention comprises administration of 0.015 mg ethinyl estradiol plus 0.05 mg levonorgestrel for days 1–14 followed by administration of 0.010 mg ethinyl estradiol plus 0.05 mg levonorgestrel for days 15–40 followed by administration of 0.010 mg ethinyl estradiol plus 0.15 mg or 0.25 mg or more levonorgestrel for days 41–60.

In one mode of practicing this invention, it is first determined that a patient does not display any signs of ovarian cancer. The patient may in the alternative or in addition be determined to be a female at high risk of developing ovarian cancer. One aspect of this invention involves prescribing a regimen of a TGF-β inducing agent, alone or in combination with other compounds, to reduce the risk of developing ovarian cancer.

All doses given herein are appropriate for a female subject of about 60 kg weight; the dosages naturally can vary more or less depending on the weight of the subject. The doses may be increased or decreased, and the duration of treatment may be shortened or lengthened as determined by the treating physician. The frequency of dosing will depend on the pharmacokinetic parameters of the agents and the route of administration. The optimal pharmaceutical formulation will be determined by one skilled in the art depending upon the route of administration and desired dosage. See for example, Remington's Pharmaceutical Sciences, 18th Ed. (1990, Mack Publishing Co., Easton, Pa. 18042) pages 1435–1712, the disclosure of which is hereby incorporated by reference. Such formulations may influence the physical state, stability, rate of in vivo release, and rate of in vivo clearance of the administered agents.

Those of ordinary skill in the art will readily optimize effective dosages and concurrent administration regimens as determined by good medical practice and the clinical condition of the individual patient. Regardless of the manner of administration, the specific dose may be calculated according to body weight, body surface area or organ size. Further refinement of the calculations necessary to determine the appropriate dosage for treatment involving each of the above mentioned formulations is routinely made by those of ordinary skill in the art and is within the ambit of tasks routinely performed by them without undue experimentation, especially in light of the dosage information and assays disclosed herein. Appropriate dosages may be ascertained through use of established assays for determining dosages in conjunction with appropriate dose-response data. The final dosage regimen will be determined by the attending physician, considering various factors which modify the action of drugs, e.g. the drug's specific activity, the severity of the damage and the responsiveness of the patient, the age, condition, body weight, sex and diet of the patient, the severity of any infection, time of administration and other clinical factors. As studies are conducted, further information will emerge regarding the appropriate dosage levels for the treatment of various diseases and conditions.

It is contemplated that the routes of delivery of progestin products (either alone or in combination with other pharmaceuticals) could include oral, sublingual, injectable (including short-acting, depot, implant and pellet forms injected subcutaneously or intramuscularly), vaginal creams, suppositories, pessaries, rings, rectal suppositories, intrauterine devices, and transdermal forms such as patches and creams.

Another aspect of this invention is a pharmaceutical composition including a TGF-β inducing agent and/or apoptosis inducing agent combined with a statement that the composition reduces the risk of ovarian cancer. The statement can be in the form of a label, or packaging materials, or insert, or can be an oral statement. The invention includes a HRT formulation having a statement that the composition or regimen comprising the HRT regimen reduces the risk of ovarian cancer.

"Concurrent administration" or "co-administration" as used herein includes administration of the agents together, or before or after each other. The agents may be administered by different routes. For example, one agent may be administered intravenously while the second agent is administered intramuscularly, intravenously or orally. They may be administered simultaneously or sequentially, as long as they are given in a manner sufficient to allow both agents to achieve effective concentrations in the body.

The term "infertile female" as used herein includes post-menopausal and perimenopausal females past the age of reproduction and younger women not capable of conception, including ovulation, fertilization and implantation.

The term "effective for contraception" as used herein includes sufficient inhibition of fertility, including ovulation or implantation.

The term "contraceptive blood level" as used herein includes a blood level sufficient to inhibit fertility, including ovulation or implantation.

The term "females at high risk of developing ovarian cancer" includes females with a family history of breast or ovarian cancer, females with a prior history of breast or ovarian cancer, or females with a mutation in the BRCA1 or BRCA2 genes or any other mutation shown to be associated with a high risk of developing ovarian cancer.

The term "HRT" as used herein means hormone replacement therapy.

The term "OCP" as used herein means methods of contraception and contraception regimens and kits, whether taken orally or by some other non-oral, non-pill routes of delivery.

The term "Vitamin D compound" including "Vitamin D" "Vitamin D analogue" or "Vitamin D derivative" as used herein includes any compound which activates the Vitamin D Receptor, by binding or otherwise, either in its form of administration or in a form to which it is converted by processing by the human body. This definition thus includes each of Vitamins $D_1$, $D_2$, $D_3$, $D_4$ and $D_5$ and the various known analogues and derivatives thereof and any other agent that has Vitamin D activity or is an agonist thereof and that thereby increases the rate of apoptosis in ovarian epithelial cells. It is contemplated that not only presently available Vitamin D analogues and derivatives but also Vitamin D analogues and derivatives introduced in the future will be useful according to the present invention. Given the ability to produce the VDR recombinantly and models for determining VDR activation efficiency those of ordinary skill would be capable of identifying suitable Vitamin D compounds useful for practice of the present invention. Suitable analogues and derivatives are expected to include but are not limited to the following: 1α-hydroxyvitamin $D_3$; 25-hydroxyvitamin $D_3$; 1,24,25-$(OH)_3D_3$; 24,25-$(OH)_2D_3$; 1,25,26-$(OH)_3D_3$; 24,25-$(OH)_2D_3$; 1,25-dihydrox-16-ene-23-yne-26, 27-hexafluorocholecalciferol; 25,26-dehydro-1a,24R-dihydroxycholecalciferol and 25,26-dehydro-1a,24S-dihydroxycholecalciferol; 1a-hydroxy-19-nor-vitamin D analogues; 26,28-methylene-1a,25-dihydroxyvitamin $D_2$ compounds; 1a-hydroxy-22-iodinated vitamin $D_3$ compounds; 23-Oxa-derivatives of Vitamin D; and fluorinated Vitamin D analogues; 20-methyl-substituted Vitamin D derivatives; (E)-20(22)-Dehydrovitamin D compounds; 19-nor-Vitamin $D_3$ compounds with substituents at the 2-position; and 22-thio Vitamin D derivatives.

In this manner the adverse physiological effects of administering larger quantities of Vitamin D compounds and of progestin products can be minimized.

It is hypothesized that the combination of progestins and other compounds would have a synergistic effect, with reduced adverse side effects.

The levels of estrogen and/or progestin for contraceptive protection are well known in the art. (See Speroff et al., *Clinical Gynecologic Endocrinology and Infertility* (Chap. 15), 4th Ed. 1989, incorporated herein by reference).

Other aspects and advantages of the present invention will be understood upon consideration of the following illustrative examples. Example 1 addresses the effect of administration of progestin or estrogen products, alone or in combination, on the ovarian epithelial cells of monkeys. Example 2 addresses the effect of progestin in vitro on the ovaries of humans. Example 3 addresses the effect of progestins on apoptosis in the ovarian epithelium of domestic fowl. Example 4 relates to expression of the progesterone receptor in human ovarian tissue. Example 5 relates to a chemoprevention trial in domestic fowl. Example 6 addresses the effect of progestin and estrogen products, alone or in combination, on the ovaries of humans. Example 7 addresses the effect of hormonally active agents, alone or in combination, in vitro on human ovarian tissue. Example 8 addresses the effects of hormonally active agents in vivo on monkey ovaries. Example 9 addresses the effect of various hormonally active agents on the ovarian tissue of transgenic mice that have been altered to have altered expression of receptors, growth factors, integrins or protooncogenes. Example 10 addresses the apoptotic effects of Vitamin D in human ovarian epithelial cells. Example 11 describes induction of TGF-βs in human ovarian epithelial cells by Vitamin D or Vitamin D analogues. Example 12 describes an in vitro test to identify the most promising preventive agents. Example 13 describes an animal study to identify the most promising preventive agents.

EXAMPLE 1

Effect of Estrogen and Progestin in Vivo on Monkey Ovaries

Young female adult cynomolgus monkeys were fed a diet for three years that contained either no hormones, the oral combination contraceptive "Triphasil," the estrogenic component of "Triphasil" (ethinyl estradiol) alone, or the progestin component of "Triphasil" (levonorgestrel) alone, each administered in the same pattern that occurs in a "Triphasil" regimen. Doses were scaled on the basis of caloric intake, which is the accepted way to achieve human-equivalent doses. The human-equivalent doses were thus: six days of 0.030 mg ethinyl estradiol+0.050 mg levonorgestrel, followed by 5 days of 0.040 mg ethinyl estradiol+0.075 mg levonorgestrel, followed by days of 0.030 mg ethinyl estradiol+0.125 mg levonorgestrel, followed by 7 days of no treatment. This cyclic regimen was repeated every 28 days continuously for 2 years.

At the completion of the two years of the study, the animals were sacrificed, and their ovaries were removed and both formalin-fixed and paraffin embedded as well as flash frozen and stored at minus 70 degrees Celsius. Five-micron ovarian sections were mounted on coated slides, and stained with the Apoptag-plus kit (Oncor, Gaithersburg, Md.), which specifically labels the 3' end of free DNA fragments in cells undergoing DNA fragmentation, a characteristic of apoptosis. After staining, cells undergoing apoptosis were easily identified by their dark brown nuclear discoloration. The ovarian surface epithelium was examined histologically to assess ovarian epithelial morphology and to determine the percentage of ovarian cells undergoing apoptosis. To calculate the percentage of ovarian epithelial cells undergoing apoptosis, both the total number of ovarian epithelial cells and the number undergoing apoptosis were counted on each five-micron ovarian section. At each step, the investigators were completely blinded with regard to which treatment group was associated with each ovary.

The ovarian surface epithelium is comprised of a single layer of epithelial cells that rests on a basement membrane overlying the ovarian cortex. In the control and non-progestin treated monkeys, the ovarian surface epithelium typically had a lush appearance with the epithelial cells containing abundant cytoplasm and visible microvilli at the surface with apoptotic cells rarely seen. In the progestin treated monkeys, the ovarian surface epithelium was observed to contain numerous brown-staining apoptotic cells.

The median percentage of ovarian epithelial cells undergoing apoptosis for each of the treatment groups is shown below in Table 4.

TABLE 5

Apoptotic Effect of Four Treatments On Monkey Epithelia

| Treatment | Number | Median Percent of Apoptotic Cell Counts | Range Percent of Apoptotic Cell Counts |
|---|---|---|---|
| Control | 20 | 3.8% | 0.1–33.0% |
| Ethinyl-estradiol-only | 20 | 1.8% | 0.1–28.6% |
| Combination Pill | 17 | 14.5% | 3.0–61.0% |
| Levonorgestrel | 15 | 24.9% | 3.5–61.8% |

Multiple Comparisons:
Control - Levonorgestrel ($p < 0.001$)
Combination Pill - Ethinyl-estradiol ($p < 0.001$)
Ethinyl-estradiol - Levonorgestrel ($p < 0.001$)
Control - Combination Pill ($p < 0.001$)

From Table 5, the median percentage of apoptosis in the control group of monkeys not receiving any hormonal therapy was approximately 3.8%. Statistically, this was not significantly different from the rate of apoptosis seen in the ovarian epithelium in monkeys receiving only the estrogen component of "Triphasil," ethinyl estradiol, in which the median percentage of apoptosis was 1.8%.

A marked and significantly greater level of apoptosis was noted in the other two groups of monkeys that received either the combination pill (containing both ethinyl estradiol and levonorgestrel) or levonorgestrel (the progestin) alone. In this latter group (progestin alone), the observed median percentage of cells undergoing apoptosis was over six times greater than the level of apoptosis observed in the control, untreated monkeys. Because the only difference between the combination pill group and estrogen-alone group is the presence of the levonorgestrel component of the combination pill, and because the degree of apoptosis of the ovarian epithelium in the estrogen-alone group was no different than that of the control group, these data demonstrate that the accelerated rate of apoptosis in the ovarian epithelium in combination pill treated monkeys is due to the effects of the progestational component (levonorgestrel) of the combination pill. Moreover, the higher rate of apoptosis among the monkeys that received a progestational agent alone compared to the monkeys that received the combination pill, although not statistically significant, indicates that progestin-only treatment is more effective at inducing apoptosis of the ovarian surface epithelium than a progestin/ estrogen combination treatment.

In a similar experiment, the effect of hormone treatment on expression of TGF-$\beta$3 was examined in the ovaries of primates from the trial described above. This study uses monkeys that were randomized in the study above of apoptosis in the ovarian epithelium. This study consists of 74 monkeys: 73 with data on percentage of apoptosis and 1 that was excluded from the previous report for not having data on percentage of apoptosis. Hence, the number of cases for this study is as follows: Controls (19), Ethinyl Estradiol (21), Combination Pill (17), Levonorgestrel (17).

Ovarian sections from each of the monkeys were stained immunohistochemically for expression of TGF beta-3, using an anti-TGF-beta-3 monoclonal antibody. The antiTGF-beta antibody used is specific for TGF-beta 3, but cross reacts with TGF-beta 2, and does not cross react with TGf-beta 1. Two blinded observers then quantitated degree of expression of TGF-$\beta$3 by grading the intensity of staining on a scale of 1–4+ in several ovarian compartments: 1) epithelium, 2) oocytes, 3) endothelial cells, 4) granulosa cells. The staining was characterized as negative (0–2+) versus positive (3–4+). The following tables show the distribution of negative (0–2) and positive (3–4) staining among the randomized treatment groups for each separate ovarian compartment (i.e.: epithelial, oocyte cytoplasm, granulosa, and endothelial).

TABLE 6

Effect of Four Treatments on TGF beta-3 Expression in Monkey Ovarian Epithelium

| Epithelial staining | Positive | Negative | P (Exact test) |
|---|---|---|---|
| Controls (C) | 6 (32%) | 13 | <.001 |
| Ethinyl Estradiol (EE) | 2 (10%) | 19 | |
| Pill (P) | 17 (100%) | 0 | |
| Levonorgestrel (L) | 17 (100%) | 0 | |
| C + EE | 8 (20%) | 32 | <.001 |
| P + L | 34 (100%) | 0 | |

TABLE 7

Effect of Four Treatments on TGF beta-3 Expression in Monkey Ovarian Granulosa Cells

| Granulosa Cell staining | Positive | Negative | P (Exact test) |
|---|---|---|---|
| Controls | 12 (63%) | 7 | <.001 |
| EE | 8 (38%) | 13 | |
| Pill | 1 (6%) | 16 | |
| Levonorgestrel | 1 (6%) | 16 | |
| C + EE | 20 (50%) | 20 | <.001 |
| P + P | 2 (6%) | 32 | |

TABLE 8

Effect of Four Treatments on TGF beta-3 Expression in Monkey Ovarian Oocytes

| Oocyte cytoplasm staining | Positive | Negative | P (Exact test) |
|---|---|---|---|
| Controls | 14 (74%) | 5 | .45 |
| EE | 17 (81%) | 4 | |
| Pill | 16 (94%) | 1 | |
| Levonorgestrel | 14 (82%) | 3 | |
| C + E | 31 (78%) | 9 | .36 |
| P + L | 30 (88%) | 4 | |

TABLE 9

Effect of Four Treatments on TGF beta-3 Expression Monkey Ovarian Endothelial Cells

| Endothelial staining | Positive | Negative | P (Exact test) |
|---|---|---|---|
| Controls | 5 (26%) | 14 | <.001 |
| EE | 5 (23%) | 21 | |
| Pill | 16 (94%) | 1 | |

TABLE 9-continued

Effect of Four Treatments on TGF beta-3
Expression Monkey Ovarian Endothelial Cells

| Endothelial staining | Positive | Negative | P (Exact test) |
|---|---|---|---|
| Levonorgestrel | 16 (94%) | 1 | |
| C + EE | 10 (25%) | 30 | <.001 |
| P + L | 32 (94%) | 2 | |

The relationship between degree of expression of TGF-beta and percentage of apoptosis in the ovarian epithelium is given in the following table. The median percentage was compared for the 3 groups using the Wilcoxon rank sum test.

TABLE 10

Correlation between TGF beta-3 Expression and
Apoptosis in Monkey Ovarian Epithelial Cells

| Degree of staining for TGF-beta-3 | N | Median % apoptosis (range) | p |
|---|---|---|---|
| 1+ | 21 | 2.7 (0.1–28.6) | <.001 |
| 2+ | 10 | 6.5 (0.4–33) | |
| 3–4+ | 42 | 16.3 (0.2–61.8) | |

Conclusion: The data demonstrate a significant increase in expression of TGF beta-3 in ovarian epithelial cells in the progestin treated (pill or levonorgestrel) monkeys versus both controls and estrogen-only treated monkeys. Increases in expression of TGF beta-3 were also noted in the endothelial cells in the ovary in progestin treated monkeys. In contrast, a marked reduction in expression of TGF beta-3 was noted in granulosa cells with progestin treatment. More importantly, there was a highly significant correlation between TGF-β3 expression and apoptosis (p<0.001) in ovarian epithelial cells, suggesting that the apoptotic effect of progestin on the ovarian epithelium may be mediated by TGF-β3.

EXAMPLE 2

Effect of Progestin in Vitro on Human Ovarian Tissue

According to this example, levonorgestrel was found to induce apoptosis in immortalized human ovarian epithelial cells. Specifically, a spontaneously immortalized cell line, M-100, derived from a normal human ovarian epithelial cell culture was plated in 24 well plates at a concentration of 100,000 cells per well. After 24 hours, the wells were treated with either levonorgestrel (20 ng/ml) or control medium, and allowed to incubate for 96 hours. All experiments were performed in triplicate. After 96 hours, cell lysates were extracted from each of the wells, normalized for cell number, and analyzed for DNA-histone complexes indicative of apoptosis using a cell death ELISA (Boehringer Mannheim). A statistically significant (100%) increase in apoptosis was measured in M-100 cells treated with levonorgestrel as compared to controls (P<0.05).

In addition, M-100 cells were grown to confluence in 60 millimeter dishes and then treated with levonorgestrel (100 uM) for 12, 24, 48, 72 and 96 hours. Then, cells were harvested, centrifuged at 6000 g for 10 minutes and the resultant pellets were resuspended in 200 ul nuclei lysis buffer (5M guanidine thiocyanate, 25 mM sodium citrate pH 7.0, 100 mM β-mercaptoethanol). DNA was precipitated with an equal volume of isopropanol at −70° C. for one hour. Samples were centrifuged for 30 minutes at 12,000 g at 4° C., and the DNA pellets were washed in 70% ethanol at room temperature. Pellets were resuspended in TE buffer and incubated overnight at 37° C. with 0.5 mg/ml RNase A (Sigma Chemical Co., St. Louis, Mo.). Pellets were again resuspended and an optical density reading at 260 nm wavelength was obtained on a Perkin Elmer Lambda 3B UV/vis spectrophotometer to determine the concentration of DNA. Equal amounts of each DNA sample were then subjected to electrophoresis on a horizontal 1.5% agarose gel containing ethidium bromide and visualized under UV illumination. DNA ladders indicative of apoptosis were observed at 48, 72 and 96 hours in M-100 cells treated with levonorgestrel, with no evidence of apoptosis observed in control cultures treated with the appropriate control vehicle solution.

EXAMPLE 3

Apoptosis in Domestic Fowl

According to this example, levonorgestrel was found to induce apoptosis in the ovarian epithelium of domestic fowl. Domestic fowl is the one animal species with a high incidence of spontaneous ovarian carcinoma. Specifically, ovarian epithelial cells from domestic hens were cultured using the scrape method according to the method of Arends et al., Int. Rev. Exp. Pathol 32:223–254 (1991). The avian ovarian epithelial cell cultures were treated with levonorgestrel (100 uM) for 96 hours. DNA was extracted using the method described in example 2 and subjected to electrophoresis. A DNA ladder indicative of apoptosis was observed in avian ovarian epithelial cells treated with progestin, with no effect observed in the control cells.

EXAMPLE 4

Progesterone Receptor Expression in Human Ovaries

According to this example, the expression of progesterone receptor was examined in the normal human ovary. Immunohistochemical staining for progesterone receptor was performed on normal ovarian tissue samples obtained from 40 women who underwent oophorectomy as part of a gynecologic procedure performed for benign gynecologic indications. The progesterone receptor was found to be uniformly expressed by the ovarian epithelium in all cases, including the ovaries from both pre-and post-menopausal women. In addition, progesterone receptor expression was detected in the ovarian epithelium lining inclusion cysts trapped within the ovarian stroma. Progesterone receptor expression was absent in all non-epithelial areas of the ovary.

EXAMPLE 5

Chemoprevention Trail in Domestic Fowl

The domestic fowl has great potential as an animal model for studying chemoprevention of ovarian cancer as it is the only known animal model with a high incidence of spontaneous ovarian adenocarcinoma is the domestic fowl. Fredrickson, Environ Health Perspect 73: 35–51 (1987) reported that in two flocks of hens with initial ages of either two or three years, followed prospectively until ages 3.9 to 4.2 years, there were 33 cases of ovarian adenocarcinoma in 236 chickens. This gives an incidence of 14 percent in the two-year period of observation.

In addition to its known high incidence of ovarian cancer, there are other features of the domestic fowl that make it attractive for studying chemoprevention of ovarian cancer, particularly with progestin agents: (1) The ovulatory cycle in the domestic fowl has been extensively studied and characterized previously, and is highly regulated by gonadotropins, estrogens, androgens and progestin. (2) Under standard conditions, the domestic fowl ovulates on almost a daily basis. However, anovulation can be induced under controlled conditions that include dietary restriction. It has been shown in a long term, one year, study in broiler hens, for example, that dietary restriction to maintain pullet weight (beneath the minimum required to support egg production) causes complete cessation of ovulation. Dunn et al., Poultry Science 71:2090–2098 (1992). Thus, ovulation in the domestic fowl can be carefully controlled, allowing the design of experiments that can test the relative importance of ovulation inhibition versus molecular biologic effects of contraceptives with regard to chemoprevention of ovarian cancer. (3) Expression and regulation of known effectors of apoptosis such as bax, bcl-2, and p53 have been studied extensively in the domestic fowl. (4) The ovarian epithelium in the domestic fowl expresses progestin receptor in both the A and B isoforms. (5) We have been able to induce apoptosis with the progestin levonorgestrel in cultured normal ovarian epithelial cells from the chicken (see the data of Example 3).

Progestin Treatment Decreases the Number of Tumors in Egg Laying Hens

A two-year prevention trial was performed in the chicken, designed to test the hypothesis that progestins confer prevention against ovarian cancer. Two thousand two year-old birds were randomized into several groups, including untreated controls, and groups receiving the progestins provera or levonorgestrel. The trial has just completed, and tumors accrued during the trial are currently being studied. Preliminary results suggest that at the two-year mark, chickens in groups treated with the progestins levonorgestrel and provera contained 35% fewer ovarian and oviductal tumors than controls. Interestingly, all birds in this study were maintained under conditions of feed restriction, which induces an anovulatory state. Thus, the study suggests an ovarian-cancer-protective effect of progestins, unrelated to ovulation.

EXAMPLE 6

Effect of Progesting and Estrogen in Vivo on Human Ovaries

Various progestins alone, including pregnanes, estranes and gonanes, various estrogens alone, or various progestin-estrogen combinations at varying doses are administered to women for at least one month prior to a scheduled surgery for removal of the ovaries and uterus. In particular, regimens of estrogen alone, estrogen with medroxyprogesterone acetate (or another 17-hydroxy-progesterone derivative), and estrogen with levonorgestrel (or another 19-nortestosterone derivative) are evaluated. To evaluate the effects of the different dosage regimens, the ovaries are examined for various markers, including apoptosis and TGF-beta expression.

EXAMPLE 7

Effect of Hormonally Active Agents in Vitro on Human Ovarian Tissue

Ovarian epithelia cultured from ovaries removed from normal women or women with epithelial ovarian cancer are treated with various progestins alone, including pregnanes, estranes and gonanes, various estrogens alone, various progestin-estrogen combinations, progesterone receptor agonists, progesterone receptor antagonists, estrogen receptor agonists, or estrogen receptor antagonists, each at varying doses and varying durations, from e.g., 24 hours to 7 days. The ovarian tissue is then examined for various markers, including apoptosis and TGF-beta. The most potent agent for inducing TGf-beta expression and apoptosis are determined.

EXAMPLE 8

Effect of Hormonally Active Agents in Vivo on Monkey Ovaries

Mature young female monkeys are treated with one of the following: control, leuprolide acetate (a gonadotropin releasing hormone [GnRH or LHRH] agonist), various oral contraceptives, levonorgestrel, norethindrone, medroxyprogesterone acetate, ethinyl estradiol, testosterone, testosterone derivatives, RU486, progestin agonists, progestin antagonists, estrogen agonists and estrogen antagonists, each at varying doses. The ovarian tissue is removed and examined for various markers, including apoptosis and TGf-beta expression.

EXAMPLE 9

Effect of Hormonally Active Agents in Vivo on Ovaries of Transgenic Mice

The apoptotic and TGf-beta inducing effect of various progestins, estrogens or androgens, each at varying doses, is evaluated on the ovarian tissue of transgenic mice or Domestic hens that have been altered to "knockout" their progestin receptor, to have an altered expression of the estrogen receptor, to express BRCA1, or to have altered expression of growth factors, integrins or protooncogenes.

EXAMPLE 10

Example 10 addresses the effect of administration of Vitamin D on human ovarian epithelial cells. According to this example, a cell culture derived from normal ovarian epithelial cells was plated in 24 well plates at a concentration of 100,000 cells per well. After 24 hours, the wells were treated with 1,25-dihydroxyvitamin $D_3$ at a 100 nM concentration or control medium, and allowed to incubate for 96 hours. All experiments were carried out in triplicate. After 96 hours, cell lysates were extracted from each of the wells, and the cytoplasmic fraction was normalized for cell number and analyzed for DNA-histone complexes indicative of apoptosis using a cell death ELISA (Boehringer Mannheim). A significant (300%) increase in apoptosis (p=0.01) was measured in the human ovarian epithelial cells treated with Vitamin D as compared with the controls.

EXAMPLE 11

Induction of TGF-$\beta$3 by Vitamin D Compounds in Human Ovarian Epithelial Cells in Vitro An immortalized cell line, M-100, derived from a normal human ovarian epithelial cell culture established in our laboratory was plated in 100 mm plates at a concentration of 1 million cells per plate, in the presence of either 1,25 (OH)2 D3 or the Vitamin D analogue E1089 at doses of each (100 nM) or control medium, and allowed to incubate for 72 hours. After 72 hours, cells were scraped from each of the plates, fixed on glass slides, and stained immunohistochemically with anti-TGF $\beta$3 antibody. A significant increase in TGF $\beta$3 expression was observed in M-100 cells treated with Vitamin D agents as compared to controls. These data demonstrate direct induction of TGF-β3 expression in human ovarian epithelial cells by Vitamin D.

EXAMPLE 12

In Vitro Testing to Identify Most Effective Agents for Prevention of Ovarian Cancer For these experiments, the relative apoptosis and TGF β-inducing effects of a variety of progestins including progestin agonists and antagonists are tested on cultured ovarian epithelial cells in vitro, using methods described in Examples 2, 6, 7, 10 and 11. Given the different binding patterns of the known progestins to various receptors (progestin, androgen and estrogen receptors), the estrogenic, progestogenic and androgenic activity can vary in amount between the different synthetic progestin formulations, thus leading to varying degrees of progestin and androgenic activity. For example, the progestin binding activity of norethindrone is less than 20% that of levonorgestrel while the binding infinity of norethindrone to the androgen receptor is less than 50% of the binding activity of levonorgestrel. By studying the TGF-β and apoptosis-inducing effects of progestins from all three classes (pregnane, estrane, and gonane), and elucidating the progestin receptor signaling pathways in the ovarian epithelium, the characteristics of progestins that result in an optimal induction of TGF-β and apoptosis in ovarian epithelial cells are determined, and the progestins that hold the greatest potential for ovarian cancer prevention are identified. It is possible, for example, that progestins that preferentially regulate A or B receptor isoform activity will lead to more potent induction of TGF-β expression or apoptosis in ovarian epithelial cells. In similar experiments, the relative TGF-β-inducing or apoptosis-inducing effects of other agents are listed in ovarian epithelial cells to identify candidate agents that have the potential to confer protection against ovarian cancer. The effects of these agents on ovarian epithelial cells are determined, both alone and in combination with progestins and antiprogestins, and optimal pharmaceutical combinations for ovarian cancer prevention are identified.

EXAMPLE 13

A Chemoprevention Trial is Performed in the Chicken to Identify the Agents that Confer the Greatest Prevention Against Ovarian Cancer This experiment is performed in a manner similar to that described in example number five. The most promising agents are identified from examples number 6,7,8,9,10 and 12 above. These agents are then tested in the chicken ovarian cancer model, and the most effective agents are then incorporated in a regimen to be used by women.

What is claimed is:

1. A hormonal regimen wherein at least one of the daily dosages has at least 0.5 mg of norgestrel and an estrogen component with less than 50 mcg EE equivalent.

2. The regimen of claim 1 wherein said regimen is for oral contraception.

3. The regimen of claim 2 wherein said estrogen component does not exceed 35 mcg EE equivalent.

4. The regimen of claim 3 wherein said estrogen component does not exceed 20 mcg EE equivalent.

5. The regimen of claim 4 wherein said daily dosage has 0.5 mg of norgestrel.

6. The regimen of claim 4 wherein said estrogen component does not exceed 15 mcg EE equivalent.

7. The hormonal regimen of claim 1 wherein said regimen is multi-phasic, with one phase having a daily dosage equivalent of norgestrel of at least 0.5 mg and another phase having daily dosage of norgestrel of less than 0.5 mg.

8. The hormonal regimen of claim 1 wherein said hormonal regimen is for hormone replacement therapy regimen for administration to peri-menopausal women.

9. The hormonal regimen of claim 8 wherein said estrogen component does not exceed 5 mcg EE equivalent.

10. The hormonal regimen of claim 1 wherein said hormonal regimen is for hormone replacement therapy regimen for administration to post-menopausal women.

11. The hormonal regimen of claim 10 wherein said estrogen component does not exceed 5 mcg EE equivalent.

12. A hormonal regimen wherein at least one of the daily dosages has at least 1.0 mg of ethinodiol diacetate and an estrogen component with less than 50 mcg EE equivalent.

13. The regimen of claim 12 wherein said regimen is for oral contraception.

14. The regimen of claim 13 wherein said estrogen component does not exceed 35 mcg EE equivalent.

15. The regimen of claim 14 wherein said estrogen component does not exceed 20 mcg EE equivalent.

16. The regimen of claim 15 wherein said daily dosage has 1.0 mg of ethinodiol diacetate.

17. The regimen of claim 15 wherein said estrogen component does not exceed 15 mcg EE equivalent.

18. The hormonal regimen of claim 12 wherein said regimen is multi-phasic, with one phase having a daily dosage equivalent of ethinodiol diacetate of at least 1.0 mg and another phase having daily dosage of ethinodiol diacetate of less than 1.0 mg.

19. The hormonal regimen of claim 12 wherein said hormonal regimen is for hormone replacement therapy regimen for administration to peri-menopausal women.

20. The hormonal regimen of claim 19 wherein said estrogen component does not exceed 5 mcg EE equivalent.

21. The hormonal regimen of claim 12 wherein said hormonal regimen is for hormone replacement therapy regimen for administration to post-menopausal women.

22. The hormonal regimen of claim 21 wherein said estrogen component does not exceed 5 mcg EE equivalent.

23. A hormonal regimen wherein at least one of the daily dosages has greater than 10 mg of at least one progestin selected from the group consisting of norethindrone, norethinodryl and norethinodrel and an estrogen component with less than 50 mcg EE equivalent.

24. The regimen of claim 23 wherein said regimen is for oral contraception.

25. The regimen of claim 24 wherein said estrogen component does not exceed 35 mcg EE equivalent.

26. The regimen of claim 25 wherein said estrogen component does not exceed 20 mcg EE equivalent.

27. The regimen of claim 26 wherein said daily dosage has 10 mg of said progestin.

28. The regimen of claim 26 wherein said estrogen component does not exceed 15 mcg EE equivalent.

29. The hormonal regimen of claim 23 wherein said regimen is multi-phasic, with one phase having a daily dosage equivalent of said progestin of at least 10 mg and another phase having daily dosage of said progestin of less than 10 mg.

30. The hormonal regimen of claim 23 wherein said hormonal regimen is for hormone replacement therapy regimen for administration to peri-menopausal women.

31. The hormonal regimen of claim 30 wherein said estrogen component does not exceed 5 mcg EE equivalent.

32. The hormonal regimen of claim 23 wherein said hormonal regimen is for hormone replacement therapy regimen for administration to post-menopausal women.

33. The hormonal regimen of claim 32 wherein said estrogen component does not exceed 5 mcg EE equivalent.

* * * * *